United States Patent [19]

Nakai et al.

[11] Patent Number: 5,847,098
[45] Date of Patent: Dec. 8, 1998

[54] DNA ENCODING INTERLEUKIN IL-1β MUTANT

[75] Inventors: Satoru Nakai; Mayumi Kaneta; Yoshikazu Kikumoto, all of Tokushima-ken; Yeong-Man Hong, Naruto; Kazuyoshi Kawai, Tokushima-ken; Setsuko Takegata, Tokushima; Kiyoshi Ishii, Tokushima-ken; Yasuo Yanagihara, Tokushima; Yoshikatsu Hirai, Tokushima-ken, all of Japan

[73] Assignee: Otsuka Pharmaceutcal Co., Ltd., Osaka, Japan

[21] Appl. No.: 474,168

[22] Filed: Jun. 7, 1995

Related U.S. Application Data

[60] Division of Ser. No. 24,386, Mar. 10, 1987, which is a continuation-in-part of Ser. No. 810,776, Dec. 19, 1985, Pat. No. 4,898,818.

[30] Foreign Application Priority Data

| Jun. 24, 1985 | [JP] | Japan | 60-138280 |
| Jun. 24, 1985 | [JP] | Japan | 60-138281 |
| Oct. 3, 1985 | [JP] | Japan | 60-220882 |
| Mar. 14, 1986 | [JP] | Japan | 61-057885 |
| Jun. 20, 1986 | [JP] | Japan | 61-145830 |
| Jul. 9, 1986 | [JP] | Japan | 61-161184 |
| Aug. 27, 1986 | [JP] | Japan | 61-200324 |
| Dec. 21, 1994 | [JP] | Japan | 59-271207 |

[51] Int. Cl.$^6$ ............... C12N 15/24; C12N 5/10
[52] U.S. Cl. ............... 536/23.5; 435/71.1; 435/71.2; 435/69.52; 435/172.3; 435/252.3; 435/320.1; 935/11; 935/22; 935/66; 935/72; 530/351
[58] Field of Search ........... 536/23.1, 23.5; 435/69.52, 71.1, 172.3, 71.2, 252.3, 320.1; 935/11, 22, 66, 72; 424/85.2; 514/2, 12, 885; 530/351

[56] References Cited

U.S. PATENT DOCUMENTS

| 4,518,584 | 5/1985 | Mark et al. | 530/351 |
| 4,568,640 | 2/1986 | Rubin | 435/68 |
| 4,762,914 | 8/1988 | Auron et al. | 530/351 |
| 4,766,069 | 8/1988 | Auron et al. | 435/240.1 |
| 4,959,314 | 9/1990 | Mark et al. | 435/69.1 |

FOREIGN PATENT DOCUMENTS

| 8652451 | 7/1986 | Australia . |
| 0109748 | 5/1984 | European Pat. Off. . |
| 0155433 | 9/1985 | European Pat. Off. . |
| 0161901 | 11/1985 | European Pat. Off. . |
| 0165654 | 12/1985 | European Pat. Off. . |
| 0188864 | 7/1986 | European Pat. Off. . |
| 0188920 | 7/1986 | European Pat. Off. . |
| 0200986 | 11/1986 | European Pat. Off. . |
| 34919 | of 1985 | Japan . |
| 60-149386 | 8/1985 | Japan . |
| WO 8500830 | 2/1985 | WIPO . |
| WO 8504421 | 10/1985 | WIPO . |

OTHER PUBLICATIONS

Zoller et al, *Nucleic Acid Res.*, 10(20):6487–6500 (1982).
Clark et al, *Nucleic Acid Res.*, 14920):7897–7914 (1986).
Tsuji et al, *Biochem.*, 26:3129–3134 (1987).
Wang et al, *Science*, 224:1431–1443 (1984).
Wells et al, *Gene*, 34:315–323 (1985).
Suhamanian, *Bio/Technol*, 3:597 (1985).
Von Heijne, *Eur. J. Biochem.*, 133:17–21 (1983).
Perlman et al, *J. Mol. Biol.*, 167:391–409 (1983).
Inouge et al, *Protein Engineering*, Ed., pp 157–171 (1986).
Robinson et al, *introduction to Proteins and Protein Engineering*, pp. 258–259 (1986).
Regenmortel, *TIBS*, 11:36–39 (1986).
Darrel et al, *Nature*, 283:433 (1980).
March et al, *Nature*, 315(6021):641–647 (1985).
Dinarello, *Reviews of Infections Diseases*, 691):51–95 (1984).
*J. of Immunology*, 122(5):2112–2118 (1979).
*Federation Proceedings*, 41(2):257–262 (1982).
*Cellular Immunology*, 80:223–229 (1983).
*Nature*, 309:56–59 (1984).
*J. Exp. Med.*, 160:772–787 (1984).
*Cellular Immunology*, 48:433–436 (1979).
*The New England Journal of Medicine*, 311(22):1413 (1984).
*Proc. Natl. Acad. Sci., U.S.A.*, 81:7907–7911 (1984).
*Nucleic Acid Res.*, 13(16)L5869–5882 (1985).
*Nature*, 304:449–451 (1983).
*Cellular Immunology*, 63:164–176 (1981).
*J. Exp. Med.*, 150:709–714 (1979).
*J. of Immunology*, 130(6):2708–2714 (1983).
*J. of Immunology*, 132(3):1311–1316 (1984).
*Nature*, 314:266–268 (1985).
*Nature*, 312:458–462 (1984).
*Biochemical and Biophysical Research Communications*, 14(1):285–291 (1986).
*J. Exp. Med.*, 161:490–502 (1985).
*J. Exp. Med.*, 164:237–250 (1986).
*J. of Immunology*, 135(6):3962–3968 (1985).
*J. of Immunology*, 136(7):2483–2485 (1986).
*J. of Immunology*, 136(7):2492–2497 (1986).
*J. of Immunology*, 136(9):3304–3310 (1986).
*Immunology Today*, 7(2):45–56 (1986).
*Jpn. J. Cancer Res. (Gann)*, 77:767–773 (1986).

(List continued on next page.)

*Primary Examiner*—John Ulm
*Assistant Examiner*—Prema Mertz
*Attorney, Agent, or Firm*—Sughrue, Mion, Zinn, Macpeak & Seas PLLC

[57] ABSTRACT

A homogeneous interleukin 1β (IL-1β), its derivative having a modified amino acid sequence of IL-1β, a gene coding for said derivative, medical composition comprising said derivative as a pharmaceutically effective component and a medicinal use of homogeneous IL-1β and the derivative.

5 Claims, 33 Drawing Sheets

OTHER PUBLICATIONS

*Proceedings of AACR,* 26:269 and 1058 (1985).

*The Physiologic, Metobolic, and Immunologic Actions of interleukin–1:* (Proceedings of a Symposium Held in Ann Arbor, Michigan, Jun. 4–6, 1985), pp. 253–262, Alan R. Liss, Inc., New York.

*Eur. J. Immunol.,* 14:898–901 (1984).

*Bio/Technology,* 4:1078–1082 (1986).

*Clin. Exp. Immunol.,* 55:295–302 (1984).

*Arthritis and Rheumatism,* 26(8):975–983 (1983).

*Arthritis and Rheumatism,* 28(8):853–862 (1985).

*Immunological Rev.,* 63:51–72 (1982).

*J. of Immunol.,* 136(8):3098–3102 (1986).

*J. Clin. Invest.,* 79:48–51 (1987).

*6th International Congress of Immunology,* Abstracts, Jul. 6–11, 1986, Toronto, Canada, pp. 343–346, 349, 350–354 (particularly Theme Nos. 3.31.14, 3.31.22, 3.31.43, 3.31.39, 3.31.40, 3.31.38 and 3.32.23).

*Metabolism,* 23, Extra Ed. "Immunology '86", pp. 97–104 (1986).

*Biochemical and Biophysical Research Communications,* 143(1):345–352 (1987).

*Medical Immunology,* 12(6):753–760 (1986).

*Proc. Jap. Soc. Immunol.,* 16:167 and 173 (1986).

*Biochemistry,* 58(8):840 (1986).

*Jpn. J. Clin. Immunol.,* 9(5):330–332 (1986).

*J. Exp. Med.,* 162:790–801 (1985).

Wingfield et al, *Eur. J. Biochem.,* 160:491–497 (1986).

Meyers, *J. Biol. Chem.,* 262:11176–11181 (1987).

Narachi et al, *J. Biol. Chem,* 262:13107–13110 (1987).

Arakawa et al, *Protein Engineering,* 3:721–724 (1990).

Yamagishi et al, *Protein Engineering,* 3:713–719 (1990).

Perry et al, *Science,* 226:555–557 (1984).

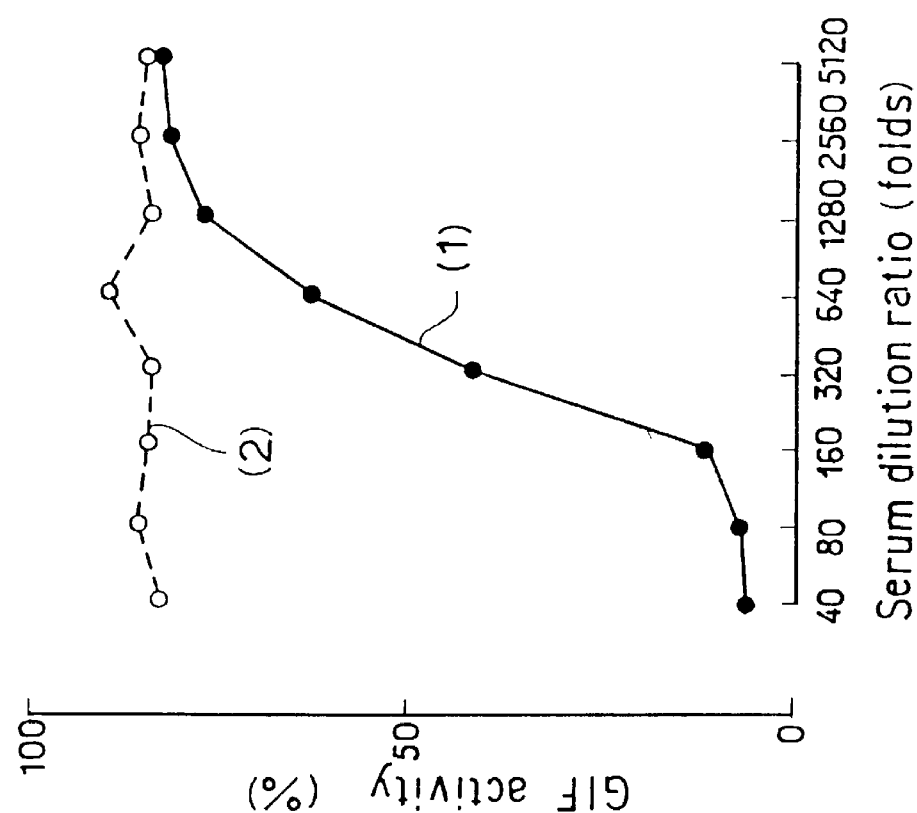
FIG. 21-b
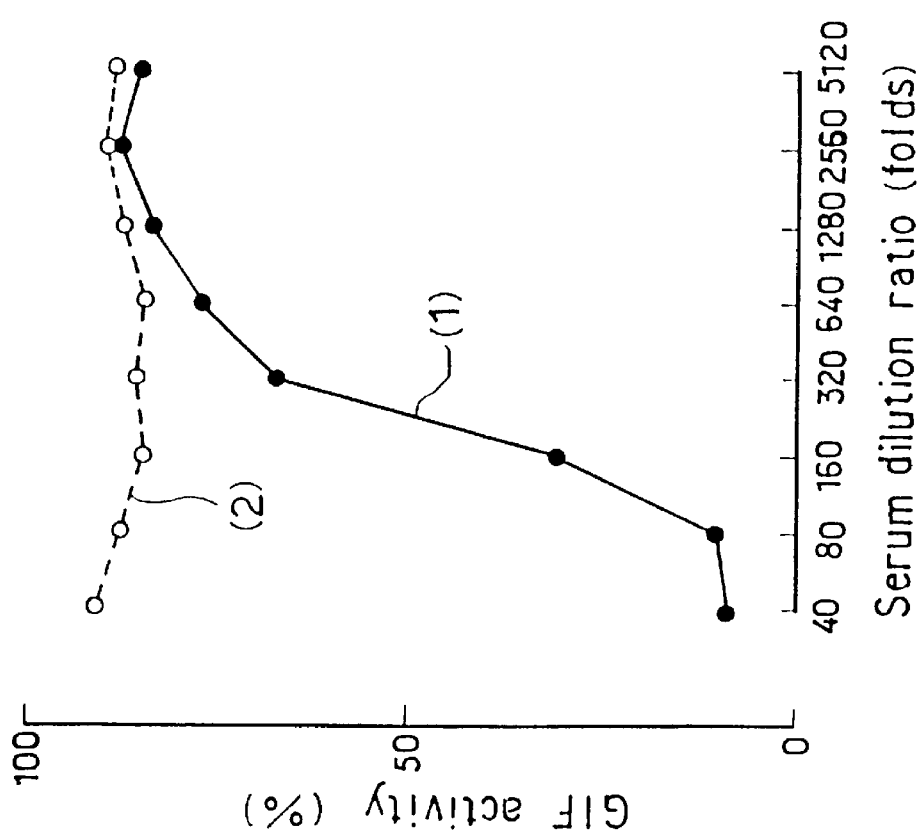
FIG. 21-a

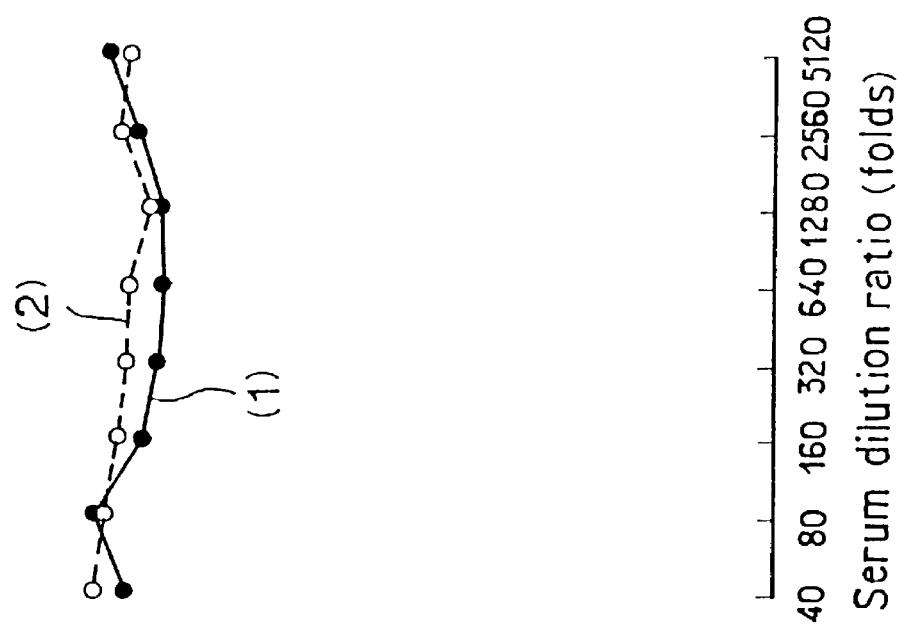
FIG. 21-c
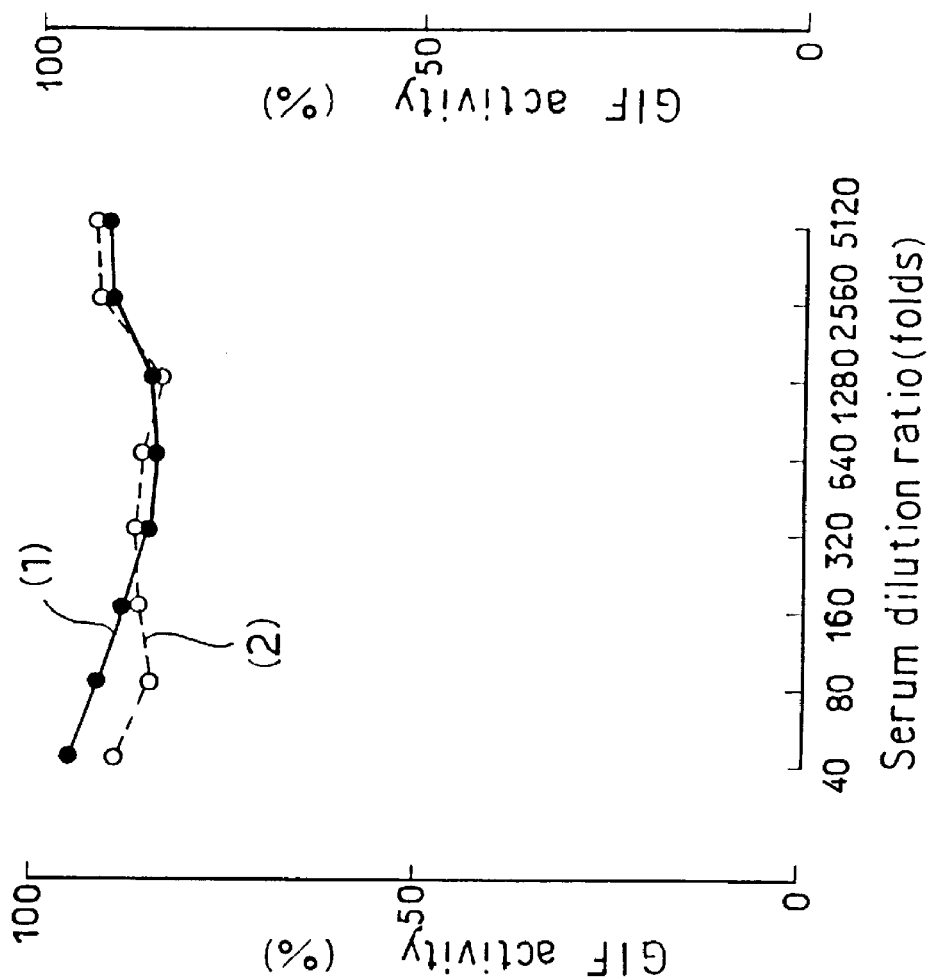
FIG. 21-d

DNA ENCODING INTERLEUKIN IL-1β MUTANT

This is a Divisional application of application Ser. No. 07/024,386, filed Mar. 10, 1987; which is a Continuation-In-Part of application Ser. No. 06/810,776, filed Dec. 19, 1985, now U.S. Pat. No. 4,898,818.

The present invention relates to novel polypeptides, and more particularly to novel homogeneous interleukin-1β (hereinafter referred to as IL-1β) and novel derivatives thereof, and to the medicinal use of the IL-1β and novel derivatives thereof.

The Second International Lymphokine Workshop decided to adopt a unified name, interleukin-1 (IL-1), for the physiologically active substances which had been referred to as lymphocyte activating factor (LAF), mitogenic protein, helper peak-1, T-cell replacing factor III (TRF-III), T-cell replacing factor Mφ (TRFM), B-cell activating factor, B-cell differentiation factor, etc. (Cellular Immunol., 48, 433–436 (1979)). This decision is based on the reason that these physiologically active substances can not be distinguished from one another as different substances but are expressed variously merely with reference to physiological activities as interpreted from different angles.

Further it is reported that IL-1 activates T lymphocytes and B lymphocytes, has activity to promote production of interleukin-2 and antibodies, acts on liver tissues to promote protein synthesis and possesses activity to promote production of prostaglandins (see Reviews of Infectious Disease, Vol. 6, No.1, 51–59 (1984), New England J. of Med., 311, 1413 (1984), etc.).

Whereas IL-1 itself still remains to be clarified as a substance, it is only recently that reports are made on the presence of two different genes coding for polypeptides having LAF activity or precursor thereof (Proc. Natl. Acad. Sci., Vol. 81, 7907–7911 (1984), Nature, Vol. 315, 641 (1985), Nucleic Acid Research, Vol. 13 (16), 5869 (1985)). These reports mention "IL-1α" having a sequence of 159 amino acids and "IL-1β" comprising 153 amino acids which are postulated from the base sequences of the two genes.

Nevertheless, research has yet to be made to clarify the relation between said activities assayed using a conditioned medium or so called partially purified IL-1 and the polypeptide postulated from the above base sequences.

Known IL-1 as a physiologically active substance is also thought to be identical with an endogeneous pyrogen (EP) and is known to exhibit a pyrogenic property (see Nature, 304, 449 (1983); Cell Immunol., 63, 164 (1981); J. Exp. Med., 150, 709 (1979); J. Immunol., 130, (6) 2708 (1983); same, 132 (3) 1311 (1984); etc.). This indicates that IL-1, if available as a uniform substance, to say nothing of physiologically active conventional IL-1, is difficult to use for medical applications.

An object of the present invention is to provide polypeptides which are novel and useful IL-1β and derivatives thereof effectively usable for medicinal applications.

Another object of the invention is to provide a medicinal use for polypeptides which are novel IL-1β and derivatives thereof.

Another object of the invention is to provide a gene coding for a novel IL-1β derivative and a process for preparing the IL-1β derivative by gene engineering techniques using the gene.

The above and other objects of the invention will become apparent from the following description.

The IL-1β of the present invention is a homogeneous polypeptide or protein having the amino acid sequence of the following formula (A).

The IL-1β derivatives of the invention is characterized in that the derivative has a modified amino acid sequence fulfilling at least one of the following requirements a) to d) in the amino acid sequence represented by the formula (A).

$$\begin{array}{l}
\text{Formula (A)}\\
\phantom{xx}5\phantom{xxxxxxxxxxxx}10\\
\text{Ala—Pro—Val—Arg—Ser—Leu—Asn—Cys—Thr—Leu—}\\
\phantom{xx}15\phantom{xxxxxxxxxxxx}20\\
\text{Arg—Asp—Ser—Gln—Gln—Lys—Ser—Leu—Val—Met—}\\
\phantom{xx}25\phantom{xxxxxxxxxxxx}30\\
\text{Ser—Gly—Pro—Tyr—Glu—Leu—Lys—Ala—Leu—His—}\\
\phantom{xx}35\phantom{xxxxxxxxxxxx}40\\
\text{Leu—Gln—Gly—Gln—Asp—Met—Glu—Gln—Gln—Val—}\\
\phantom{xx}45\phantom{xxxxxxxxxxxx}50\\
\text{Val—Phe—Ser—Met—Ser—Phe—Val—Gln—Gly—Glu—}\\
\phantom{xx}55\phantom{xxxxxxxxxxxx}60\\
\text{Glu—Ser—Asn—Asp—Lys—Ile—Pro—Val—Ala—Leu—}\\
\phantom{xx}65\phantom{xxxxxxxxxxxx}70\\
\text{Gly—Leu—Lys—Glu—Lys—Asn—Leu—Tyr—Leu—Ser—}\\
\phantom{xx}75\phantom{xxxxxxxxxxxx}80\\
\text{Cys—Val—Leu—Lys—Asp—Asp—Lys—Pro—Thr—Leu—}\\
\phantom{xx}85\phantom{xxxxxxxxxxxx}90\\
\text{Gln—Leu—Glu—Ser—Val—Asp—Pro—Lys—Asn—Tyr—}\\
\phantom{xx}95\phantom{xxxxxxxxxxxx}100\\
\text{Pro—Lys—Lys—Lys—Met—Glu—Lys—Arg—Phe—Val—}\\
\phantom{xx}105\phantom{xxxxxxxxxxxx}110\\
\text{Phe—Asn—Lys—Ile—Glu—Ile—Asn—Asn—Lys—Leu—}\\
\phantom{xx}115\phantom{xxxxxxxxxxxx}120\\
\text{Glu—Phe—Glu—Ser—Ala—Gln—Phe—Pro—Asn—Trp—}\\
\phantom{xx}125\phantom{xxxxxxxxxxxx}130\\
\text{Tyr—Ile—Ser—Thr—Ser—Gln—Ala—Glu—Asn—Met—}\\
\phantom{xx}135\phantom{xxxxxxxxxxxx}140\\
\text{Pro—Val—Phe—Leu—Gly—Gly—Thr—Lys—Gly—Gly—}\\
\phantom{xx}145\phantom{xxxxxxxxxxxx}150\\
\text{Gln—Asp—Ile—Thr—Asp—Phe—Thr—Met—Gln—Phe—}\\
\text{Val—Ser—Ser}
\end{array}$$

a) At least one amino acid residue selected from among Ala at the 1-position, Val at the 3-position, Arg at the 4-position, Ser at the 5-position, Cys at the 8-position, Arg at the 11-position, His at the 30-position, Cys at the 71-position, Lys at the 93-position, Lys at the 97-position, Arg at the 98-position, Phe at the 99-position, Lys at the 103-position, Trp at the 120-position, Tyr at the 121-position and Ser at the 153-position is deficient or replaced by another amino acid.

b) The amino acid sequence of Ala at the 1-position to Thr at the 9-position or at least one amino acid residue in this sequence is deficient (except that at least one amino acid residue selected from the group consisting of Ala at the 1-position, Val at the 3-position, Arg at the 4-position, Ser at the 5-position and Cys at the 8-position is deficient as stated in the requirement a)).

c) The amino acid sequence of Lys at the 103 position to Ser at the 153-position or at least one amino acid residue in this sequence is deficient (except that at least one amino acid residue selected from the group consisting of Lys at the 103-position, Trp at the 120-position, Tyr at the 121-position and Ser at the 153-position is deficient as stated in the requirement a)).

d) Met, or the amino acid sequence of Met at the 1'-position to Asp at the 116'-position represeted by the following formula (B), or a portion of the sequence of the formula (B) toward its C terminal is attached to the N terminal of the formula (A).

```
                          5'                        10'    Formula (B)
        Met—Ala—Glu—Val—Pro—Glu—Leu—Ala—Ser—Glu—

15'                        20'
        Met—Met—Ala—Tyr—Tyr—Ser—Gly—Asn—Glu—Asp—

25'                        30'
        Asp—Leu—Phe—Phe—Glu—Ala—Asp—Gly—Pro—Lys—

35'                        40'
        Gln—Met—Lys—Cys—Ser—Phe—Gln—Asp—Leu—Asp—

45'                        50'
        Leu—Cys—Pro—Leu—Asp—Gly—Gly—Ile—Gln—Leu—

55'                        60'
        Arg—Ile—Ser—Asp—His—His—Tyr—Ser—Lys—Gly—

65'                        70'
        Phe—Arg—Gln—Ala—Ala—Ser—Val—Val—Val—Ala—

75'                        80'
        Met—Asp—Lys—Leu—Arg—Lys—Met—Leu—Val—Pro—

85'                        90'
        Cys—Pro—Gln—Thr—Phe—Gln—Glu—Asn—Asp—Leu—

95'                       100'
        Ser—Thr—Phe—Phe—Pro—Phe—Ile—Phe—Glu—Glu—

105'                       110'
        Glu—Pro—Ile—Phe—Phe—Asp—Thr—Trp—Asp—Asn—

115'
        Glu—Ala—Tyr—Val—His—Asp
```

Amino acids and peptides are herein referred to by symbols according to the nomenclature or rules recommended by IUPAC and IUPAC-IUB or by symbols conventionally used in the art. The nucleic acids in base sequences are also similarly expressed. The amino acid number or position as used herein with reference to the polypeptide of the present invention is based on the amino acid sequence of IL-1β, i.e., the amino acid sequence of the formula (A), unless otherwise stated, even in the case where there is a deficiency or extension. However, the primed number or position is based on the amino acid sequence of the formula (B).

Aside from the above-mentioned reports, we discovered, as disclosed in our copending application Ser. No. 810776, a biologically active substance obtained in a homogeneous form and having an activity to inhibit the growth of tumor cells. We successfully confirmed the properties and the structure of the substance and also succeeded in developing and utilizing a gene for coding such substance.

In the copending application, we used a name "GIF" as an abbreviation of the biologically active substance thus discovered. However the substance also poseses LAF activity and so it seems to be IL-1 which is the term used to describe a group of factors. Further the biologically active substance includes a polypeptide represented by said formula (A). This polypeptide, however, may be properly called "IL-1β" rather than "GIF"; as usually so referred to in the art, e.g. in the above report by March et al [Nature, 315, 641 (1985)]. Accordingly throughout the present specification, the biologically active substance, GIF, disclosed in the copending application is described as included in the IL-1β and the derivatives thereof which are the polypeptides of the present invention.

Preferable derivatives of the IL-1β included in the present invention are polypeptides which fulfill at least one of the aforementioned requirements a) to c) or at least one of the requirements a) to c) together with the requirement d).

Preferred examples of IL-1β derivatives thereof, i.e. polypeptides, of the invention are as follows.

1) A polypeptide having the amino acid sequence of the formula (A) wherein at least Ala at the 1-position is deficient or replaced by another amino acid.

2) A polypeptide having the amino acid sequence of the formula (A) wherein at least Val at the 3-position is deficient or replaced by another amino acid.

3) A polypeptide having the amino acid sequence of the formula (A) wherein at least Arg at the 4-position is deficient or replaced by another amino acid.

4) A polypeptide having the amino acid sequence of the formula (A) wherein at least Ser at the 5-position is deficient or replaced by another amino acid.

5) A polypeptide having the amino acid sequence of the formula (A) wherein at least Cys at the 8-position is deficient or replaced by another amino acid.

6) A polypeptide having the amino acid sequence of the formula (A) wherein at least Arg at the 11-position is deficient or replaced by another amino acid.

7) A polypeptide having the amino acid sequence of the formula (A) wherein at least His at the 30-position is deficient or replaced by another amino acid.

8) A polypeptide having the amino acid sequence of the formula (A) wherein at least Cys at the 71-position is deficient or replaced by another amino acid.

9) A polypeptide having the amino acid sequence of the formula (A) wherein at least Lys at the 93-position is deficient or replaced by another amino acid.

10) A polypeptide having the amino acid sequence of the formula (A) wherein at least Lys at the 97-position is deficient or replaced by another amino acid.

11) A polypeptide having the amino acid sequence of the formula (A) wherein at least Arg at the 98-position is deficient or replaced by another amino acid.

12) A polypeptide having the amino acid sequence of the formula (A) wherein at least Phe at the 99-position is deficient or replaced by another amino acid.

13) A polypeptide having the amino acid sequence of the formula (A) wherein at least Lys at the 103-position is deficient or replaced by another amino acid.

14) A polypeptide having the amino acid sequence of the formula (A) wherein at least Trp at the 120-position is deficient or replaced by another amino acid.

15) A polypeptide having the amino acid sequence of the formula (A) wherein at least Tyr at the 121-position is deficient or replaced by another amino acid.

16) A polypeptide having the amino acid sequence of the formula (A) wherein at least Ser at the 153-position is deficient or replaced by another amino acid.

17) A polypeptide having the amino acid sequence of the formula (A) which is deficient at least in the amino acid sequence of Ala at the 1-position to Val at the 3-position, the amino acid sequence of Ala at the 1-position to Leu at the 6-position or the amino acid sequence of Ala at the 1-position to Thr at the 9-position.

18) A polypeptide having the amino acid sequence of the formula (A) which is deficient at least in the amino acid sequence of Val at the 151-position to Ser at the 153-position, the amino acid sequence of Gln at the 149-position to Ser at the 153-position, the amino acid sequence of Asp at the 145-position to Ser at the 153-position, the amino acid sequence of Gln at the 141-position to Ser at the 153-position, the amino acid sequence of Tyr at the 121-position to Ser at the 153-position, or the amino acid sequence of Lys at the 103-position to Ser at the 153-position.

19) A polypeptide having the amino acid sequence of the formula (A) the N terminal of which has attached thereto at least, Met, the amino acid sequence of Met at the 77'-position to Asp at the 116'-position, the amino acid sequence of Met at the 71'-position to Asp at the 116'-position, the amino acid sequence of Met at the 32'-position to Asp at the 116'-position or the amino acid sequence of Met at the 1'-position to Asp at the 116'-position of the formula (B).

While the IL-1β derivatives of the present invention include polypeptides having the amino acid sequence of IL-1β wherein the specific amino acid at the specific position is replaced by some other amino acid, the replacing amino acid may be any of α-amino acids constituting human proteins. However, Cys is likely to form a disulfide linkage intra- or inter-molecularly with its SH group. In view of this, the desirable amino acids are those other than Cys. Examples of more desirable amino acids are Gly for replacing the 4-position Arg; Ser or Ala for the 8-position Cys; Gln for the 11-position Arg; Tyr for the 30-position His; Ser, Ala or Val for the 71-position Cys; Leu for the 93-position Lys; Leu for the 98-position Arg; Gln for the 103-position Lys; Arg for the 120-position Trp; and Gln for the 121-position Tyr.

The IL-1β and derivatives thereof, i.e., poly-peptides of the invention have physiological activities such as LAF activity, activity to inhibit growth of tumor cells (GIF activity), i.e. activity to specifically inhibit growth of tumor cells, activity to promote production of various cytokines such as colony stimulating factor (CSF), interferon (IFN), interleukin-2 (IL-2) and interleukin-3 (IL-3), i.e. activity for example on human cells to greatly promote production of such cytokines, anti-inflammatory activity, activity for example to effectively inhibit progress of arthritis when administered to model animals with arthritis, and activity to prevent radiation injury, i.e. activity to prevent the possible living body disorders or serious side effects that would result from systemic radiation irradiation during bone marrow transplant, radiation irradiation for treatment of cancers and radiation accident. Accordingly, the polypeptides of the invention are very useful as immune system stimulants, for example, for promoting production of antibodies and enhancing the effect of vaccines, antitumor agents, agents for promoting production of cytokines such as CSF, IFN, IL-2 and IL-3, anti-inflammatory agents, agents for preventing radiation injury and other like medicinal agents.

The novel finding that the homogeneous IL-1β exhibits remarkable effect in treating an inflammation such as arthritis is surprising in view of the fact that IL-1 has been heretofore thought to induce an inflammation indirectly by acting as a mediator. The derivatives of the present invention are excellent in at least one of the activities specified above and/or in being low in toxicity and in side effect.

The IL-1β derivatives of the invention are effective especially as CSF production promoting agents. When administered to man, the derivative effectively cures granulocytopenia due to impaired formation of bone marrow resulting from chemotherapy or radiation therapy for cancers without entailing the likelihood of virus infections or antigen-antibody reaction (granulocytopenia curing drug). The CSF production promoting agent is usable also for preventing and curing various diseases owing to the activity of CSF the production of which is promoted by the agent as contemplated. For example, CSF acts to promote the function of granulocytes and macrophages (Lopez, A. F. et al., J. Immunol., 131, 2983 (1983); Handam, E. et al., same, 122, 1134 (1979) and Vadas, M. A. et al., same, 130, 795 (1983)), so that clinical application is expected of CSF for preventing and curing various infections. Similarly, the CSF production promoting agent is expected to be useful for clinical application.

In recent years, it is noted that compromised hosts with impaired biophylactic ability suffer from so-called opportunistic infections or terminal infections which occur when harmless pathogens become pathogenic. Clinically, these infections are attributable to pathogens including gram-negative bacilli such as Pseudomonas and Serratia, viruses such as Herpes simplex virus (HSV), Varicella-zoster virus (VZV) and Cytomegalovirus (CMV), fungi such as *candida albicans, Aspergillus fumigatus* and *nocardia asteroidea*, protozoa such as *Pneumocystis carinii* and *Toxoplasma gondii*, etc. Since the antibiotics presently used are not fully effective on the opportunistic infections, it is desired to conduct research on and develop new drugs for such infections. The present IL-1β derivatives are effective also for preventing and curing opportunistic infections which occur frequently especially when anticancer drugs are given. For example, they are useful for preventing and curing various infections which develop during chemotherapy of acute leukemia and bone marrow transplant, such as candidosis, cryptococcosis, aspergillosis, zygomycosis, chromomycosis, virus infections, Cytomegalovirus pneumonia and complications of these infections.

Besides the above-mentioned medicinal uses, the polypeptides of the present invention are very useful, for example, for preparing various useful cytokines in vitro from cell line, etc. because of their activity to promote production of cytokines. Attention has been directed to the preparation in natural-type cytokines, especially those which are glyco-proteins. The present polypeptide makes it possible to obtain useful cytokines efficiently in large quantities when used as a cytokine production inducting agent.

Among the IL-1β derivatives of the present invention, those exhibiting high activity are polypeptides of the formula (A) wherein at least Cys at the 71-position is deficient or replaced by some other amino acid, especially by an amino acid such as Ser, Ala, Val or the like.

Further the present derivatives of the formula (A) wherein at least Arg at the 4-position or at least Cys at the 8-position is deficient or replaced, and those which are at least deficient in at least one of the amino acids at the 103-position and the following positions have the feature of being low in activity to promote production of prostaglandin E (PGE) and therefore being diminished in side effects such as pyrogenic activity and being low in toxicity, and those wherein at least Arg at the 4-position is deficient or replaced have the feature of being higher in activity to promote production of CSF and in anti-inflammatory activity than in GIF activity and LAF activity.

Further the present derivatives having at least the above-specified amino acid(s) or polypeptide attached to the N terminal of the formula (A) also have the feature of being higher in activity to promote production of CSF and anti-inflammatory activity than in GIF activity and LAF activity, and are useful as medicinals, especially as oral drugs or suppositories, since they are low in toxicity and exhibit sustained activity.

Moreover, the present derivatives, particularly those wherein Cys at the 8-position and/or Cys at the 71-position are/is deficient or replaced are excellent in binding activity against the IL-1 receptor under various conditions. More preferable are those wherein the Cys at the 8- and/or 71-positions is replaced by Ser, Ala and/or Val.

Among the present derivatives wherein the molecule has a lower Cys content than in IL-1β or is free from Cys are more preferable in view of the possible unnecessary formation of an intra- or inter-molecular linkage due to the SH group of Cys.

The polypeptides of the present invention will be described below in detail with reference to a process for preparing the same.

The natural IL-1β included in the present invention is derived and produced by the culture of immunologically competent cells. The immunologically competent cells to be used are not limited specifically insofar as they are derived from human. Typical examples of immunologically competent cells are T-cells, B-cells, null cells, natural killer cells and like lymphocytes, mononuclear cells, macrophages and like mononuclear cells, and cell lines of such cells. Examples of lymphocytes are those removed from the spleen, tonsil, lung, blood, lymphnode or lympphoid tissues. Such immunologically competent cells can be separated off by a usual method, for example, by crushing a tissue containing the desired cells, filtering off extraneous matter and collecting the cells by centrifugation.

The various immunologically competent cells mentioned above are incubated using culture media which are generally used for a culture of such cells, preferably in the presence of an antitumor substance inducing agent. The natural IL-1β is obtained in the supernatant of the culture. Examples of useful culture media are CEM medium, CMRL-1066 medium, DM-160 medium, Eagle's MEM, autoclavable MEM, Fisher's medium, F-10 and F-12 media, L-15 medium, NCTC-109 medium, RPMI-1640 medium and the like. These media are used singly, or when desired, the medium may contain serum such as fetal bovine serum (FCS), or a serum component such as albumin. For incubation, immunologically competent cells are used preferably in an amount of about $1 \times 10^4$ to about $1 \times 10^7$ cells/ml based on the medium.

Antitumor substance inducing agents which can be incorporated into the cell suspension are those usually used, such as 12-O-tetradecanoylphorbol-13 acetate (TPA), phytohemagglutinin (PHA), concanavalin A (ConA), bacterial lipopolysaccharide (LPS), pokeweed mitogen (PWM), protein A (ProteinA) and the like. These agents are used in a concentration usually of 0.0001 to 0.1% (W/V %, same as hereinafter), preferably about 0.001%. Incubation can be conducted by a usual method, for example, by using $CO_2$ incubator. Incubation is carried out at about 30 to about 40° C., preferably about 37° C., for 1 to 5 days. After the incubation, the culture supernatant is separated off by a usual method, as by centrifugation.

The natural IL-1β of the present invention can be separated from the supernatant substantially by the same method as usually used for separating a protein-like substance from such a biological substance. For example, various procedures are usable utilizing the physical or chemical properties of the desired natural IL-1β. (See for example, "Biological Data Book II," pp. 1175–1259, 1st edition, 1st print, Jun. 23, 1980, published by Kabushiki Kaisha Tokyo Kagakudojin.) Examples of useful procedures are treatment with use of a usual protein precipitating agent, ultrafiltration, molecular sieve chromatography (gel filtration), liquid chromatography, centrifugation, electrophoresis, affinity chromatography, dialysis, and combinations of such procedures.

According to a preferred method of separation, the desired natural IL-1β is separated from the supernatant as partially purified. This partial purification is carried out, for example, by a treatment using as a protein precipitating agent an organic solvent such as acetone, methanol, ethanol, propanol or dimethylformamide (DMF), or an acidic reagent such as acetic acid, perchloric acid (PCA) or trichloroacetic acid (TCA), a treatment using a salting-out agent such as ammonium sulfate, sodium sulfate or sodium phosphate and/or ultrafiltration using a dialysis membrane, flat membrane, hollow fiber membrane or the like. These treatments are conducted in the same manner as usually done under usual conditions.

The roughly purified product thus obtained is then subjected to gel filtration, whereby a fraction exhibiting the activity of the desired substance is collected. Useful gel filtration agents are not limited specifically. Such agents include those made of dextran gel, polyacrylamide gel, agarose gel, polyacrylamide-agarose gel, cellulose or the like. Examples of useful agents commercially available are Sephadex G type, Sephadex LH type, Sepharose type, Sephacryl type (all products of Pharmacia), Cellofine (Chisso Corporation), Biogel P type, Biogel A type (both product of Bio-Rad Lab.), Ultroel (LKB), TSK-G type (product of Toyo Soda Mfg. Co., Ltd.), etc.

The gel filtration procedure gives a fraction of 10,000 to 25,000 in molecular weight exhibiting the activity of the substance of the invention.

The substance of the present invention can be isolated from the fraction as a homogeneous substance, for example, by subjecting the fraction to affinity chromatography with use of a hydroxyapatite column, ion exchange column chromatography as of the DEAE, CM or SP method, chromatofocusing method, reverse-phase high-performance liquid chromatography or the like, or to a combination of such methods.

The chromatofocusing method can be carried out by various known procedures. Usable as the column is, for example, PBE94 (Pharmacia) or the like, as the starting buffer, for example, imidazole-hydrochloric acid or the like, and the eluent, for example, the mixture of Polybuffer 74 (Pharmacia) and hydrochloric acid (pH 4.0) or the like.

The reverse-phase high-performance liquid chromatography can be conducted, for example, with $C_4$ Hi-Pore reverse-phase HPLC column (Bio-Rad Laboratories) or the like, using acetonitrile, trifluoroacetic acid (TFA), water of the like, or a mixture of such solvents as the eluent.

The IL-1β thus obtained is of the natural type (i.e., mature IL-1β) comprising as its constituent protein an amino acid sequence having the formula (A).

The polypeptides of the present invention can also be prepared, for example, by gene engineering techniques using a gene coding for the specific polypeptide of the invention, i.e., by incorporating the gene into a microorganism vector to effect replication, transcription and translation within the cell of the microorganism. This process is advantageous in that it is amenable to mass production.

Although the gene to be used in this process can be totally synthesized through chemical synthesis of nucleic acids by a usual method, for example, by the phosphite triester method (Nature, 310, 105 (1984)) or the like, it is convenient to utilize the gene coding for IL-1β or a precursor thereof. By a conventional method involving the above chemical synthesis, the gene is modified to a sequence of nucleic acids coding for the foregoing specific amino acid sequence, whereby the desired gene can be prepared easily.

We obtained the gene coding for IL-1β as disclosed in our U.S. Pat. No. 4,898,818 and succeeded in preparing IL-1β by gene engineering techniques using this gene. The series of gene engineering techniques employed will be described in the examples to follow.

Useful genes coding for IL-1β or a precursor thereof include those which are prepared from messenger RNA (hereinafter referred to as "mRNA") separated from human lymphoid cell series.

One of the transformant harboring plasmid containing said gene, i.e. cDNA of IL-1β precursor, is *Escherichia coli* χ1776/pGIF-α, which is deposited with deposition number FERM BP-948 in Fermentation Research Institute, Agency of Industrial Science and Technology since Dec. 12, 1985. Accordingly, the IL-1β gene can be prepared easily and advanatageously with use of this transformant.

The modified sequence of nucleic acids (bases) is prepared also by a known procedure, which executed according to the amino acid sequence of the desired polypeptide (Molecular Cloning Cold Spring Harbor Laboratory (1982)).

For example, cleavage, ligation, phosphorylation, etc. of DNA can be carried out by usual methods including treatment with enzymes such as restriction enzymes, DNA ligase, polynucleotidekinase and DNA polymerase, which are readily available as commercial products. The isolation and purification of the gene and nucleic acids included in these methods are conducted also in the usual manner, for example, by agarose gel electrophoresis. As will be described partially later, the gene obtained is replicated using a usual vector. The DNA fragment coding for the desired amino acid sequence and synthetic linkers can be prepared also easily by the above-mentioned chemical synthesis. The codon corresponding to the desired amino acid and to be used in the above methods is known and is selected as desired. A usual method may be used for this purpose, for example, in view of the frequency of use of the codon of the host to be used (Nucl. Acids Res., 9, 43–73 (1981)). Further for the modification of the codon in the nucleic acid sequence concerned, for example, site-specific mutagenesis (Proc. Natl. Acad. Sci., 81, 5662–5666 (1984)) can be resorted to as usually done which employs a primer comprising a synthetic oligonucleotide coding for the desired modified sequence about 15–30 mer.

The desired gene obtained by the foregoing process can be checked for its base sequence, for example, by the Maxam-Gilbert chemical modification method (Meth. Enzym., 65, 499–560 (1980)) or by the dideoxynucleotide chain termination method using M13 Phage (Messing, J. and Vieira, J., Gene, 19, 269–276 (1982)).

While the above process and procedures therefor will be described in the examples to follow, the process is not specifically limited; any process already known in the art may be used.

Thus, the present invention also provides a novel gene coding for a IL-1β derivative having the above-specified amino acid sequence.

The polypeptide of the present invention can be prepared by usual known gene recombination techniques using the gene. More specifically, it is produced by preparing a recombinant DNA which can express the gene in host cells, transforming the DNA into the host cell and incubating the transformant.

Useful host cells can be either eucaryotic or procaryotic cells. The eucaryotic cells include cells of vertebrate animals, yeasts, etc. Generally used as cells of vertebrate animals are, for example, COS cells which are cells of monkey (Y. Gluzman, Cell, 23, 175–182 (1981)), dihydrofolate reductase defective strain of Chinese hamster ovary cell (G. Urlaub and L.A., Chasin, Proc. Natl. Acad. Sci., U.S.A., 77, 4216–4220 (1980)), etc., while useful cells are not limited to these cells. Useful expression vectors of vertebrate cells are those having a promotor positioned upstream of the gene to be expressed, RNA splicing sites, polyadenylation site, transcription termination sequence, etc. These vectors may further have a replication origin when required. Examples of useful expression vectors include pSV2dhfr having an initial promotor of SV40 (S. Subramani, R. Mulligan and P. Berg, Mol. Cell. Biol., 1(9), 854–864), which is not limitative.

Yeasts are widely used as eucaryotic microorganisms, among which those of the genus Saccharomyces are generally usable. Examples of popular expression vectors of yeasts and like eucaryotic microorganisms include pAM82 having a promotor for acid phosphatase gene (A. Miyanohara et al., Proc. Natl. Acad. Sci., U.S.A., 80, 1–5 (1983), etc.

*E. coli* and *Bacillus subtilis* are generally used as procaryotic hosts. The present invention employs, for example plasmid vectors capable of replication in the host. To express the gene in the vector, expression plasmids can be used which have a promotor and SD (Shine-Dalgarno) base sequence at the upstream of the gene and ATG required for initiating protein synthesis. Widely used as host *E. coli* is *E. coli* K12 strain. pBR322 is a vector which is generally used. However, these are not limitative, and various known strains and vectors are usable. Examples of promoters usable are tryptophan promoter, $P_L$ promoter, lac promoter, lpp promoter, etc. The gene can be expressed with use of any of these promoters.

To describe the procedure with reference to the case wherein tryptophan promoter is used, vector pTM1(Fumio Imamoto, Taishya, Vol. 22, 289 (1985)) having tryptophan promoter and SD sequence is used as an expression vector. A gene coding for a desired polypeptide of this invention and having ATG when required is linked to the site of restriction enzyme ClaI which is present downstream from the SD sequence.

Incidentally, not only the direct expression system but a fusion protein expression system is also usable which employs, for example, β-galactosidase, β-lactamase or the like.

The expression vector thus obtained is introduced into host cells and thereby transformed by usual methods. For example, cells chiefly in the logarithmic growth phase are collected, treated with $CaCl_2$ and thereby made to readily accept DNA, whereupon the vector is introduced into the cell. With this method, $MgCl_2$ or RbCl can be made present conjointly with the vector so as to achieve an improved transformation efficiency, as is generally known. The cell can be converted to spheroplast or protoplast before transformation.

The desired transformant thus obtained can be incubated in the usual manner, whereby the desired polypeptide is produced and accumulated. The medium for the incubation may be any of those generally used for incubating cells, such as L medium, E medium, M9 medium, etc. Various carbon sources, nitrogen sources, inorganic salts, vitamins, etc. which are usually known can be admixed with these media. When the tryptophan promoter is used, M9 minimum medium, for example, is usable which has admixed therewith Casamino acid for effecting the action of the promotor. A chemical, such as indoleacrylic acid, for enhancing the action of tryptophan promoter can be added to the medium at a suitable stage of incubation.

The desired polypeptide of the present invention can be isolated from the resulting culture and purified by usual methods. It is desirable to extract the polypeptide from the host under a mild condition as by osmotic shock in order to maintained the higher-order structure thereof.

The above isolation or purification method is conducted substantially by the same method as already exemplified above.

In this way, the IL-1β and derivative thereof of the present invention can be obtained upon isolation.

The polypeptide of the invention, which has outstanding pharmacological activities as already stated, can be formulated into useful preparations for the aforementioned medicinal uses. Examples of such medicinal preparations include immunostimulators for producing antibodies, enhancing the effect of vaccines and curing immunodeficiency, antitumor agents, cytokine production promoters, anti-inflammatory agents, agents for preventing or curing radiation injury, agents for preventing or curing opportunistic infections, etc. These medicinal preparations are formulated usually in the form of pharmaceutical compositions comprising a pharmacologically effective amount of the present polypeptide and a suitable carrier. Examples of useful pharmaceutical carriers include excipients and diluents such as filler, extender, binder, wetting agent, disintegrator, surfactant, etc. which are generally used for preparing pharmaceuticals of the desired form to be used. The form of the pharmaceutical compositions is not specifically limited insofar as they effectively contain the present polypeptide but can be, for example, in the form of tablets, power, granules, pellets or like solid preparation. Usually, however, it is suitable that the composition be in the form of a solution, suspension, emulsion or the like for injection. Alternatively, such a composition can be a dry product which can be made liquid with addition of a suitable carrier before use. The pharmaceutical compositions mentioned above can be prepared by usual methods.

In accordance with the form of the pharmaceutical composition obtained, the composition is administered via a suitable route. For example, those for injection are given intravenously, intramuscularly, subcutaneously, intracuteneously, intraperitoneally or otherwise. The solid composition is given orally or intraintestinally. The amount of the active component of the composition and the dosage of the composition are suitably determined according to the method and form of administration, purpose of use, symptoms of the patient, etc. and are not definitely determinable. It is generally desirable to incorporate about 1 to about 80 wt. % of the active component into the pharmaceutical preparation and to give the preparation at a daily dose of about 0.1 $\mu$g to about 10 mg, calculated as the active component, for adults. The preparation need not always be given only once a day but can be given in three to four divided doses daily.

The present invention will be described in greater detail with reference to the following examples wherein IL-1$\beta$ and derivatives thereof of the invention were prepared.

In these examples, the following symbols are used for the polypeptide of the invention for a simplified description.

| Symbol (polypeptide No.) | IL-1$\beta$ and derivative |
|---|---|
| I | IL-1$\beta$ |
| II | [Gly$^4$]IL-1$\beta$ (IL-1$\beta$ wherein Arg at 4-position is replaced by Gly) |
| III | [Gln$^{11}$]IL-1$\beta$ (IL-1$\beta$ wherein Arg at 11-position is replaced by Gln) |
| IV | [Ser$^8$]IL-1$\beta$ (IL-1$\beta$ wherein Cys at 8-position is replaced by Ser) |
| V | [Ser$^8$, Ser$^{71}$]IL-1$\beta$ (IL-1$\beta$ wherein Cys at 8-position is replaced by Ser, and Cys at 71-position by Ser) |
| VI | [Ser$^{71}$]IL-1$\beta$ (IL-1$\beta$ wherein Cys at 71-position is replaced by Ser) |
| VII | [Gln$^{103}$]IL-1$\beta$ (IL-1$\beta$ wherein Lys at 103-position is replaced by Gln) |

-continued

| Symbol (polypeptide No.) | IL-1$\beta$ and derivative |
|---|---|
| VIII | IL-1$\beta$(1–140)-polypeptide (IL-1$\beta$ wherein the amino acids at 141-position et seq. are deficient) |
| IX | [Gln$^{121}$]IL-1$\beta$ (IL-1$\beta$ wherein Tyr at 121-position is replaced by Gln) |
| X | Met-IL-1$\beta$ (IL-1$\beta$ having Met attached to its N terminal) |
| XI | des-Ala$^1$-IL-1$\beta$ (IL-1$\beta$ wherein Ala at 1-position is deficient) |
| XII | [Leu$^{98}$]IL-1$\beta$ (IL-1$\beta$ wherein Arg at 98-position is replaced by Leu) |
| XIII | [Gly$^4$, Gln$^{11}$, Leu$^{98}$]IL-1$\beta$ (IL-1$\beta$ wherein Arg at 4-position is replaced by Gly, Arg at 11-position by Gln, and Arg at 98-position by Leu) |
| XIV | [Gly$^4$, Gln$^{11}$]IL-1$\beta$ (IL-1$\beta$ wherein Arg at 4-position is replaced by Gly, and Arg at 11-position by Gln) |
| XV | [Gly$^4$, Leu$^{98}$]IL-1$\beta$ (IL-1$\beta$ wherein Arg at 4-position is replaced by Gly, and Arg at 98-position by Leu) |
| XVI | [Gln$^{11}$, Leu$^{98}$]IL-1$\beta$ (IL-1$\beta$ wherein Arg at 11-position is replaced by Gln, and Arg at 98-position by Leu) |
| XVII | des-Arg$^4$-IL-1$\beta$ (IL-1$\beta$ wherein Arg at 4-position is deficient) |
| XVIII | des-Arg$^{11}$-IL-1$\beta$ (IL-1$\beta$ wherein Arg at 11-position is deficient) |
| XIX | des-Arg$^{98}$IL-1$\beta$ (IL-1$\beta$ wherein Arg at 98-position is deficient) |
| XX | [Ala$^8$]IL-1$\beta$ (IL-1$\beta$ wherein Cys at 8-position is replaced by Ala) |
| XXI | des-Cys$^8$-IL-1$\beta$ (IL-1$\beta$ wherein Cys at 8-position is deficient) |
| XXII | [Ala$^{71}$]IL-1$\beta$ (IL-1$\beta$ wherein Cys at 71-position is replaced by Ala) |
| XXIII | [Val$^{71}$]IL-1$\beta$ (IL-1$\beta$ wherein Cys at 71-position is replaced by Val) |
| XXIV | des-Cys$^{71}$-IL-1$\beta$ (IL-1$\beta$ wherein Cys at 71-position is deficient) |
| XXV | [Leu$^{93}$]IL-1$\beta$ (IL-1$\beta$ wherein Lys at 93-position is replaced by Leu) |
| XXVI | IL-1$\beta$-(1–144)-polypeptide (IL-1$\beta$ wherein the amino acids at 145-position et seq. are deficient) |
| XXVII | IL-1$\beta$-(1–148)-polypeptide (IL-1$\beta$ wherein the amino acids at 149-position et seq. are deficient) |
| XXVIII | [Arg$^{120}$]IL-1$\beta$ (IL-1$\beta$ wherein Trp at 120-position is replaced by Arg) |
| XXIX | [Tyr$^{30}$]IL-1$\beta$ (IL-1$\beta$ wherein His at 30-position is replaced by Tyr) |
| XXX | IL-1$\beta$-(1–102)-polypeptide (IL-1$\beta$ wherein the amino acids at 103-position et seq. are deficient) |
| XXXI | (77'–116')-IL-1$\beta$ (IL-1$\beta$ having attached to its N terminal 77'–116' position amino acid sequence of the formula (B)) |
| XXXII | (71'–116')-IL-1$\beta$ (IL-1$\beta$ having attached to its N terminal 71'–116' position amino acid sequence of the formula (B)) |
| XXXIII | (32'–116')-IL-1$\beta$ (IL-1$\beta$ having attached to its N terminal 32'–116' position amino acid sequence of the formula (B)) |
| XXXIV | (1'–116')-IL-1$\beta$ (IL-1$\beta$ having attached to its N terminal 1'–116' position amino acid sequence of the formula (B)) |
| XXXV | IL-1$\beta$-(1–120)-polypeptide (IL-1$\beta$ wherein the amino acids at 121-position et seq. are deficient) |
| XXXVI | [Ala$^8$, Ser$^{71}$]IL-1$\beta$ (IL-1$\beta$ wherein Cys at 8-position is replaced by Ala, and Cys at 71-position by Ser) |
| XXXVII | [Ala$^8$, Ala$^{71}$]IL-1$\beta$ (IL-1$\beta$ wherein Cys at 8-position is replaced by Ala, and Cys at 71-position by Ala) |
| XXXVIII | [Ala$^8$, Val$^{71}$]IL-1$\beta$ (IL-1$\beta$ wherein Cys at 8-position is replaced by Ala, and Cys at 71-position by Val) |

-continued

| Symbol (polypeptide No.) | IL-1β and derivative |
|---|---|
| XXXIX | IL-1β-(4–153)-polypeptide (IL-1β which is deficient in the amino acid sequence of Ala at 1-position to Val at 3-position) |
| XXXX | IL-1β-(7–153)-polypeptide (IL-1β which is deficient in the amino acid sequence of Ala at 1-position to Leu at 6-position) |
| XXXXI | IL-1β-(10–153)-polypeptide (IL-1β which is deficient in the amino acid sequence of Ala at 1-position to Thr at 9-position) |
| XXXXII | des-Val$^3$-IL-1β (IL-1β wherein Val at 3-position is deficient) |
| XXXXIII | des-Ser$^5$-IL-1β (IL-1β wherein Ser at 5-position is deficient) |
| XXXXIV | des-Lys$^{97}$-IL-1β (IL-1β wherein Lys at 97-position is deficient) |
| XXXXV | des-Phe$^{99}$-IL-1β (IL-1β wherein Phe at 99-position is deficient) |
| XXXXVI | IL-1β(1-150)-polypeptide (IL-1β wherein the amino acids at 151-position et seq. are deficient) |
| XXXXVII | des-Ser$^{153}$-IL-1β (IL-1β wherein Ser at 153-position is deficient) |
| XXXXVIII | Met-[Gly$^4$]IL-1β (IL-1β having Met attached to its N terminal and in which Arg at 4-position is replaced by Gly) |

In the following examples, physiological activities were determined by the following methods.

(1) Determination of IL-1 activity

Expressed in terms of LAF activity as measured by the method of J. J. Oppenhein et al. (J. Immunol., 116, 1466 (1976)) using thymus cells of a mouse of C3H/HeJ strain.

(2) Determination of GIF activity

Portions (0.1 ml) of the test solution diluted to varying concentrations were placed into the wells of 96-well microplate (Corning Co., Ltd.), 0.1 ml of Eagle's MEM suspension containing 10% FCS containing human melonoma cells A375 in an amount of 2×10$^4$ cells/ml was then placed into each well, and the cells were incubated in a CO$_2$ incubator (Napco Co., Ltd.) for 4 days. After the incubation, 0.05 ml of 0.05% Neutral Red (Wako Junyaku Co., Ltd.) was placed into each well, followed by incubation at 37° C. for 2 hours. After removing the supernatant, 0.3 ml of phosphoric acid buffer saline was gently poured into each well for washing. After removing the washing, 0.1 ml of mixture of sodium phosphate monobasic and ethanol in equal amounts was placed into each well, the plate was shaken for several minutes by a micromixer, and the amount of pigment taken into the cell was measured at an absorbance of 540 mμ using a photometer for 96-well microtitration plates (Titer check multiscane, Flow Lab.) to determine growth inhibition activity. The test group exhibiting 50% of the inhibition of cell growth of the control group, i.e., the test group which exhibited ½ the absorbance measured of the control group, was identified. The reciprocal of the number of times of dilution for the test group was taken as the GIF activity unit. Accordingly, when the GIF activity is 10 units, for example, the test solution, if diluted tenfold, still has activity to inhibit cell growth 50%.

BRIEF DESCRIPTION OF THE DRAWINGS

The following drawings are referred to in reference examples and examples.

FIGS. 21A–21D are graphs showing the influence of anti-polypeptide I serum (neutralized antibody) on the GIF activity derived from plasmid pcD-GIG-16 or on the GIF activity derived from plasmid pcD-GIF-207;

EXAMPLE 1

(I) Preparation of natural type IL-1β

Human peripheral blood lymphocytes were suspended in RPMI-1640 containing 2% FCS to prepare a cell suspension containing $1 \times 10^6$ cells/ml.

PHA-P (kidyney bean lectin, product of Difco), serving as an antitumor substance inducing agent, was added to the suspension at a concentration of 0.2%, followed by incubation in a $CO_2$ incubator (NAPCO5300, Napco Co., Ltd.) at 37° C. for 3 days. The culture was centrifuged (2000 g×10 min) to obtain a supernatant, which was thereafter used as the starting liquid.

The starting liquid was fractionated by the ammonium sulfate precipitation method (Nippon Seikagakukai edited, "Seikagaku Jikken Koza", Vol. 1, Tokyo Kagakudojin).

A precipitate having GIF activity was found in fractions having an ammonium sulfate concentration of 50 to 80%.

The precipitate was subjected to AcA54 (LKB) gel chromatography (80 cm×4.4 cm (diam.), mobile phase: phosphate buffer saline containing 0.02% polyethylene glycol (molecular weight 6000), flow rate 30 ml/hr) to obtain a fraction with a molecular weight of 10,000 to 25,000 which had GIF activity. This fraction exhibited no TNF, IFN or CSF activity.

Figure 1:
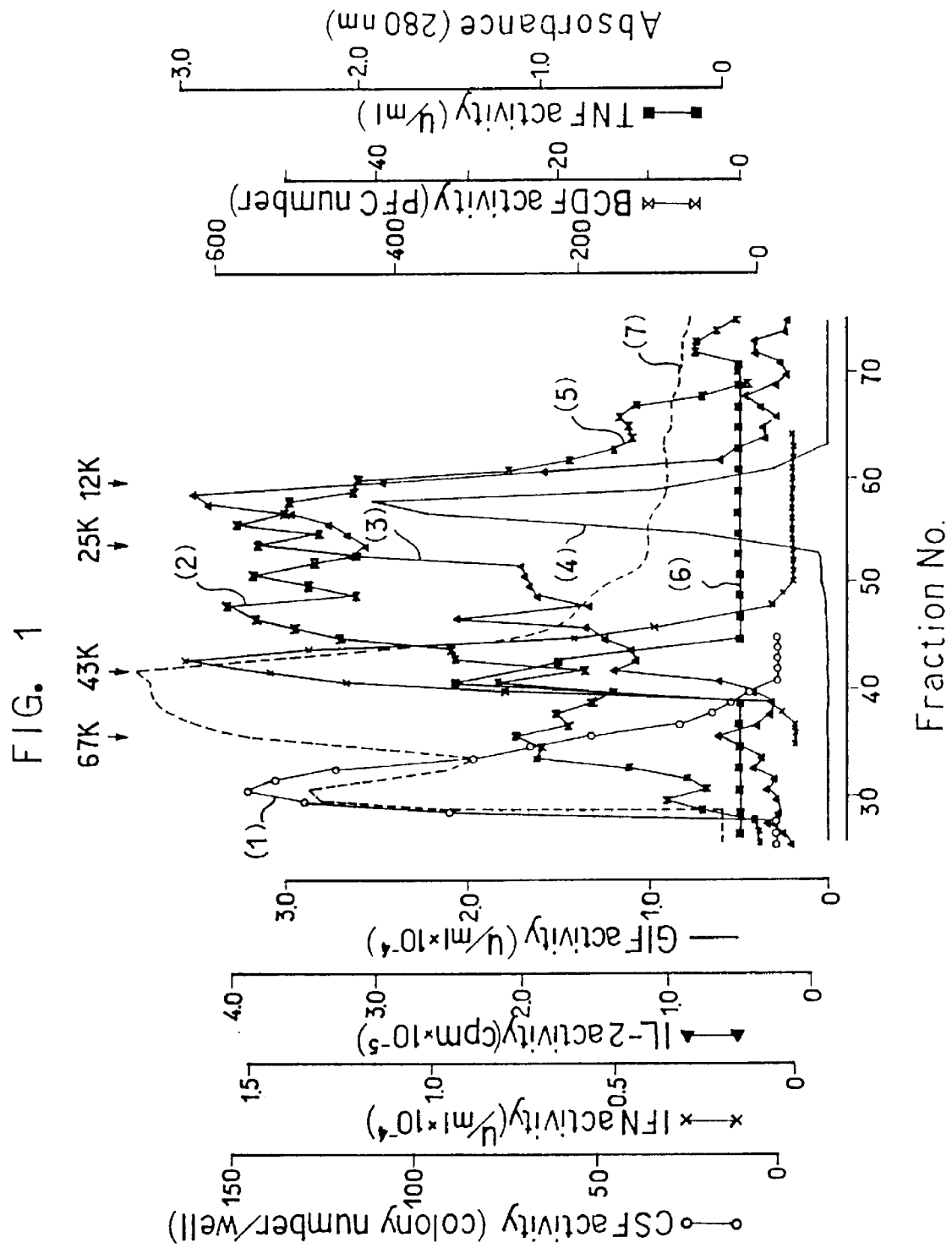
FIG. 1 shows the results of analysis obtained by subjecting the natural IL-1β prepared in Example 1 (I) to gel chromatography

FIG. 1 shows the results of gel chromatography. In the diagram, the fraction number is plotted as abscissa vs. the physiological activities and the absorbance with $OD_{280}$ as ordinate. Further for reference, the diagram shows the molecular weight corresponding to each fraction along with an arrow. In the diagram, CSF activity is represented by curve (1), IFN activity by curve (2), IL-2 activity by curve (3), GIF activity of the invention by curve (4), BCDF activity by curve (5), TNF activity by curve (6), and absorbance by curve (7).

Determination of activity

Physiological activities were determined by the following methods.

* GIF

According to the foregoing method.

* TNF

By the method of A. Khan et al. (Human Lymphokines, Academic Press, pp. 23–32, (1982)) using L929 cell strain.

* IFN

By the method of Sudo et al. (Tetsuo Sudo, Reiko Ohkubo, Masahiko Iizuka and Shigeyasu Kobayashi, 42nd Virus Yokusei Inshi Kenkyukai, 1982; Kohase, M., S. Kohno and S. Yamazaki (1982), Potency standardization of human IFN preparation for clinical trials. In the clinical potential for interferons, edt. by Kohno, p299, Tokyo University press.) using a system including human amino-derived FL cells and Sindbis virus.

* CSF (colony stimulating factor)

By the method of J.J. Farrar et al. (J. Immunol., 127 1983 (1981)) using myeloid cells of BALB/c mouse.

* LAF (lymphocyte activation factor)

By the method of J.J. Oppenhein et al. (J. Immunol., 116, 1466 (1976)) using thymocytes of C3H/HeJ mouse.

* IL-2 (interleukin-2)

By the method of S. Gillis and K.A. Smith (J. Immunol., 120, 2027 (1978)) using IL-2 dependent mouse T cells (CTLL2).

* BCDF (B-cell differentiation factor)

By the method of Kishimoto et al. (J Immunol., 127, 412 (1981) using CESS cell strain.

Next, the above fraction was chromatofocused using PBE94 (Pharmacia) gel. More specifically, the above fraction was fractionated using 0.025M imidazole-hydrochloric acid (pH4) as a starting buffer and Polybuffer 74-hydrochloric acid (pH 4) as an eluent. When the resulting fractions were checked for GIF activity, this activity was found to be present in the region of isoelectric points (PI) of 6.4 to 6.6.

Figure 2:
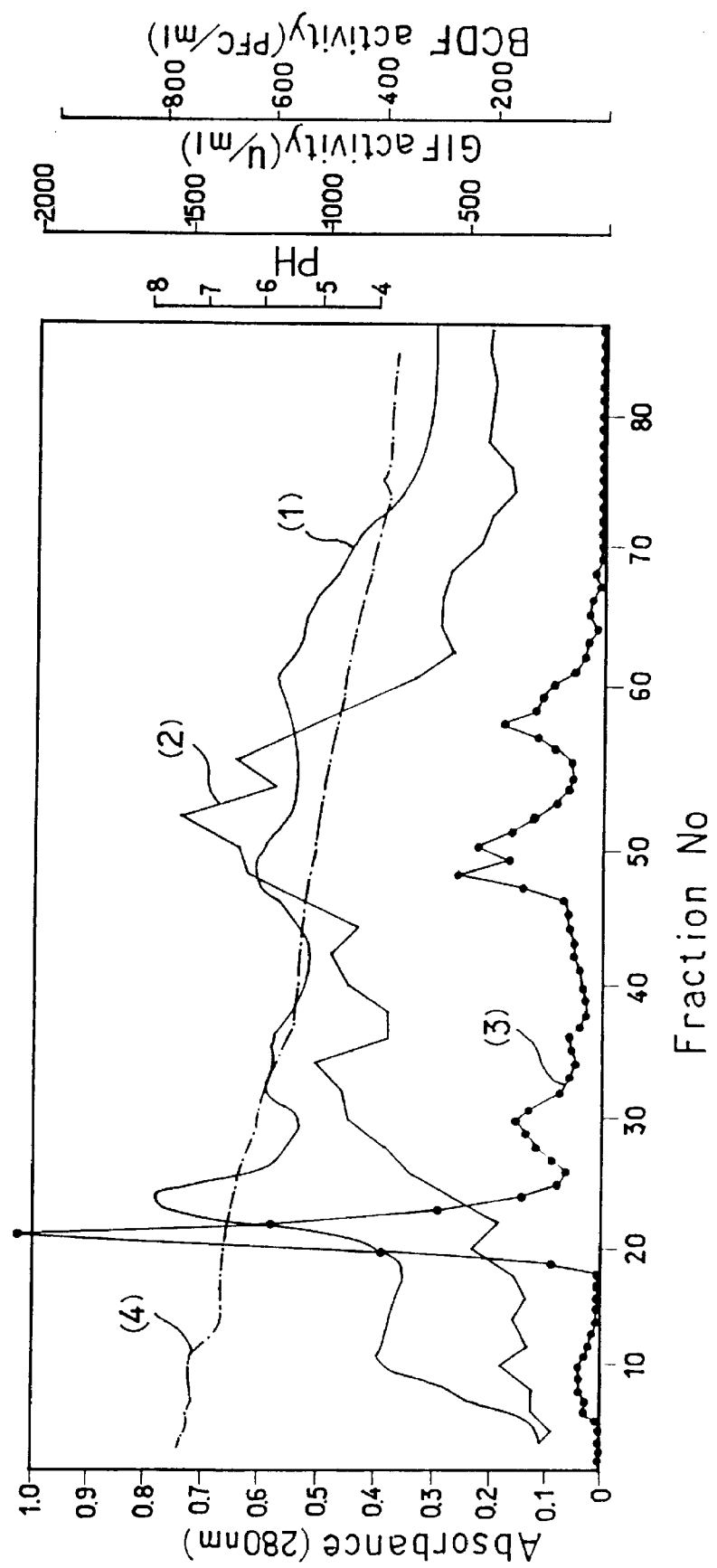
FIG. 2 shows the results of analysis obtained by subjecting said IL-1β to chromatofocusing.

FIG. 2 shows the results of chromatofocusing. In the diagram, the fraction number is plotted as abscissa. Plotted as ordinate are the absorbance with $OD_{280}$ (represented by curve (1)), BCDF activity (curve (2)), GIF activity of the invention (curve (3)) and pH (curve (4)).

The GIF-active fraction was further subjected to reverse-phase high-performance liquid chromatography ($C_4$ Highpore reverse-phase column (RP304), product of Bio-Rad, 250 mm×4.6 mm (diam.), mobile phase: A liquid=0.1% TFA and B liquid=0.1% TFA+70% acetonitrile, concentration gradient: change from 100% A liquid to 100% B liquid over a period of 80 min, flow rate: 1 ml/min) to obtain a fraction of 44±3% acetonitrile. This fraction exhibited no IL-2 activity. GIF activity did not agree with LAF activity.

Figure 3:
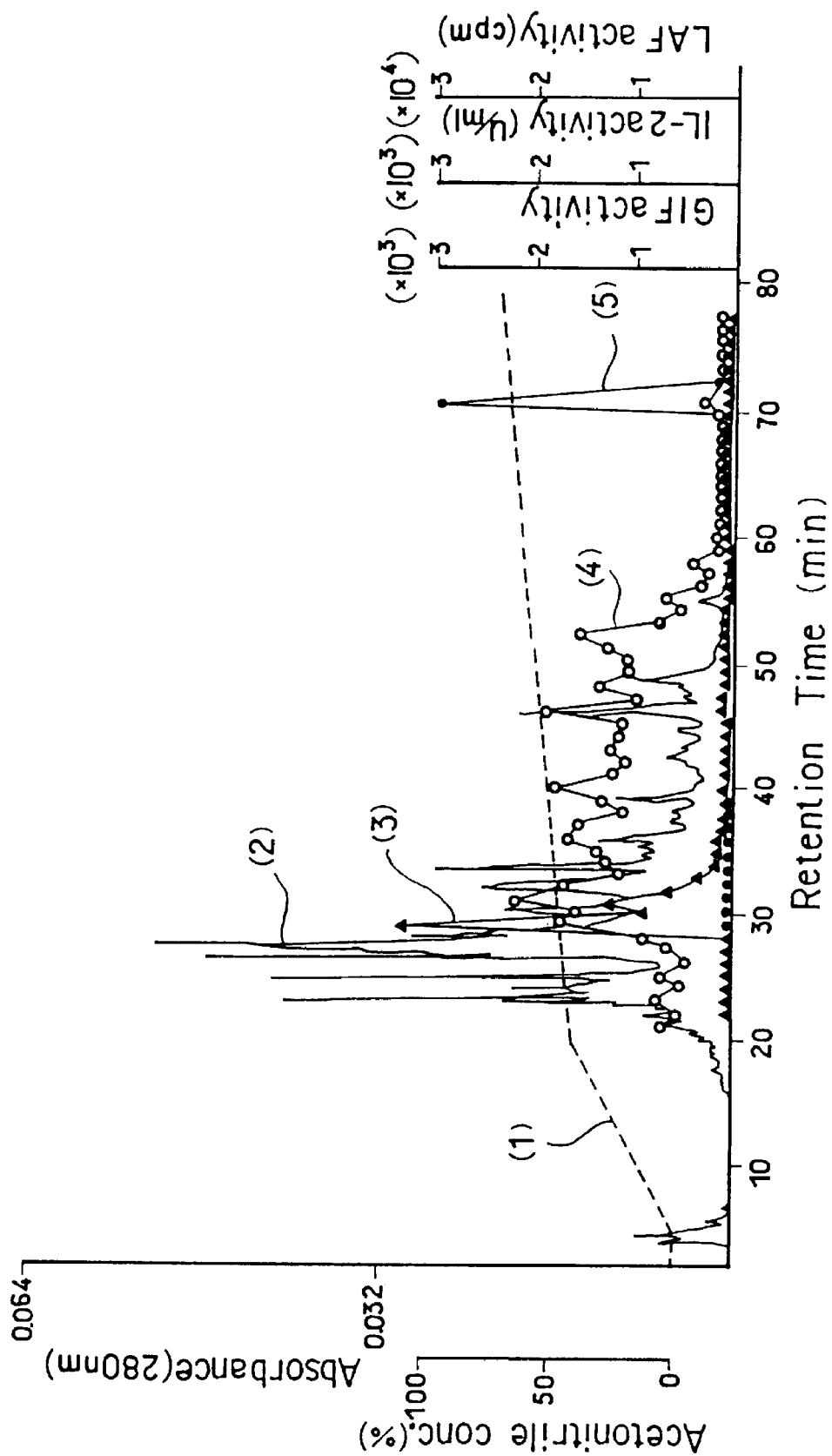
FIG. 3 shows the results of analysis obtained by subjecting said IL-1β to reverse-phase high-performance liquid chromatography.

FIG. 3 shows the results of the chromatographic analysis. In the diagram, the retention time is plotted as abscissa. Plotted as ordinate are the acetonitrile concentration represented by curve (1), absorbance of protein (OD 280) at 280 nm represented by curve (2), GIF activity of the invention represented by curve (3), LAF activity represented by curve (4) and IL-2 activity represented by curve (5).

Thus, the natural IL-1β of the present invention was isolated.

(II) Preparation of natural IL-1β

Human peripheral blood lymphocytes were added to RPMI-1640 medium containing 1% FCS, 0.1 µg/ml of indomethacine, 20 mM of N-2-hydroxyethylpiperazine-N'-2-ethanesulfonic acid (HEPES) and 10 µg/ml of LPS (Difco) to prepare a cell suspension having a concentration of $1 \times 10^6$ cells/ml.

The suspension was incubated in a $CO_2$ incubator (NAPCO 5300, Napco Co., Ltd.) at 37° C. for 20 to 24 hours, the culture was centrifuged (10000 r.p.m. ×30 min) to obtain 24300 ml of supernatant, and the supernatant was concentrated to 10 times the concentration using pericon membrane (molecular weight cut-off 10000, product of Millipore). The concentrate obtained will hereinafter be referred to as "starting liquid".

The starting liquid was fractionated by the ammonium sulfate precipitation method as in the procedure (I) with ice cooling. Fractions with an ammonium sulfate concentration of 50 to 80% were found to contain a GIF-active precipitate. The precipitate was dissolved in saline and then dialyzed with saline.

The resulting ammonium sulfate fraction was divided into four portions, and each portion was subjected to gel chromatography at 4° C. using Ultragel AcA54 (LKB) under the following conditions.

Column : 88 cm×4.4 cm (diam.)

Eluent : Phosphate buffer saline (PBS) containing 0.02% polyethylene glycol (molecular weight 6000) and 0.02% $NaN_3$ Flow rate : 30 ml/hour Fraction volume: 15/ml/30 min/tube With each portion, fractions (No.57 to No.65) with a molecular weight of about 10,000 to 25,000 had GIF activity, and the active fractions were collected.

The combined fraction was then concentrated with ice-cooling using YM-5 membrane (Amicon) using 50 mM sodium acetate (pH 5.5) as a solvent. The concentrate was filtered with Milex GV (0.22 µm, product of Millipore).

The concentrate specimen obtained was divided into two portions, and each portion was subjected to ion-exchange chromatography (CM-HPLC) using Gilson high permeation liquid chromatography system under the following conditions.

Column: IEX-535CM (6.0×150 mm, Toyo Soda Mfg. Co., Ltd.)

Eluent A: 50 mM sodium acetate (pH 5.5)

Eluent B: 50 mM sodium acetate (pH 5.5) containing 0.5M NaCl

Flow rate : 0.5 ml/min.

| Fraction volume: | Retention time: |
|---|---|
| 0–60 min | 2 ml/4 min/tube |
| 60–120 min | 0.5 ml/min/tube |
| 120–180 min | 2 ml/4 min/tube |

| Concentration gradient: | |
|---|---|
| Time (min) | % B |
| 0 | 0 |
| 40 | 0 |
| 120 | 20 |
| 140 | 100 |
| 165 | 100 |
| 170 | 0 |

The CM-HPLC procedure resulted in a GIF active fraction with a retention time of 90 to 91 minutes.

The active fraction (No.45) was then subjected to reverse-phase high-performance liquid chromatography under the following conditions.

Column : $C_4$ Highpore reverse-phase column (RP304, Bio-Rad, 250 mm×4.6 mm (diam.)

Eluents : A liquid=0.1% TFA B liquid=acetonitrile-1% TFA (9:1)

Flow rate : 1 ml/min.

| Chart speed: | Retention time: |
|---|---|
| 0–50 min | 5 min/cm |
| 50–80 min | 2 min/cm |

| Concentration gradient: | |
|---|---|
| Time (min) | % B |
| 0 | 0 |
| 5 | 0 |
| 15 | 20 |
| 75 | 45 |
| 80 | 100 |
| 85 | 100 |
| 90 | 0 |

Fraction volume: 2 ml/ min/tube

Figure 4:
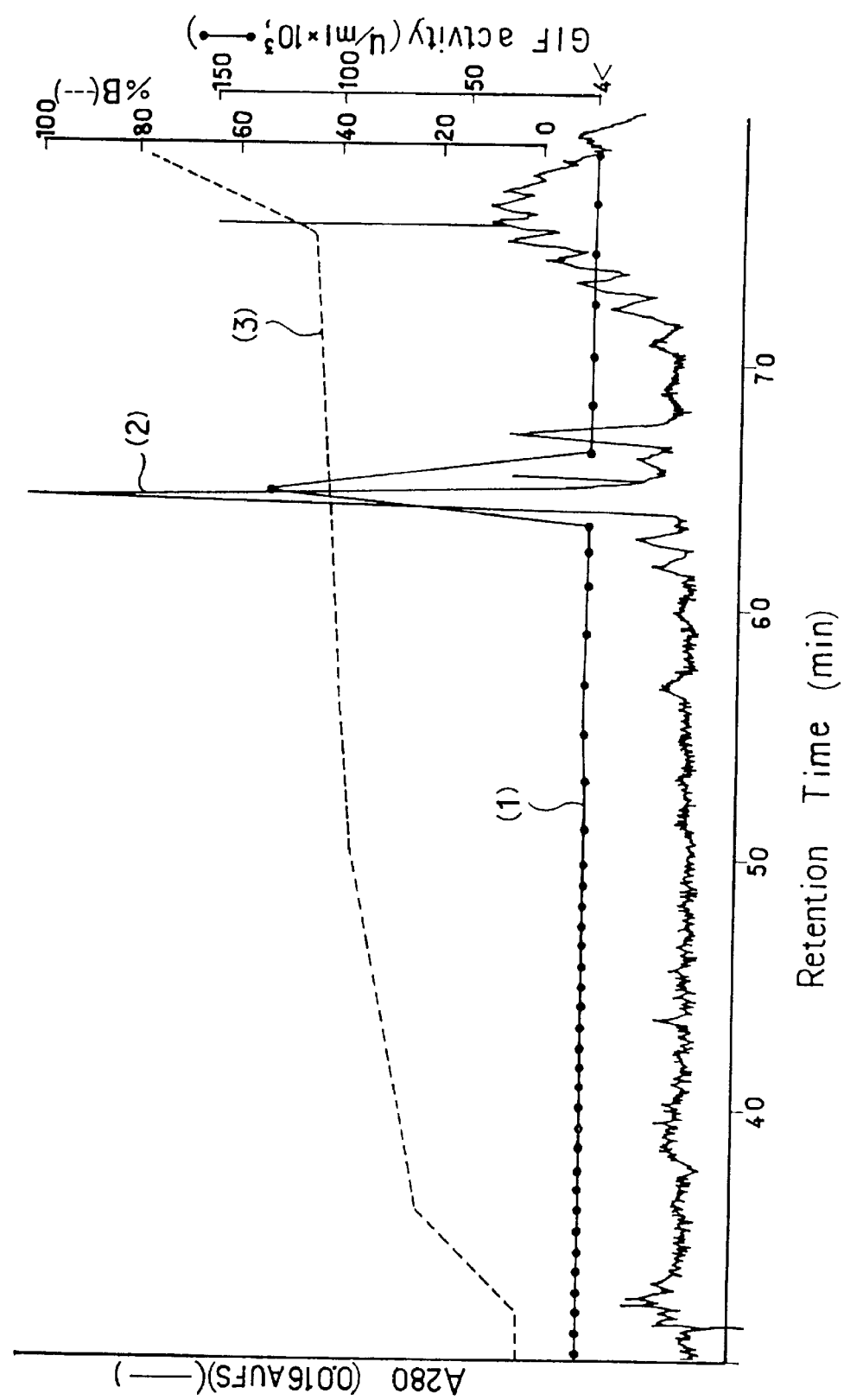
FIG. 4 shows the results of analysis obtained by subjecting the natural IL-1β prepared in Example 1 (II) to gel chromatography.

FIG. 4 shows the results of the chromatography. In diagram, plotted as abscissa is the retention time (min), and plotted as ordinate are the GIF activity curve 1), protein absorbance ($A_{280}$, curve 2) at 280 nm and concentration gradient (%B, curve 3) of the eluate.

A fraction with a retention time of 63.9 to 65.3 minutes exhibited a single protein absorbance peak matching that of GIF activity.

The specific activity was $2.1 \times 10^7$ GIF units/mg protein.
SDS polyacrylamide gel electrophoresis (SDS-PAGE)

The natural IL-1β obtained by the procedure (II) was subjected to SDS-PAGE by the method of Laemmli, U.K. (Nature, 277, 680 (1970)) under the following conditions.

Specimen: A 10 μl quantity of the GIF-active fraction was completely dried, then dissolved in Laemmli sample buffer (containing 2-mercapto ethanol in an amount of 1/20 the volume of the buffer) and treated at 100° C. for 4 minutes.

Gel : 15% Polyacrylamide gel 0.75 mm in thickness

Apparatus : PROTEAN, product of Bio-Rad

Electrophoresis: 20 mA constant current for 2 hours

Figure 5:
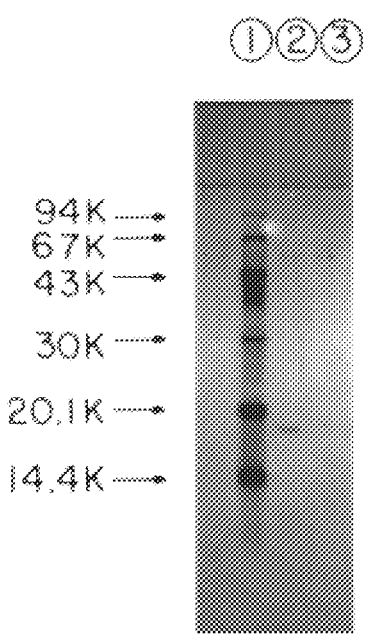
FIG. 5 shows the results of analysis obtained by subjecting said IL-1β to SDS-PAGE.

The gel resulting from the electrophoresis was dyed with Silver Stain Kit (Bio-Rad) with the results shown in FIG. 5.

With reference to FIG. 5, lane (1) resulted from the following molecular weight markers, lane (2) from the natural IL-1β specimen, and lane (3) from 10 μl of 0.1% TFA used in place of the GIF-active fraction and treated in the same manner as the specimen.

Molecular weight markers for lane (1)

| 94K: | Phosphorylase b |
|---|---|
| 67K: | Albumin |
| 43K: | Ovalbumin |
| 30K: | Carbonic anhydrase |
| 20.1K: | Trypsin inhibitor |
| 14.4K: | α-Lactoalubumin |

FIG. 5 shows that natural IL-1β is electrophoresed as a single band at a molecular weight of about 18K.
Isoelectroforcussing (IEF)

The natural IL-1β obtained by the procedure (II) was subjected to IEF using ampholine PAG plate (LKB) 3.5 to 9.5 in pH range and Model 1415 (Bio-Rad) under the following conditions.

Specimen: A 10 μl quantity of the GIF-active fraction as diluted fivefold with 25 mM sodium phosphate buffer (pH 7.4).

Electrode solutions: Anode solution=1M $H_3PO_4$ Cathode solution=1M NaOH

Figure 6:
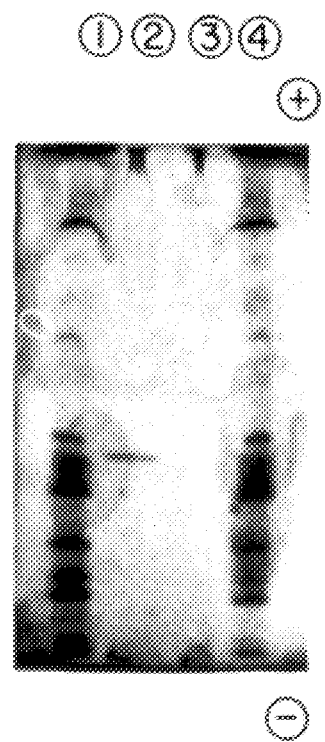
FIG. 6 shows the results of analysis obtained by subjecting said IL-1β to isoelectrofocusing.

Electrophoresis : With constant power of 1 W/cm gel width with cooling. (10° C.) for 90 minutes Staining: With silver stain Kit FIG. 6 shows the results of the electrophoresis. With reference to the drawing, lanes (1) and (4) resulted from 20 μl of molecular weight marker, lane (2) from 50 μl of the natural IL-1β specimen, and lane (3) from 50 μl of dilution prepared from 10 μl of 0.1% TFA in the same manner as the specimen with use of the buffer.

The gel resulting from the electrophoresis was sliced at a spacing of 5 mm or 2 mm, subjected to extraction with use of 1 ml of 10% FCS-added RPMI 1640 with shaking (for two days) and then checked for GIF activity. The isoelectric point was calculated from the pH measurement after the electrophoresis.

Figure 7:
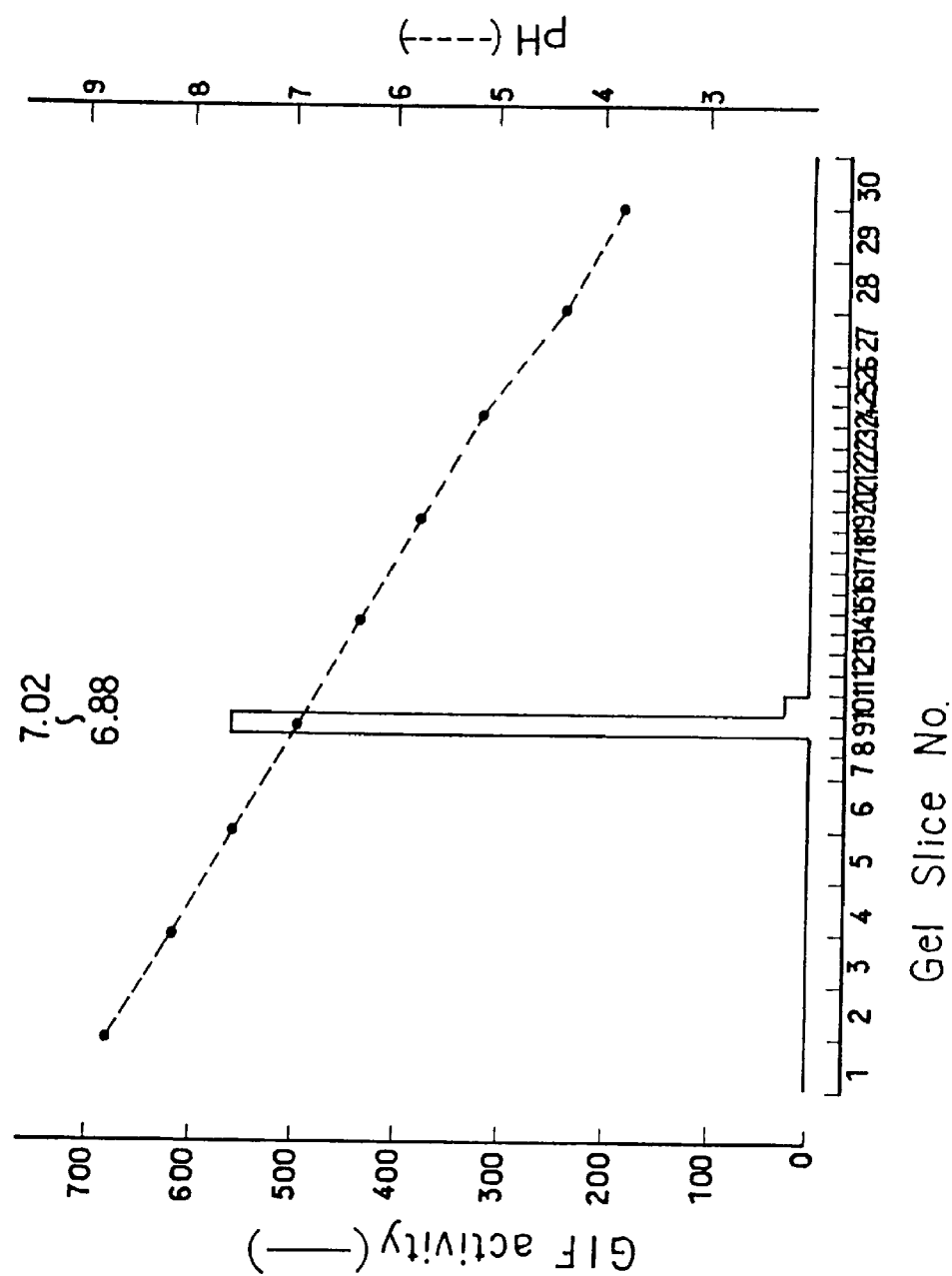
FIG. 7 is a graph showing the relationship given by the isoelectrofocussing between the GIF activity and the pH.

FIG. 7 shows the results. With reference to FIG. 7, the gel slice number is plotted as abscissa, vs. the pH gradient (represented by broken line) and GIF activity (solid line) as ordinate.

FIGS. 6 and 7 reveal that the natural IL-1β has an isoelectric point (PI) of 7.02 to 6.88 and appears as a single band at this position.
Amino acid composition The natural IL-1β obtained by the procedure (II) was hydrolyzed (with 4N methanesulfonic acid for 24 hours) and then analyzed by the o-phthalaldehyde (OPA) method using an amino acid analyzer (Hitachi Ltd.).

The analysis revealed that the natural IL-1β contains the following amino acids in the mole ratio given below based on Phe.

Under the above analysis conditions, Pro and Cys can not be determined. Further it is known that Ser and Thr decomposes generally about 5 to about 10% under the above conditions.

| Amino acid | Mole ratio |
|---|---|
| Asp and/or Asn | 17.6 |
| Ser | 12.1 |
| Thr | 5.7 |
| Glu and/or Gln | 23.1 |
| Gly | 8.1 |
| Ala | 5.2 |
| Val | 11.8 |
| Met | 5.6 |
| Ile | 4.8 |
| Leu | 15.4 |
| Tyr | 3.9 |
| Phe | (9) |
| Lys | 15.3 |
| His | 1.1 |
| Trp | 0.8 |
| Arg | 3.0 |

Amino acid sequence

The N-terminal amino acid sequence of the natural IL-1β obtained by the procedure (II) was determined by a gas-phase sequencer (Applied Bio System).

Consequently, the natural IL-1β was found to have the following sequence of 20 amino acids at the N terminal.

Ala—Pro—Val—Arg—Ser—Leu—Asn—

Cys—Thr—Leu—Arg—Asp—Ser—Gln—

Gln—Lys—Ser—Leu—Val—Met

The eighth amino acid from the N terminal was estimated to be Cys since it was not detected as PTH amino acid.

Physiological activity

The natural IL-1β obtained by the procedure (II) was tested for physiological activities, with the result that none of TNF, INF, CSF, IL-2 and BCDF activities were found. This indicates that the natural IL-1β distinctively differs from substances having such physiological activities. Natural IL-1β was also found to be extremely homogeneous.

Affinity tests for lectin columns

To check the natural IL-1β obtained by the procedures (I) and (II) for sugar chain specificity, the properties of these substances to bond to lectin columns were determined by affinity chromatography with use of the lectins given below, under the following conditions.

Specimen: 3624 units/0.06 mg/0.5 ml

Gel volume : 1 ml

Washing solution: PBS⁻-0.005% PEG (or 0.05M tris-0.15M NaCl, pH 8.7 for SJA)

Eluent : Solution of the sugar of Table 1 in the washing solution

Table 1 below shows the results. The lectins were purchased from E.Y. Laboratories.

TABLE 1

| Lection | |
|---|---|
| ConA | Concanavalin A |
| WGA | Wheat Germ Agglutinin |
| UEA-I | *Ulex europeus* Agglutinin |
| DBA | *Dolichos biflorus* Agglutinin |
| WFA | *Wistaria floribunda* Agglutinin |

TABLE 1-continued

| | |
|---|---|
| PNA | Peanut Agglutinin |
| SBA | Soybean Agglutinin |
| SJA | *Sophora japonica* Agglutinin |

| Lectin | Eluent |
|---|---|
| ConA | 0.1M α-Methylmannopyranoside |
| WGA | 0.2M N-Acetylglucosamine |
| UEA-I | 0.05M Fucose |
| DBA | 0.1M N-acetylgalactosamine |
| WFA | Same |
| PNA | 0.2M Glactose |
| SBA | Same |
| SJA | Same |

| Lectin | Sugar recognized |
|---|---|
| ConA | α-Man > α-Glc |
| WGA | GlcNAc β1–4GlcNAc |
| UAE-I | Same |
| DBA | α-GalNAc |
| WFA | Same |
| PNA | β-Gal |
| SBA | α-GalNAc > βGalNAc |
| SJA | β-GalNAc > βGal |

Figure 8:
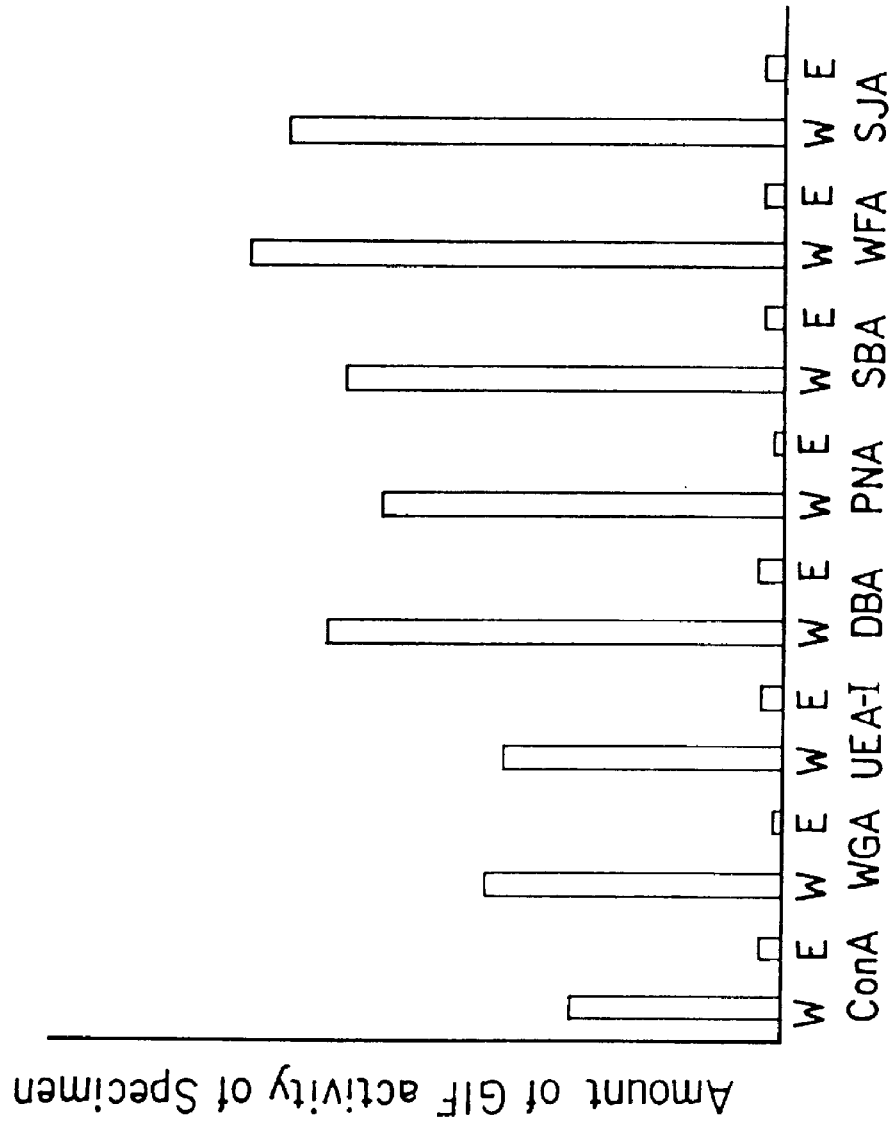
FIG. 8 is a graph showing the affinity of said IL-1β with lectin columns.

The results achieved by the natural IL-1β obtained by the procedure (I) are shown in FIG. 8. Plotted as ordinate in the diagram are the amount of activity contained in the fraction (W) passing through each lectin column without being adsorbed thereby, and the amount of activity contained in the fraction (E) adsorbed by the column and dissolved out by the eluent, the amounts of activity being in ratio relative to the GIF activity of the specimen which is taken as 100%. The fractions (W and E) from the columns are plotted as abscissa.

FIG. 8 shows the natural IL-1β has no affinity for any of the lectins. This indicates that these common sugar chains are not bonded to the natural IL-1β.

The natural IL-1β obtained by the procedure (II) produced the same results as shown in FIG. 8.

Stability

The natural IL-1β obtained by the procedures (I) and (II) was tested for stabilities as described below. The two substances were similar in the results achieved.

a. Temperature stability

The natural IL-1β was treated under the conditions given in Table 2 and checked for stability to temperature. The gel filtration fraction (3503 units/ml) was incubated at the listed temperature and thereafter checked for remaining GIF activity (%) relative to the control group. Table 2 also shows the results.

TABLE 2

| Treating conditions | Remaining GIF activity (%) |
|---|---|
| 37° C., 1 hr. | 97 |
| 56° C., 30 min. | 0 |
| 70° C., 30 min. | 0 |
| 80° C., 30 min. | 0 |
| 4° C., 1 hr. | 100 (Control) | b. pH stability

The natural IL-1β was treated similarly under the conditions given in Table 3 (at constant temperature of 4° C.) and then checked for stability to pH similarly. Table 3 also shows the results.

TABLE 3

| Treating conditions | Remaining GIF activity (%) |
| --- | --- |
| pH 7.4, 5 hr. | 100 (Control) |
| pH 2.0, 5 hr. | 60 |
| pH 4.0, 5 hr. | 80 |
| pH 6.0, 5 hr. | 90 |
| pH 8.0, 5 hr. | 95 |
| pH 9.5, 5 hr. | 75 | c. Stability to proteases

In the same manner as above a., the natural IL-1β was checked for stability to proteases under the conditions given in Table 4 below. Trypsin Type III (12700 BAEE units/mg protein, product of Sigma) was used at a concentration of 1 mg/ml as trypsin. The pronase (45000 p.u.k/g protein) produced by Kaken Kagaku Co., Ltd. was used at a concentration of 1 mg/ml as pronase.

TABLE 4

| Treating conditions | Remaining GIF activity (%) |
| --- | --- |
| With phosphate buffered saline (pH 7.4) at 37° C. for 2 hours | 100 (Control) |
| With trypsin at 37° C. for 2 hours | 0 |
| With pronase at 37° C. for 2 hours | 0 |

Table 4 indicates that the natural IL-1β inactivated when treated with trypsin as well as with pronase.

Figure 9:
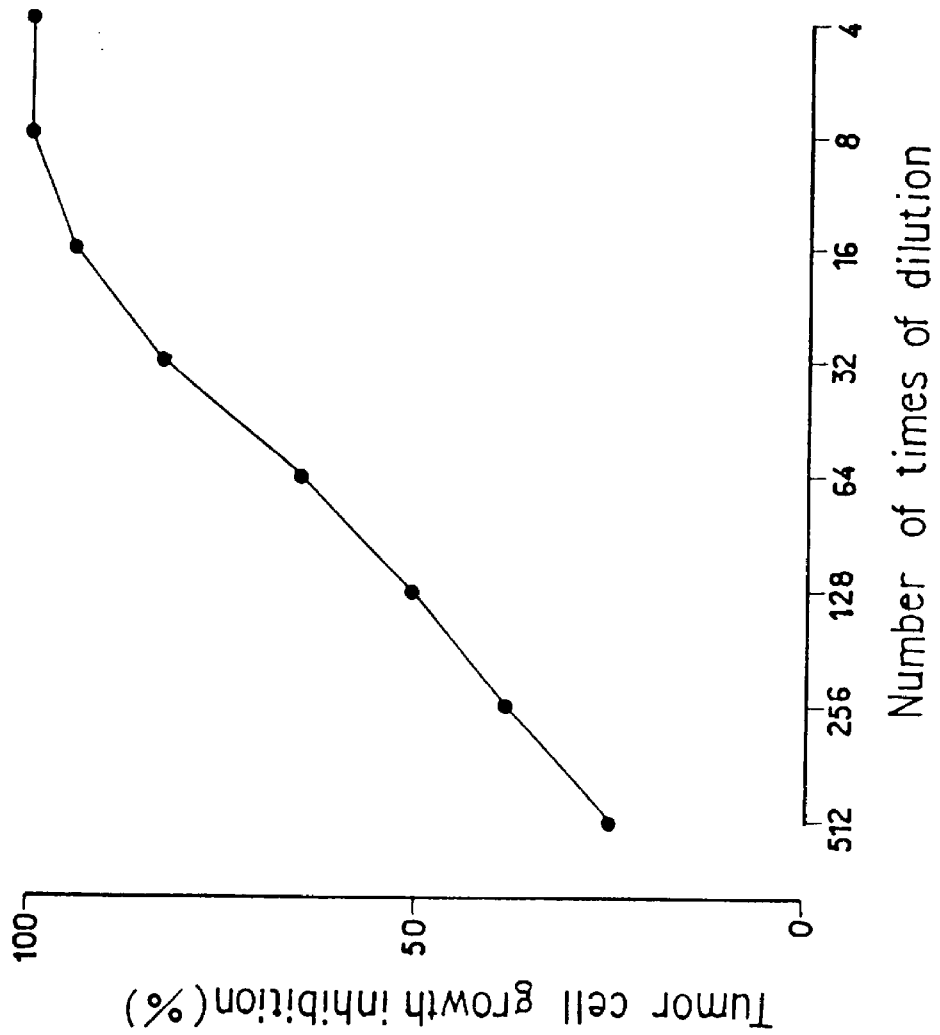
FIG. 9 is a graph showing the GIF activity as determined when said IL-1β was diluted in varying concentrations.

Dose-response curve of GIF activity (a) The natural IL-1β specimen (144.6 GIF units/ml, 723 ng/ml in protein concentration) obtained by the procedure (I) was used for determining dose-response curve of GIF activity at varying times of dilution. FIG. 9 shows the results. In the diagram, the number of times of dilution is plotted as abscissa, and the percent tumor cell growth inhibition (GIF activity) as the ordinate.

FIG. 9 shows that the natural IL-1β achieves about 50% activity at a dose of several tens of ng/ml.

(b) The antitumor activity of the natural IL-1β obtained by the procedure (II) on various cancer cells was determined by the following colony inhibition test and growth inhibition test.

Colony inhibition test

Into the wells of 12-well tissue culture plate (product of Coster) was placed a suspension of test cancer cells in 10% FCS containing RPMI 1640 at a of $2 \times 10^2$ to $5 \times 10^2$ cells/well (500 μl/well).

The natural IL-1β specimen was placed into each well to a final concentration of 1.6 to 1000 GIF units/ml. Further a control was prepared without using any IL-1β specimen.

The suspension was incubated in the presence of 5% carbon dioxide gas for 1 week. The medium was thereafter removed by an aspirator, each well was washed with PBS containing $CaCl_2$ (PBS⁺) twice, and the resulting colonies were fixed with 100% methanol, dyed by giemsa staining and then counted.

Percent colony inhibition was calculated from the following equation.

$$\text{Colony inhibition (\%)} = \left(1 - \frac{\text{Number of colonies in specimen}}{\text{Number of colonies in control}}\right) \times 100$$

Figure 10:
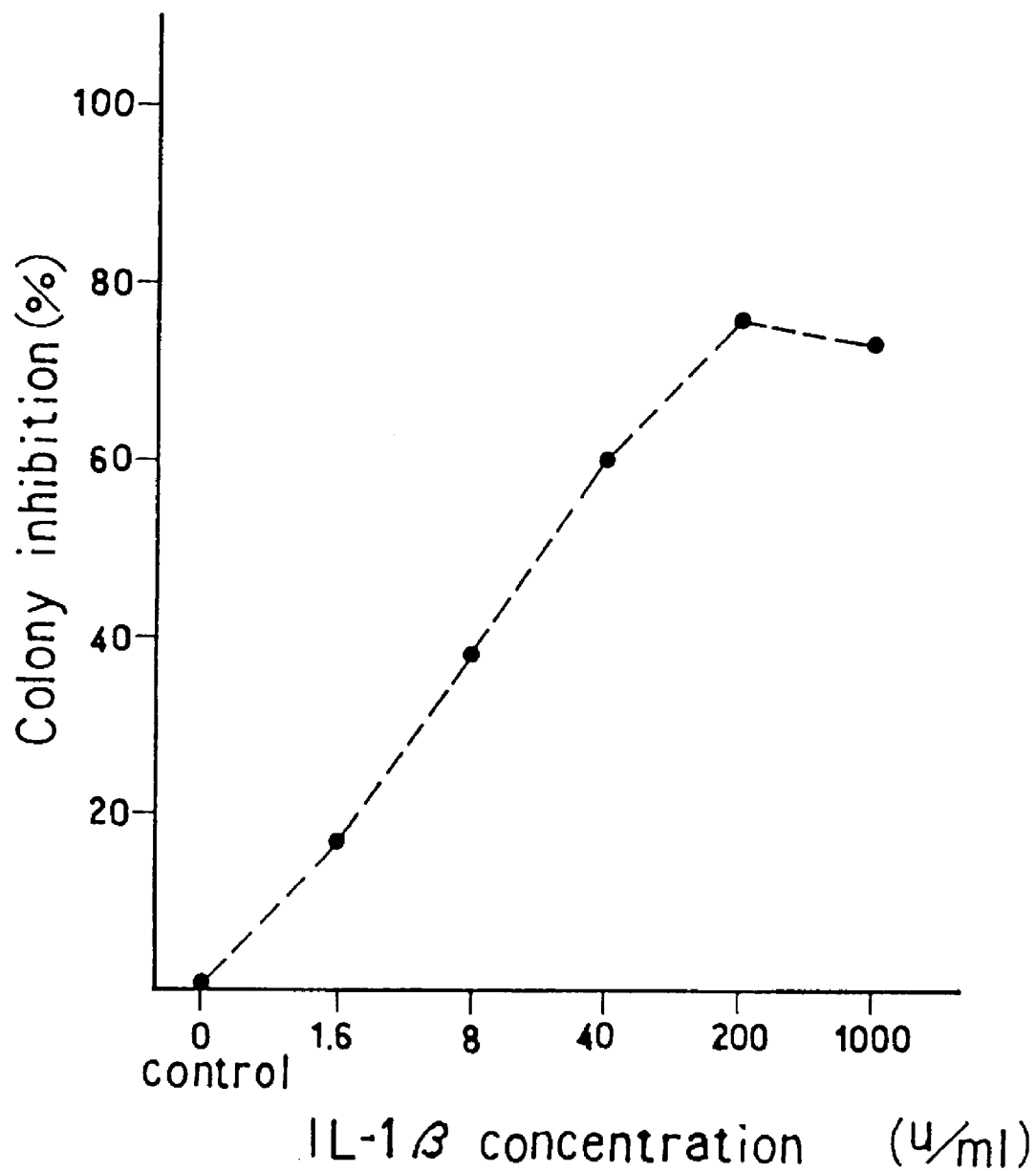
FIG. 10 shows the results obtained by testing said IL-1β for inhibition of tumor cell colony.

FIG. 10 shows the results achieved with use of A-549 (human lung cancer cells, ATCC CCL185). In the drawing, the natural IL-1β concentration (GIF units/ml) is plotted as abscissa vs. the percent colony inhibition as ordinate.

Growth inhibition test

Into the wells of 96-well tissue culture plate (product of Corning) was placed a suspension of test cancer cells in 10% FCS containing RPMI 1640 at a concentration of $2 \times 10^3$ to $5 \times 10^3$ cells/well (100 μl/well).

The natural IL-1β specimen was placed into each well in an amount of 100 μl at a final concentration of 1 to 10000 GIF units/ml medium. A control was prepared without using any IL-1β specimen.

The cells were incubated at 37° C. in the presence of 5% carbon dioxide gas for 4 to 5 days, 50 μl of 0.05% Neutral Red was thereafter added to each well, and the cells were further incubated at 37° C. in the presence of 5% carbon dioxide gas for 1 hour. Each well was then washed with PBS not containing $CaCl_2$ (PBS⁻), 100 μl of a pigment extraction buffer was placed into the well, and the absorbance (O.D.) of the well was measured at 540 nm.

Percent growth inhibition was calculated from the following equation.

$$\text{Percent growth inhibition} = \left(1 - \frac{\text{O.D. of specimen}}{\text{O.D. of control}}\right) \times 100$$

Figure 11:
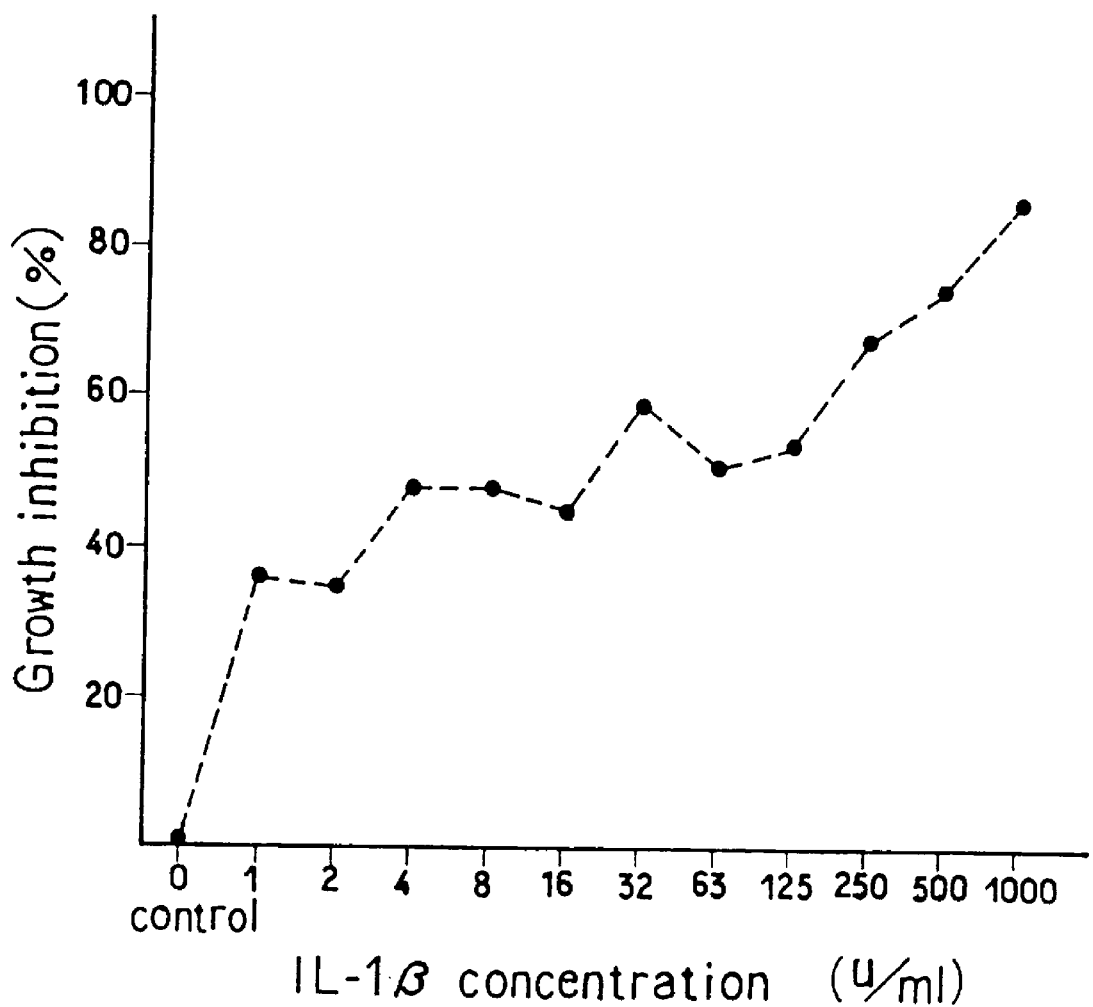
FIGS. 11 and 12 are graphs showing the results obtained by testing said IL-1β for inhibition of cancer cell growth.
Figure 12:
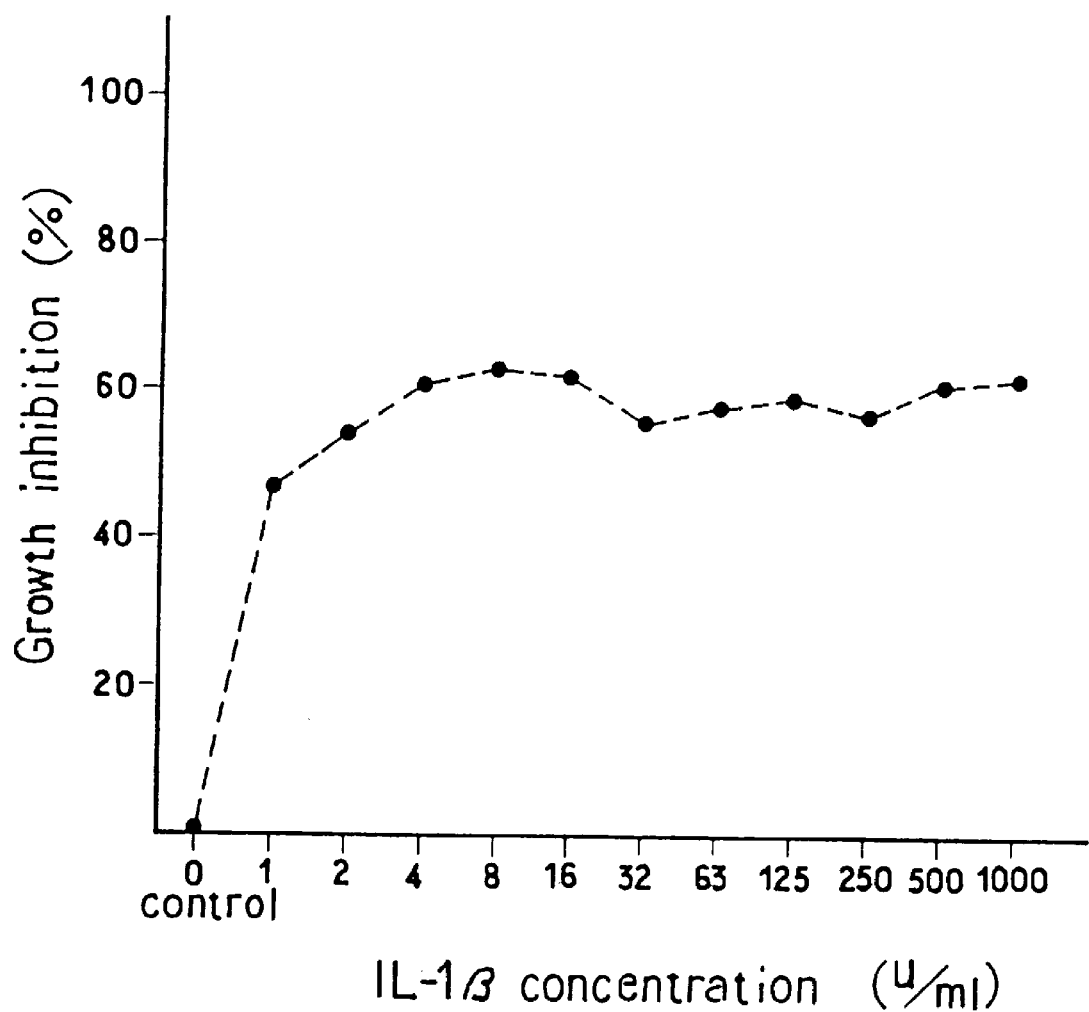

The results achieved by ACHN (human renal adenocarcinoma, ATCC CRL1611) are shown in FIG. 11, and those achieved by SK-BR-3 (human breast adenocarcinoma, ATCC HTB30) are shown in FIG. 12. In these diagrams, the natural IL-1β concentration (GIF units/ml) is plotted as abscissa vs. the percent growth inhibition as ordinate.

Determination of primary structure of natural IL-1β

(1) Human peripheral blood was collected, from which $1.9 \times 10^{10}$ lymphocytes were obtained by the F-icoll-Hypaque density gradient centrifugation method (Eur. J.Immunol. 4, 808 (1974)).

A quantity of the lymphocytes were suspended in RPMI 1640 medium containing 5% of human serum at a concentration of $4 \times 10^8$ cells/ml. The suspension was dividedly placed into Petri dishes, 9 cm in diameter, and the cells were incubated in the presence of 5% carbon dioxide gas at 37° C. for one hour. The cells which were not adhered on the bottom of each dish were removed, and were stimulated with RPMI 1640 medium containing 10% FCS, 0.5 ng/ml of TPA (product of Sigma) and 10 μg/ml of LPS (product of Difco). After incubating the cells in 5% carbon dioxide gas at 37° C. for 4 hours, $9 \times 10^8$ adhered lymphocytes were obtained using PBS and 0.02% EDTA.

The cells adhered on the bottoms of the dishes were stimulated with 10 μg/ml of LPS under the same incubation conditions as above. The supernatant of the culture was thereafter checked for GIF activity at a time interval.

Figure 13:
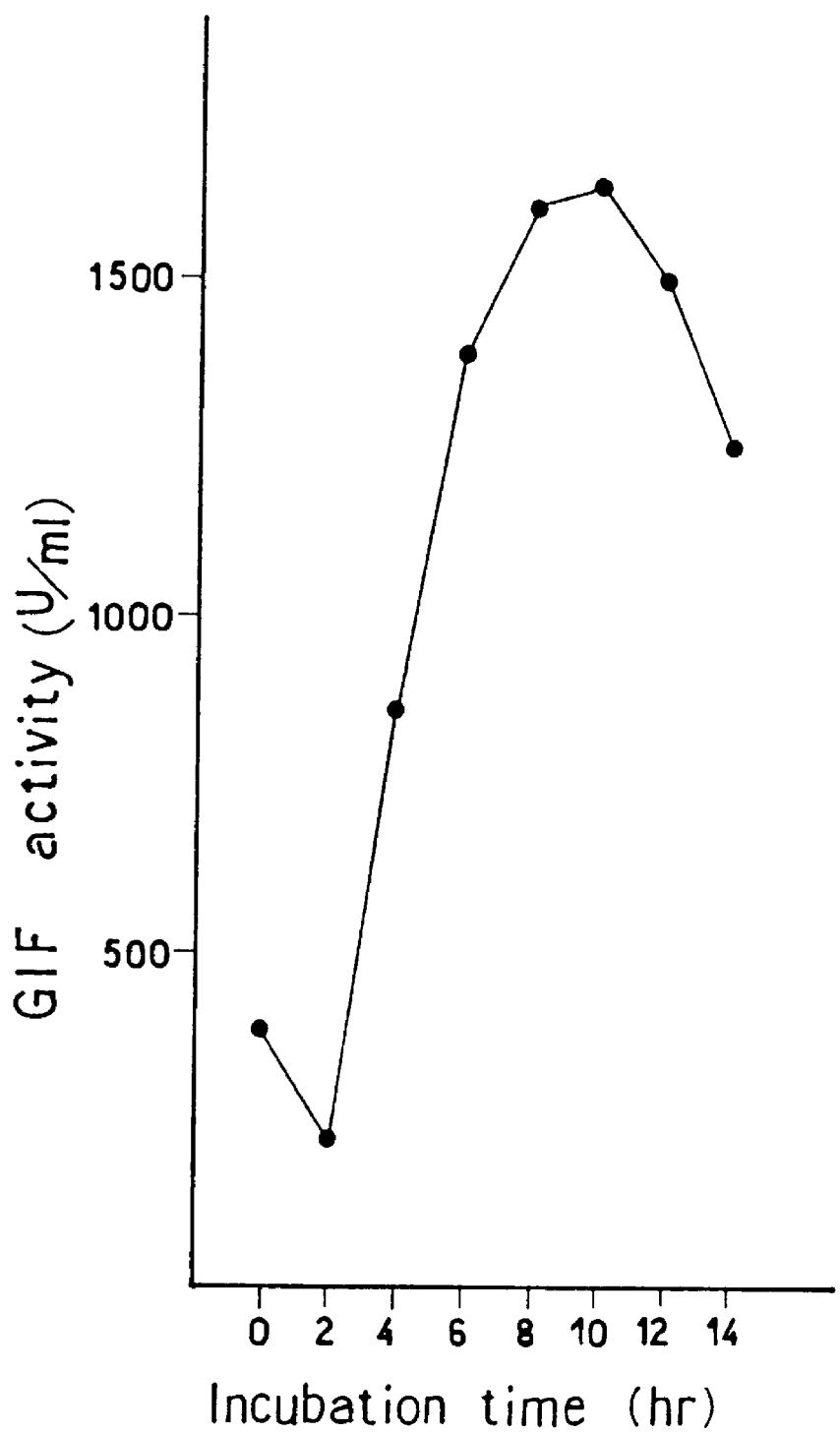
FIG. 13 shows the relationship between the incubation time of lymphocytes and the GIF activity of supernatant.

FIG. 13 shows the results. In the diagram, the incubation time (hours) is plotted as abscissa vs. the GIF activity (units/ml) as ordinate.

FIG. 13 indicates that the culture supernatant started to exhibit the GIF activity 4 hours after the stimulation with LPS and that mRNA producing IL-1β protein can be prepared from human adhered cells obtained 4 hours after the stimulation.

(2) Human adhered lymphocytes ($9 \times 10^8$ cells) induced over a period of 4 hours with 0.5 ng/ml of TPA and 10 μg/ml of LPS by the procedure (1) were dissolved in 30 ml of 6M guanidine thiocyanate solution (6M guanidine isothiocyanate, 5 mM sodium citrate (pH 7.0), 0.1M 2-mercapto ethanol and 0.5% Sarkosyl), and the DNA was thereafter sheared with a 50-ml syringe barrel having G18G injection needle. A 12 g quantity of cesium chloride (CsCl) was completely dissolved in the solution. Portions (6.4 ml each) of the solution were superposed on 4 ml of 5.7M CsCl (5.7M CsCl-0.1M EDTA), and the combined layer was centrifuged by Beckman SW-40 Ti rotor at 31500 r.p.m. and 25° C. for 20 hours. The RNA pellet sediment was washed with 70% ethanol and dissolved in TE solution (10 mM tris-HCl (pH 7.5), 1 mM EDTA). To the solution were added 3M sodium acetate (pH 5.2) and ethanol in amounts of ⅒ and 2.2 times the amount of the solution, respectively, and the mixture was allowed to stand at −70° C. for one hour. The mixture was then centrifuged at 15000 r.p.m. and 4° C. for 20 minutes to collect the RNA, which was then dissolved in TE solution.

In this way, 250 μg of total RNA was prepared from about $9 \times 10^8$ adhered lymphocytes.

To obtain mRNA from the RNA, the RNA was subjected to column chromatography using oligo(dT)-cellulose (Collaborative Research Inc.). For adsorption, a solution of 10 mM tris-HCl (pH 7.5), 0.5M NaCl and 1 mM EDTA was used, and the column was washed with the same solution. The RNA was eluted with 10 mM tris-HCl (pH 7.5) and 1 mM EDTA.

Consequently 17.5 μg of mRNA was obtained.

(3) From the mRNA obtained by the procedure (2), cDNA was synthesized in vitro, and recombinant DNA was prepared using Okayama-Berg plasmid vector (Okayama, H. and Berg, P., Mol. Cell. Biol., 2, 161 (1982)) and was transformed in *E. coli* to obtain cDNA library. The procedures given below were followed.

(3-1) Preparation of vector primer and linker DNA

DNA (400 μg) of pBR322-SV40 (0.71–0.86) was digested with 700 units of KpnI (NEB) at 37° C. for 5 hours. The reaction was terminated with a mixture of 40μl of 0.25M EDTA (pH 8.0) and 20 μl of 10% SDS. The reaction mixture was subjected to extraction with the same volume of phenol-chloroform (1:1). DNA was precipitated using ethanol, followed by centrifugation and washing with 70% ethanol to cellect DNA. The DNA obtained was dissolved in 200 μl of mixture of 140 mM sodium cacodylate, 30 mM tris-HCl (pH 6.8), 1 mM $CoCl_2$, 0.1 mM DTT and 0.25 mM dTTP (containing 0.5 μCi of α-$^{32}$P-dTTP). The solution was treated with 400 units of terminal transferase (TTase, PL) for 30 minutes to elongate the dT chain. The reaction was terminated with 20 μl of 0.25M EDTA and 10 μl of 10% SDS, followed by extraction with phenol-chloroform 4 times. DNA was collected by precipitation with ethanol. Consequently, the dT chain was lengthened by about 70 bases.

The DNA thus obtained was digested at 37° C. for 6 hours with 17 units of HpaI (NEB) and electrophoresed with agarose (low-melting agarose, BRL, 1%) to collect about 2.7 kb DNA fragment.

After the electrophoresis, the DNA was stained with 0.5 μg/ml of ethidium bromide, the agarose containing the approximately 2.7 kb fragment was cut out under UV irradiation, and to the agarose was added 5 times the volume of 20 mM tris-HCl (pH 8.0)-1 mM EDTA to dissolve the agarose at 65° C. over a period of 5 minutes, followed by extraction with phenol, then with phenol-chloroform (1:1) and thereafter with chloroform. The DNA was collected by precipitation with ethanol.

Subsequently, the vector primer DNA was purified by oligo(dA) cellulose column chromatography. The DNA was dissolved in 1 ml of 10 mM tris-HCl (pH 7.3)-1 mM EDTA-1M NaCl buffer. The solution was ice-cooled, then placed on the column equilibrated with the same buffer, which was thereafter washed with 1 ml of the same buffer and subsequently returned to room temperature. Elution then followed with 10 mM tris-HCl (pH7.3)-1 mM EDTA to collect the peak fraction. The DNA was collected by precipitation with ethanol, then dissolved in 100 μl of 10 mM tris-HCl (pH 7.3)-1 mM EDTA and stored at 4° C.

Linker DNA was prepared by the following procedure. pBR322-SV40 (0.19–0.32) DNA (100 μg) was digested with 120 units of PstI (NEB) at 37° C. for 1.5 hours. The termination of the reaction was followed by extraction with phenol-chloroform and precipitation with ethanol. The DNA collected was dissolved in 50 μl of mixture of 140 mM sodium cacodylate, 30 mM tris-HCl (pH 6.8), 1 mM $CoCl_2$, 0.1 mM DTT and 0.25 mM dGTP (containing 1 μCi of α-$^{32}$P-dGTP). The solution was acted on by 60 units of TTase for 20 minutes, whereby dG chain of 18 bases was attached. After the termination of the reaction, the DNA was collected digested with 50 units of HindIII (Takara Shuzo Co., Ltd.) and electrophoresed with agarose (1.8%) in the same manner as above to collect about 0.28 kb DNA fragment and obtain 2.3 μg of linker DNA.

(3-2) Synthesis of cDNA and preparation of cDNA library

RNA (5 μg) was dried in a vacuo, then dissolved in 10 μl of 5 mM tris-HCl (pH 8.3) heated at 65° C. for 5 minutes and immediately cooled to 37° C. To the reaction mixture was added 20 μl of mixture of 50 mM tris-HCl (pH 8.3), 8 mM $MgCl_2$, 30 mM KCl, 0.3 mM DTT, 2 mM dNTP and 10 μCi of α-$^{32}$P-dCTP. The resulting mixture was maintained at 37° C. for 5 minutes.

Ten units of RTase (reverse transcriptase, product of Seikagaku Kogyo Co., Ltd.) was added to the mixture and reacted therewith at 37° C. for 15 minutes. With addition of 10 units of RTase again, the mixture was maintained at the same temperature for 15 minutes. The reaction was terminated with 2 μl of 0.25 mM EDTA (pH 8.0) and 1 μl of 10% SDS, followed by extraction with phenol-chloroform. To the extract were added 20 μl of 4M ammonium acetate and 80 μl of ethanol, and the mixture was frozen at −70° C. for 15 minutes, then thawed at room temperature and centrifuged at 15000 r.p.m. and 4° C. for 10 minutes. The sediment was dissolved in 20 μl of 10 mM tris-HCl (pH 7.3). To the solution were added 19 μl of 4M ammonium acetate and 80 μl of ethanol to reprecipitate.

The precipitate was collected, washed with 70% ethanol and dissolved in 15 μl of mixture of 140 mM sodium cacodylate, 30 mM tris-HCl (pH 6.8), 1 mM $CoCl_2$, 0.1 mM DTT, 0.2 μg of poly A and 66 μM of (α-$^{32}$P)dCTP (10 μCi). TTase (P.L., 18 units) was added to the solution and reacted therewith at 37° C. for 5 minutes. The reaction mixture was rapidly cooled to 0° C., and the reaction was terminated with 1.3 μl of 0.25M EDTA and 0.65 μl of 10% SDS, followed by extraction with phenol-chloroform and precipitation with ethanol.

The precipitate was collected by centrifugation and then digested with 4 units of HindIII (Takara Shuzo Co., Ltd.) at 37° C. for 2 hours. Termination of the reaction was followed by extraction with phenol-chloroform and precipitation with ethanol. The precipitate was collected and dissolved in 10 μl of mixture of 10 mM tris-HCl (pH 7.3) and 1 mM EDTA. With addition of 3 μl of ethanol, the solution was preserved at −20° C.

One μl of the specimen thus obtained was maintained along with 5 ng of linker DNA in 10 μl of mixture of 10 mM tris-HCl (pH 7.5), 1 mM EDTA and 0.1M NaCl at 65° C. for 2 minutes and then at 42° C. for 30 minutes, and thereafter cooled to 0° C. To the mixture was added 90 μl of a mixture solution of 20 mM tris-HCl (pH 7.5), 4 mM MgCl$_2$, 10 mM (NH$_4$)$_2$SO$_4$, 0.1M KCl, 0.1 mM α-NAD, 50 μg/ml BSA-6 units/ml of E. coli DNA ligase, and then the combined solution was maintained at 12° C. overnight.

To the solution were added 0.5 μl of 10 mM dNTP, 0.56 μl of 10 mM NAD, 0.5 μl of E. coli DNA polymerase I (product of Boehringer Mannheim) and 0.2 μl of RNase H (PL). The mixture was maintained at 12° C. for one hour and then at 25° C. for one hour, and thereafter frozen at −20° C. for preservation.

E coli HB101 strain was incubated to OD$_{550}$ of 0.45 in LB medium (10 g of bacto-trypton, 5 g of bacto-yeast extract and 10 g/liter of NaCl). The culture was ice-cooled for 5 minutes and then centrifuged at 4° C. at 8000 r.p.m. for 5 minutes to harvest the cells. The pellets of cells were suspended in an ice-cooled mixture of 30 mM potassium acetate, 100 mM RbCl, 10 mM CaCl$_2$, 50 mM MnCl and 15% glycerin, maintained at 0° C. for 5 minutes and centrifuged at 4° C. at 8000 r.p.m. for 5 minutes. The cells collected were suspended again in a mixture of 10 mM MOPS (morpholinopropanesulfonic acid), 75 mM CaCl$_2$, 10 mM RbCl and 15% glycerin and maintained at 0° C. for 15 minutes to prepare competent cells, which were thereafter preserved at −70° C.

The frozen suspension was thawed at room temperature. The DNA specimen (20 μl) was added to a 400 μl portion of the suspension, and the mixture was allowed to stand at 0° C. for 30 minutes, subjected to heat shock at 42° C. for 90 seconds and then allowed to stand again at 0° C. for 1 to 2 minutes. With addition of 2 ml of LB medium, the mixture was maintained at 37° C. for 30 minutes. LB medium (50 times the volume of the mixture) was inoculated with the mixture, followed by incubation at 37° C. for 6 hours. Ampicillin was added to the culture to a concentration of 50 μg/ml, followed by incubation again overnight, whereby cDNA library was prepared. The cDNA library was preserved in 50% glycerin at −20° C.

(3-3) Preparation of synthetic probe

The following nucleotide acid sequence was derived from the amino acid sequence (20 residues from the N terminal) of the natural IL-1β determined as above.

Ala — Pro — Val — Arg — Ser — Leu — Asn — Cys —

5' GCC CCC GTG AGG TCC CTG AAC TGC

3' CGG GGG CAC TCC AGG GAC TTG ACG

Thr — Leu — Arg — Asp — Ser — Gln — Gln — Lys —

ACC CTG AGG GAC TCC CAG CAG AAG

TGG GAC TCC CTG AGG GTC GTC TTC

Ser — Leu — Val — Met

-continued
TCC CTG GTG ATG - 3'

AGG GAC CAC TAC - 5'

The above nucleotide sequence was determined according to the human codon usage frequency (Nucleic Acid Research, 9, r43–74 (1981)).

A nucleotide sequence (shown in the lowest line) complementary to the base sequence of the above formula is synthesized by the following method to use the complementaty sequence as a probe for selecting a transformant having cDNA coding for IL-1β. Thus, the fully protected DNA was synthesized by the solid-phase phosphite triester method wherein N,N-dialkylmethyl phosphoramidite derivative is used as a condensation unit (Nature, 310 105 (1984)), using an automatic synthesizer (380A DNA Synthesizer, Applied Biosystems Inc., Foster City, Calif. 94404, U.S.A.). Subsequently, the fully protected DNA was treated with 28% ammonia water at 55° C. for 10 hours, whereby the protective groups (i.e., the acyl groups for the amino groups of A, G and C) other than DMTr (dimethoxytrityl) group attached to the hydroxyl group at the 5' terminal were removed to obtain partially protected DNA. Next, the partially protected DNA was purified by reverse-phase HPLC using C$_{18}$ column and then treated with 80% acetic acid at room temperature for 10 minutes to remove DMTr group. The nucleotide thus obtained was purified by electrophoresis using 10% polyacrylamide gel containing 7M urea and by Bio-gel P-30 (Bio-Rad) to obtain the desired DNA (60 mer).

The DNA (6 μg) thus obtained was reacted with 12 units of T4 polynucleotide kinase (Takara Shuzo) at 37° C. for one hour in 50 μl of reaction mixture (50 mM tris-HCl (pH 7.6), 10 mM MgCl$_2$, 10 mM 2-mercapto ethanol, 0.2 mg/ml of fetal bovine thymus DNA and 50 μCi (γ-$^{32}$P)-ATP) to label the 5' terminal of the DNA. To separate the labeled DNA from the unreacted $^{32}$P, the reaction mixture was subjected to column chromatography using Biogel P-30 (Bio-Rad). The fraction of the labeled DNA was precipitated with 3M sodium acetate in ⅑ of the volume of the fraction and ethanol in 2.5 times the volume thereof. The precipitate was collected by centrifugation, dissolved in 400 μl of mixture of 10 mM tris-HCl (pH 8.0) and 1 mM EDTA and preserved at −20° C.

The specific activity of the resulting probe was at least 10$^7$ cpm/μg DNA.

(3–4) Screening of cDNA library

Twenty-four nitrocellulose filters (Millipore HAIFO 8250), 80 mm in diameter, were placed over LB agar medium containing 50 μg/ml of ampicillin, and the cDNA library solution was spread over the filters, as so diluted that 5000 colonies were applied to each filter, followed by incubation overnight at 37° C.

A fresh nitrocellulose filter was placed over the filter where colonies appeared to prepare a replica filter.

The original filter (master filter) was preserved at 4° C. The replica filter was held on the same agar medium as above at 37° C. for 6 hours for incubation and thereafter transferred onto LB agar medium containing 200 μg/ml of chloramphenicol, followed by incubation at 37° C. overnight.

The filter was treated with 0.5N NaOH, then with 1M tris-HCl (pH 8.0) and thereafter with a mixture of 1M tris-HCl (pH 8.0) and 1.5M NaCl. The filter was then dried in air and subsequently baked under a vacuum at 80° C. for 2 hours.

The baked filter, while being lightly shaken, was maintained at 68° C. overnight in 20 ml of solution of 1.2M NaCl, 0.12M trisodium citrate, 10 mg/ml of Ficoll, 10 mg/ml of polyvinylpyrrolidine, 10 mg/ml of BSA, 0.1% SDS and 1 mg/ml of salmon sperm DNA. The solution was replaced by a solution of 1.2M NaCl, 0.12M trisodium citrate, 10 mg/ml of Ficoll, 10 mg/ml of polyvinylpyrrolidine, 10 mg/ml of BSA, 0.1% SDS and $10^6$ cpm/ml of the probe, in which the filter was maintained at 42° C. overnight with light shaking for hybridization.

After the hybridization, the filter was withdrawn from the solution, washed with a solution of 1.2M NaCl, 0.12M sodium citrate and 0.1% SDS three times at room temperature and thereafter washed with the same solution at 60° C. until the count of the background of the filter became 200 cpm as determined by GM survey meter.

The filter was dried in air and then subjected to autoradiography at −70° C. for 2 days using sensitized paper and x-ray film (Fuji RX).

After developing the film, the colonies present in the signal region were scraped off from the master filter, and the foregoing procedure was repeated to isolate the colonies with a positive signal.

Consequently, clone I-2 having a strong signal was isolated.

(3–5) Analysis of clone

Restriction enzyme map of plasmid pGIF-α cDNA contained in clone I-2 was prepared.

Figure 14:
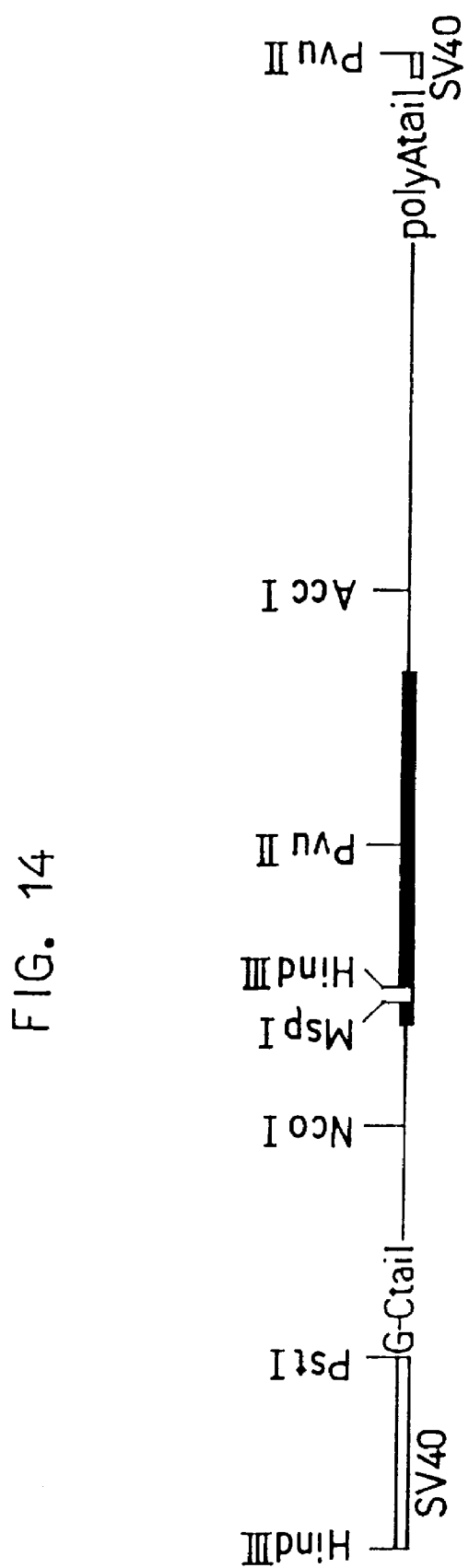
FIG. 14 is a restriction enzyme map of the plasmid-pGIF-α contained in the clone I-2 used in Example 2.

FIG. 14 shows the map.

FIG. 14 reveals that the cDNA has sites to be cleaved with NcoI (Nippon Gene), Hind III (Nippon Gene), PvuII (Nippon Gene) and AccI (Nippon Gene), one site by each, these cleavage sites being arranged in this order from the 5' terminus. It was found that the cDNA has a length of about 1.5 kb which is sufficient to code for GIF having a molecular weight of about 18 kd.

Next, the base sequence of pGIF-α cDNA was determined by the Maxam-Gilbert chemical modification method (Meth. Emzym. 65, 499–566, 1980) and the dideoxy-nucleotide chain termination method using M13 phage (Messing, J. and Vieira, J., Gene, 19, 269–276 (1982)).

CTTATTACAGTGGCAATGAGGATGACTTG

TTCTTTGAAGCTGATGGCCCTAAACAGATGAAG
                                Met Lys

TGCTCCTTCCAGGACCTGGACCTCTGCCCTCTG
Cys Ser Phe Gln Asp Leu Asp Leu Cys Pro Leu

GATGGCGGCATCCAGCTACGAATCTCCGACCAC
Asp Gly Gly Ile Gln Leu Arg Ile Ser Asp His

CACTACAGCAAGGGCTTCAGGCAGGCCGCGTCA
His Tyr Ser Lys Gly Phe Arg Gln Ala Ala Ser

GTTGTTGTGGCCATGGACAAGCTGAGGAAGATG
Val Val Val Ala Met Asp Lys Leu Arg Lys Met

CTGGTTCCCTGCCCACAGACCTTCCAGGAGAAT
Leu Val Pro Cys Pro Gln Thr Phe Gln Glu Asn

GACCTGAGCACCTTCTTTCCCTTCATCTTTGAA
Asp Leu Ser Thr Phe Phe Pro Phe Ile Phe Glu

GAAGAACCTATCTTCTTCGACACATGGGATAAC
Glu Glu Pro Ile Phe Phe Asp Thr Trp Asp Asn

GAGGCTTATGTGCACGATGCACCTGTACGATCA
Glu Ala Tyr Val His Asp Ala Pro Val Arg Ser

CTGAACTGCACGCTCCGGGACTCACAGCAAAAA
Leu Asn Cys Thr Leu Arg Asp Ser Gln Gln Lys

AGCTTGGTGATGTCTGGTCCATATGAACTGAAAJ
Ser Leu Val Met Ser Gly Pro Tyr Glu Leu Lys

GCTCTCCACCTCCAGGGACAGGATATGGAGCAA
Ala Leu His Leu Gln Gly Gln Asp Met Glu Gln

CAAGTGGTGTTCTCCATGTCCTTTGTACAAGGA
Gln Val Val Phe Ser Met Ser Phe Val Gln Gly

GAAGAAAGTAATGACAAAATACCTGTGGCCTTG
Glu Glu Ser Asn Asp Lys Ile Pro Val Ala Leu

GGCCTCAAGGAAAAGAATCTGTACCTGTCCTGC
Gly Leu Lys Glu Lys Asn Lue Tyr Leu Ser Cys

GTGTTGAAAGATGATAAGCCCACTCTACAGCTG
Val Leu Lys Asp Asp Lys Pro Thr Leu Gln Leu

GAGAGTGTAGATCCCAAAAATTACCCAAAGAAG
Glu Ser Val Asp Pro Lys Asn Tyr Pro Lys Lys

AAGATGGAAAAGCGATTTGTCTTCAACAAGATA
Lys Met Glu Lys Arg Phe Val Phe Asn Lys Ile

GAAATCAATAACAAGCTGGAATTTGAGTCTGCC
Glu Ile Asn Asn Lys Leu Glu Phe Glu Ser Ala

CAGTTCCCCAACTGGTACATCAGCACCTCTCAA
Gln Phe Pro Asn Trp Tyr Ile Ser Thr Ser Gln

GCAGAAAACATGCCCGTCTTCCTGGGAGGGACC
Ala Glu Asn Met Pro Val Phe Leu Gly Gly Thr

AAAGGCGGCCAGGATATAACTGACTTCACCATG
Lys Gly Gly Gln Asp Ile Thr Asp Phe Thr Met

CAATTTGTGTCTTCCTAAAGAGAGCTGTACCCA
Gln Phe Val Ser Ser

```
-continued
GAGAGTCCTGTGCTGAATGTGGACTCAATCCCT

AGGGCTGGCAGAAAGGGAACAGAAGGTTTTTGA

GTACGGCTATAGCCTGGACTTTCCTGTTGTCTA

CACCAATGCCCAACTGCCTGCCTTAGGGTAGTG

CTAAGACGATCTCCTGTCCATCAGCCAGGACAG

TCAGCTCTCTCCTTTCAGGGCCAATCCCAGCCC

TTTTGTTGAGCCAGGCCTCTCTCTCACCTCTCC

TACTCACTTAAAGCCCGCCTGACAGAAACCAGG

CCACATTTTGGTTCTAAGAAACCCTCCTCTGTC

ATTCGCTCCCACATTCTGATGAGCAACCGCTTC

CCTATTTATTTATTTATTTGTTTGTTTGTTTTG

ATTCATTGGTCTAATTTATTCAAAGGGGGCAAG

AAGTAGCAGTGTCTGTAAAAGAGCCTACTTTTT

ATTAGCTATGGAATCAATTCAATTTGGACTGGT

GTGCTCTCTTTAAATCAAGTCCTTTAATTAAGA

CTGAAAATATATAAGCTCAGATTATTTAAATGG

GAATATTTATAAATGAGCAAATATCATACTGTT

CAATGGTTCTCAAATAAACTTCACTAAAAAAAA

AAAAAAAAAAAAAAAAAAAAAA
```

The formula shows that the underlined region of the 312nd to the 371st nucleotides from the 5' terminal is complementary to the synthesized probe. The nucleotide sequence had 75% homology with the nucleotide sequence determined according to the human codon usage frequencies.

Further when the cDNA of pGIF-α was searched for the longest reading frame, this frame was found to be the region of the 57th to 771st nucleotides from the 5' terminal. The amino acid sequence corresponding to the nucleotide sequence of the 312nd to the 371st was found to be perfectly identical with the 20 amino acids at the N terminal of the natural IL-1β. This indicates that the cDNA of pGIF-α is cDNA coding for a IL-1β precursor protein.

The above nucleotide sequence reveals that the natural IL-1β is encoded in the nucleotide sequence of the 312nd to the 771st and is composed of 153 amino acids.

This result agreed with the foregoing propteries of the natural IL-1β (molecular weight, N-terminal amino acid sequence and amino acid composition).

This indicates that the primary structure of the protein of the natural IL-1β comprises the amino acid sequence of the formula (A). The transformant prepared by introducing the above plasmid, pGIF-α, into E. coli χ1776 has been deposited under the name of Escherichia coli χ1776/pGIF-α.

EXAMPLE 2

(I) Preparation by genetic engineering

Plasmid pGIF-α possessed by clone I-2 obtained by the procedure of Example 1, (II), (3–5) was cleaved with restriction enzymes HgiAI (NEB) and AccI (Nippon Gene) to obtain 581 base pairs (bp) gene coding for IL-1β. The 5' terminal and 3' terminal of the gene were cut with nuclease mung bean (Pharmacia P-L Biochemicals). The fragment is inserted into M13 phage RFmp10 at SmaI site. E. coli JM 105 is infected with the phage and incubated to obtain single-strand (SS)-DNA.

Subsequently, in the presence of M13 Universal Primer and Deoxy NTPs (Takara Shuzo), DNA polymerase I (Klenow Fragment (Takara Shuzo)) was caused to act on SS-DNA to synthesize double-strand (ds)-DNA, which was then cleaved with restriction enzymes EcoRI and BamHI (Nippon Gene) to obtain a DNA fragment having the desired restriction enzyme sites.

The fragment was inserted into expression vector pINIIIA 3 (Bio Technology, Vol. 2, 81–85 (1984)) at EcoRI and BamHI sites to obtain the desired plasmid pINIIIf-GIF-α.

Figure 15:
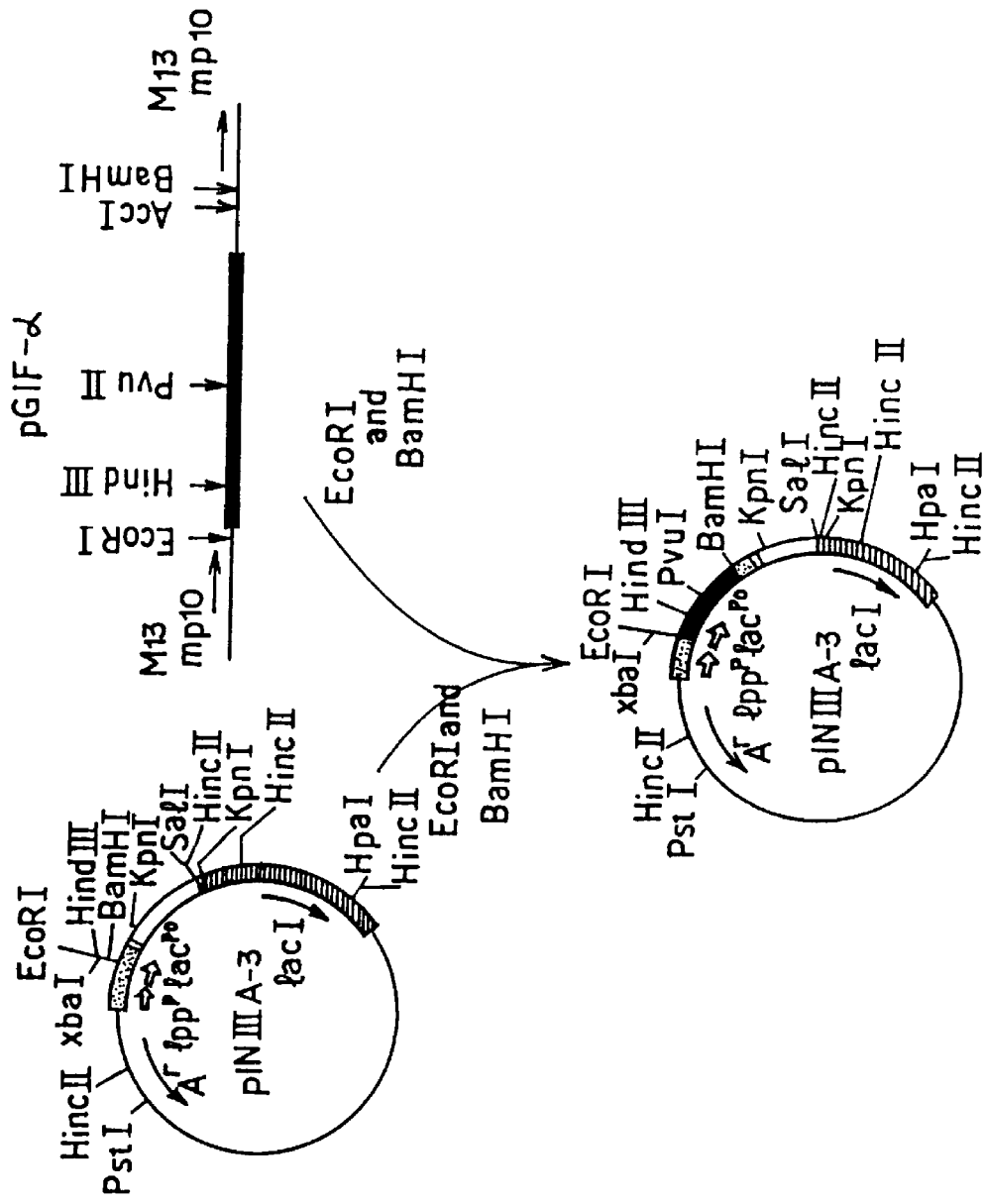
FIG. 15 is a diagram showing how a plasmid pINIIIf-GIF-α is constructed from the plasmid pGIF-α and a vector plasmid pINIIIA-3.

FIG. 15 schematically shows the above procedure.

The vector plasmid obtained was inserted into E. coli HB101 for transformation to obtain the desired transformant.

The transformant was incubated in L-broth medium (containing 50 µg of ampicillin per ml) with shaking at 37° C. When cells grew to $OD_{650}$ of 0.2, isopropyl-α-D-thiogalactopyranoside (IPTG) was added to the medium to a final concentration of 2 mM. One-ml samples of the culture were collected 2 hours, 5 hours and 6.5 hours after the addition of IPTG. Each sample was centrifuged (10000 r.p.m., five minutes), and the cells were collected, dissolved in 1 ml of EDTA-lysozyme-Triton ×100 (final concentration 1%), then sonicated and checked for GIF activity.

The above procedure was repeated using vector plasmid pINIIIA-3 as a control.

Table 5 shows the results.

TABLE 5

| DNA in E. coli transformant | Lapse of time after IPTG addition (hr) | GIF activity (units/ml culture) |
|---|---|---|
| pINIIIf-GIF-α | 2 | 12000 |
|  | 5 | 24200 |
|  | 6.5 | 40100 |
| pINIIIA-3 | 6.5 | not detected |

Table 5 shows that the desired GIF active substance can be produced by incubating the transformant with plasmid pINIIIf-GIF-α.

(II) Preparation of Polypeptide I (1) The following oligodeoxynucleotides (I) and (II) were prepared by the procedures described below.

5' HOCGATAATGGCTCCTGTACGTTCTCT-GAACTGCACTCTCOH 3' (I)

5' HOCGGAGAGTGCAGTTCAGAGAACGTA-CAGGAGCCATTATOH 3' (II)

5'-O-Dimethoxytrityl and N-protected deoxynucleoside (Applied Biosystems Inc.) attached to macroporous silica were used as starting materials. The nucleotide chain was successively lengthened from the 3' terminal toward the 5' terminal with the condensation units of 5'-O-dimethoxytrityl and N-protected deoxymono-nucleoside-3'-phosphoamidite, using an automatic synthesizer (380A DNA synthesizer, Applied Biosystems Inc.). The resulting product was treated with thiophenol for demethylation and further treated with 28% ammonia water at room temperature to remove the nucleotide from the silica, whereby fully protected oligonucleotide was obtained. The above procedure was executed entirely by the automatic synthesizer (Hunkapiller et al., Nature, 310, 105 (1984)).

The oligonucleotide was treated with 2 ml of 28% ammonia water at 55° C. for 10 hours to remove the N-protective group and obtain 5'-O-dimethoxytrityl-oligonucleotide. One fifth of the amount of the product was purified by reverse-phase high-performance liquid chromatography using ODS (Yamamura Kagaku Kenkyusho Co., Ltd.) column and then treated with 150 μl of 80% acetic acid at room temperature for 20 minutes to obtain crude oligonucleotide. The product was further purified by reverse-phase high-performance liquid chromatography with ODS column to obtain the desired oligonucleotide.

The plasmid pGIF-α obtained by the procedure of Example 1, (II), (3–5) was cleaved with restriction enzymes AccI and ClaI to obtain a DNA fragment of about 1.2 kilo base pairs (kbp), which was isolated and purified by agarose gel electrophoresis. The DNA fragment was made blunt at the ends cleaved with restriction enzymes AccI and ClaI, using DNA polymerase I (Klenow fragment).

On the other hand, BamHI linker (5' HOCGGATCCGOH 3') was phosphorylated at the 5' terminal with T4 polynucleotide kinase and joined to the blunt-ended DNA fragment with T4 DNA ligase, followed by digestion with restriction enzyme BamHI and further with restrcition enzyme MspI. The resulting reaction product was electrophoresed on agarose gel to isolate purified MspI-BamHI DNA fragment of about 540 bp.

The oligodeoxynucleotides (I) and (II) synthesized above were phosphorylated at the 5' terminal with T4 polynucleotide kinase and joined to MspI-BamHI DNA fragment using T4 DNA ligase, followed by digestion with restriction enzymes BamHI and ClaI. The reaction product was electrophoresed on agarose gel to isolate purified ClaI-BamHI DNA fragment of about 580 bp.

On the other hand, plasmids pTMI (Fumio Imamoto, Taishya, Vol. 22, 289 (1985)) were cleaved with restriction enzymes BamHI and ClaI, followed by agarose gel electrophoresis to isolate and purify DNA fragment of about 4.4 kbp having a trp promotor region. The DNA fragment and the ClaI-BamHI DNA fragment of about 580 bp prepared above were ligated with T4 DNA ligase to obtain the desired plasmid ptrpGIF-α for express polypeptide I.

The plasmid was introduced into E. coli HB101 for transformation, and the desired transformant E. coli HB101/ptrpGIF-α was selected by the restriction enzyme analysis of the plasmid DNAs which was obtained by the boiling method (T. Maniatis, E.F. Fritsch and J. Sambrook, Molecular Cloning, p. 366, Cold Spring Harfor Laboratory, (1982)).

Figure 16:
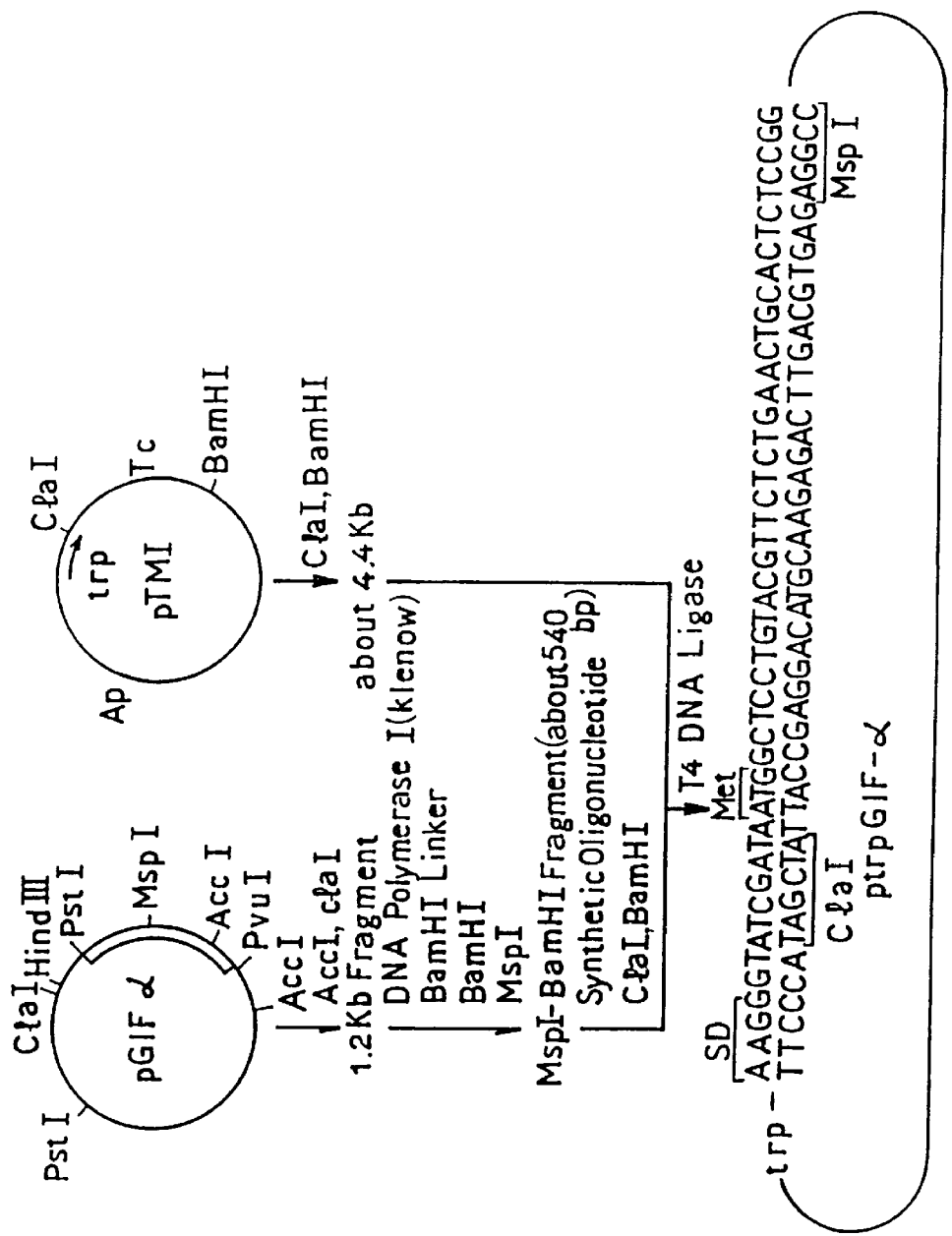
FIG. 16 is a diagram showing how a plasmid ptrpGIF-α is constructed from a pGIF-α and a plasmid pTMI.

FIG. 16 schematically shows the above procedure.

The transformant prepared by introducing the plasmid ptrpGIF-α into E. coli χ1776 has been deposited under the name of *Escherichia coli* χ1776/ptrpGIF-α and deposition number FERM BP-949 in Fermentation Research Institute, Agency of Industrial Science and Technology since Dec. 12, 1985.

(2) Culture of transformant

The transformant obtained above, i.e., E. coli HB101/ptrpGIF-α was incubated overnight at 37° C. with shaking in 10 ml of LB medium (1% tryptone, 0.5% yeast extract and 0.5% NaCl) containing 50 μg/ml of ampicillin and 20 μg/ml of L-tryptophan. One-ml portion of the culture was inoculated in 50 ml of M9 minumum medium (0.6% $Na_2HPO_4$, 0.3% $KH_2PO_4$, 0.05% NaCl, 0.1% $NH_4Cl$, 2 mM $MgSO_4$, 0.2% glucose and 0.1 mM $CaCl_2$) containing 50 μg/ml of ampicillin and 1% Casamino acid and incubated at 37° C. with shaking. The cells were harvested when the absorbance (O.D.) at 550 nm reached 1.0 and suspended in 5 ml of a solution of 15% sucrose, 50 mM tris-HCl (pH 8.0) and 50 mM EDTA (pH 8.0). A 500 μl of 10 mg/ml of lysozyme (as dissolved in 10 mM tris-HCl (pH 8.0)) was added to the suspension, and 5 ml of a solution of 0.3% Triton ×100, 187.5 mM EDTA (pH 8.0) and 150 mM tris-HCl (pH 8.0) was further added. The mixture was allowed to stand at room temperature for 15 minutes, then thoroughly stirred and centrifuged to obtain a GIF activity positive-supernatant of cell extract.

(3) Purification of Polypeptide I

Ion-exchange chromatograph (CM-HPLC)

The cell extract supernatant prepared as above was dialyzed with 50 mM sodium acetate buffer (pH 5.5), and the dialyzate was subjected to ion-exchange chromatography (CM-HPLC) using Gilson high permeation liquid chromatography system (Gilson) under the following conditions.

Column : IEX-535CM (6.0×150 mm, Toyo Soda Co., Ltd.)

Eluent A: 50 mM sodium acetate (pH 5.5)

Eluent B: 50 mM sodium acetate (pH 5.5) containing 0.5M NaCl

Flow rate : 0.5 ml/min.

| Fraction volume: Retention time: | |
|---|---|
| 0–60 min | 2 ml/4 min/tube |
| 60–120 min | 0.5 ml/min/tube |
| 120–180 min | 2 ml/4 min/tube |

| Concentration gradient: | |
|---|---|
| Time (min) | % B |
| 0 | 0 |
| 40 | 0 |
| 120 | 20 |
| 140 | 100 |
| 165 | 100 |
| 170 | 0 |

Reverse-phase high-performance liquid chromatography

The CM-HPLC procedure resulted in a GIF active fraction with a retention time of 90 to 91 minutes.

The active fraction was then subjected to reverse-phase high-performance liquid chromatography under the following conditions.

Column : $C_4$ Highpore reverse-phase column (RP304, Bio-Rad, 250 mm×4.6 mm (diam.)

Eluents : A liquid=0.% TFA B liquid=acetonitrile-1% TFA (9:1)

Flow rate : 1 ml/min.

| Chart speed: Retention time: | |
|---|---|
| 0–50 min | 5 min/cm |
| 50–80 min | 2 min/cm |

| Concentration gradient: | |
|---|---|
| Time (min) | % B |
| 0 | 0 |
| 5 | 0 |
| 15 | 20 |
| 75 | 45 |
| 80 | 100 |
| 85 | 100 |
| 90 | 0 |

Fraction volume: 2 ml/2 min/tube

There was obtained at a retention time of 63.9 to 65.3 minutes the desired Polypeptide I exhibiting a single protein absorbance peak matching that of GIF activity.

The Polypeptide I thus obtained possess IL-1 activity and the specific activity was $2.7 \times 10^7$ GIF units/mg protein.

(4) Identification of Polypeptide I
SDS polyacrylamide gel electrophoresis (SDS-PAGE)

The SDS-PAGE analysis of Polypeptide I obtained by the above procedure (3) was conducted in accordance with the method of Laemmli, U.K. (Nature, 277, 680 (1970)) under the following conditions.

Specimen: The Polypeptide I fraction obtained by the reverse phase HPLC procedure was completely dried, then dissolved in Laemmli sample buffer (not containing 2-mercapto ethanol (2ME$^-$) or containing 2-mercapto ethanol in an amount of ⅟₂₀ the volume of the buffer (2ME$^+$)) and treated at 100° C. for 4 minutes.

Gel : 15% Polyacrylamide gel 1.5 mm in thickness

Apparatus : Protean, product of Bio-Rad

Electrophoresis : 40 mA constant current for 2 hours

Figure 17:
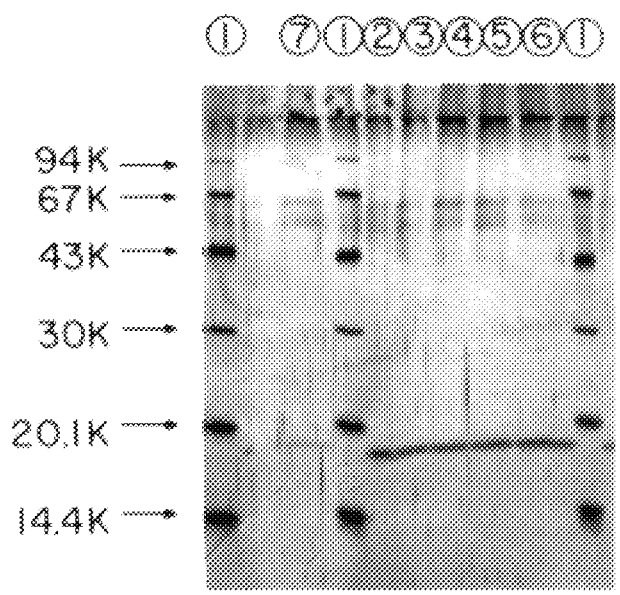
FIG. 17 shows the results of analysis obtained by subjecting polypeptide I to SDS-PAGE (2ME$^+$).
Figure 18:
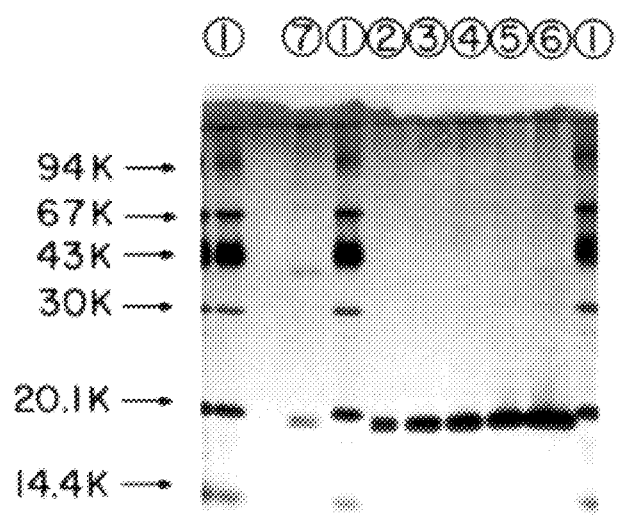
FIG. 18 shows said results in the case of 2ME$^-$.

The gel resulting from the electrophoresis was stained with Silver Stain Kit (Bio-Rad) with the results shown in FIG. 17 (in the case of 2ME$^+$) and FIG. 18 (for 2ME$^-$).

With reference to these drawings, lane (1) resulted from the following molecular weight markers, lane (2) to (6) from the polypeptide I specimen, and lane (7) from natural IL-1β specimen. The amounts of polypeptide I specimen used were 11.7 ng for lane (2), 23.3 ng for lane (3), 46.6 ng for lane (4), 70 ng for lane (5) and 117 ng for lane (6).

Molecular weight markers for lane (1)
94K : Phosphorylase b
67K : Albumin
43K : Ovalbumin
30K : Carbonic anhydrase
20.1K: Trypsin inhibitor
14.4K: α-Lactoalubumin The results indicate that Polypeptide I is migrated as a single band at the position of about 17 Kd in the case of 2ME$^+$ or of about 17.5 Kd in the case of 2ME$^-$.

Isoelectrofocussing (IEF)

Polypeptide I was subjected to IEF using PAG plate(LKB) 3.5 to 9.5 in pH range, and Model 1415 (Bio-Rad) under the following conditions.

Specimen: Four lanes were used, i.e. 0.037 μg, 0.074 μg and 0.74 μg portions of polypeptide I obtained by the foregoing procedure (3) and the following marker proteins (pI marker protein).

Marker proteins
Amyloglucosidase (3.50)
Soybean trypsin inhibitor (4.55)
β-lactoglobulin A (5.20)
Bovine carbonic anhydrase B (5.85)
Human carbonic anhydrase B (6.55)
Horse myoglobin-acidic band (6.85)
Horse myoglobin-basic band (7.35)
Lentil lectin-acidic band (8.15)
Lentil lectin-middle band (8.45)
Lentil lectin-basic band (8.65)
Tryspinogen (9.30)

Electrode solutions: Anode solution=1M H$_3$PO$_4$ Cathode solution=1M NaOH

Electrophoresis : With constant power of 1 W/cm gel width with cooling (10° C.) for 90 minutes Staining: With silver stain Kit The gel resulting from the electrophoresis was sliced at a spacing of 1 cm, subjected to extraction with use of 1 ml of distilled water with shaking (for two days) and then checked for pH to calculate the isoelectric point.

Polypeptide I had an isoelectric point (PI) of 6.8±0.1 and appeared as a single band at this position.

Amino acid composition

The Polypeptide I fraction (30 μl) obtained by the reverse-phase high-performance liquid chromatographic procedure (3) was carefully placed into the bottom of a thick-walled hard test tube made of Pyrex glass and 12 mm ×120 mm, and was dried in a vacuum in a desiccator containing sodium hydroxide pellets. A 50 μl quantity of 4N methanesulfonic acid (containing 0.2% 3-(2-aminoethyl)-indole and produced by Pierce) was added to the dry specimen within the tube. The interior of the tube was deaerated at 0.1 to 0.2 mm Hg for 1 minute and then sealed off. The specimen was hydrolyzed in a heater at 118° C. over a period of 24 hours. After opening the tube, the mixture was neutralized with 46 μl of 4N sodium hydroxide and diluted to an amount of 450 μl with citric acid buffer.

A 250 μl quantity of the specimen solution was used for amino acid analysis by an amino acid analyzer (Model HITACHI 835, product of Hitachi Ltd.). The amino acids separated were detected by the o-phthalaldehyde method and quantitatively determined with reference to calibration curves prepared with use of authentic amino acids.

Table 6 shows the results in terms of the mole ratio of component amino acids based on Phe (9 moles). Under the above analysis conditions, Pro and Cys are not determinable. For Ser, Thr and Met, the percent recovery as achieved under the above conditions is given in parentheses.

TABLE 6

| Amino acid | Mole ratio |
| --- | --- |
| Asp and/or Asn | 17.1 |
| Ser | 10.9 (80%) |
| Thr | 5.4 (90%) |
| Glu and/or Gln | 23.8 |
| Gly | 8.3 |
| Ala | 5.0 |
| Val | 10.8 |
| Met | 5.5 (90%) |
| Ile | 4.9 |
| Leu | 15.1 |
| Tyr | 3.9 |
| Phe | (9) |
| Lys | 14.9 |
| His | 0.9 |
| Trp | 0.8 |
| Arg | 3.0 |

Amino acid sequence

A 150 μl quantity of Polypeptide I fraction obtained by the reverse-phase high-performance chromato-graphic procedure (3) was analyzed by a protein sequencer (Applied Biosystems Inc.). Each resulting PTH-amino acid was suitably diluted with 100 to 50 μl of 33% aqueous acetonitrile solution, and 5-μl portion of the dilution was injected into a chromatographic column by an autosampler, Waters 710B. For the chromatographic system, two pumps, Beckman Model 112, were operated by a controller, Model 421. The column used, measuring 2 mm×250 mm and packed with Ultrasphere ODS-5 μm, was maintained at 55° C. by a column heater. The flow rate was 0.3 ml/min. A mixture of 20 mM sodium acetate and acetonitrile was used for gradient elution. Absorbance was monitored at 269 nm. Analysis was conducted for 45 minutes.

The results of 20 cycles of analysis revealed that Polypeptide I obtaned by the procedure (3) had the following sequence of 20 amino acids at the N terminal.

Ala-Pro-Val-Arg-Ser-Leu-Asn-Cys-Thr-Leu-Arg-Asp-Ser-Gln-Gln-Lys-Ser-Leu-Val-Met-Ser was confirmed by one of by-products and was further confirmed as a dehydro form showing absorption at 322 nm.

In cycle 8, the peak of by-product appeared to indicate Cys, and Cys was further identified by analyzing the original specimen after carboxamidemethylation.

Further polypeptide I was digested with trypsin to obtain peptide fragments. Amino acid composition analysis of the fragments revealed that the C terminal peptide was accurately contained in the polypeptide free of damage.

Stated more specifically, a 60 μg portion of polypeptide I was dissolved in 600 μl of 1% ammonium hydrogen carbonate. To the solution was added 20 μl of a solution of trypsin (0.2 mg/ml, product of Cooper Biomedical) in 1% ammonium hydrogen carbonate. The mixture was allowed to stand at 37° C. for 24 hours to obtain peptides cleaved with tripsin. The peptide mixture was subjected to reverse-phase HPLC (C-18, 300Å, 4.6×150 mm; with use of 0.1% TFA as A solution and acetonitrile containing 1% TFA in 1/10 of the volume of the nitrile as B solution while increasing the amount of B solution at a rate of 1%/3 min for elution). All the components were isolated by the time the proportion of B solution increased to 40%. The peptides were subjected to amino acid analysis, whereby all the anticipated peptide fragments were identified. Especially, the C terminal peptide was found free from basic amino acids, and was found to contain the anticipated amino acids accurately by the analysis. Consequently, polypeptide I obtained by the procedure (3) had an accurate C terminal as anticipated.

In the same manner as above, the peptide fragments were checked for amino acid sequence. All the sequences confirmed were found to match the sequence of IL-1β. The confirmed sequences of the peptide fragments checked are shown below in amino acid numbers of IL-1β. 1–4, 5–11, 12–16, 17–27, 28–63, 64–65, 66–74, 75–88, 89–92, 95–98, 99–103, 104–109, 110–138, 139–153.

These results revealed that polypeptide I obtained by the procedure (3) was polypeptide I having the specified sequence. The calculated molecular weight of polypeptide I is 17376.59.

Antitumor activity in vivo

Polypeptide I obtained by the procedure (3) was tested in vivo for antitumor activity as described below.

1) One million viable A375 cells were inoculated s.c. in a BALB/c nude mouse on day 0. Polypeptide I was administered i.t. at a daily dose of 100,000 GIF units/ body from days 10 to 15. Six mice were used for one group.

PBS only was similarly given to a control group.

Figure 19:
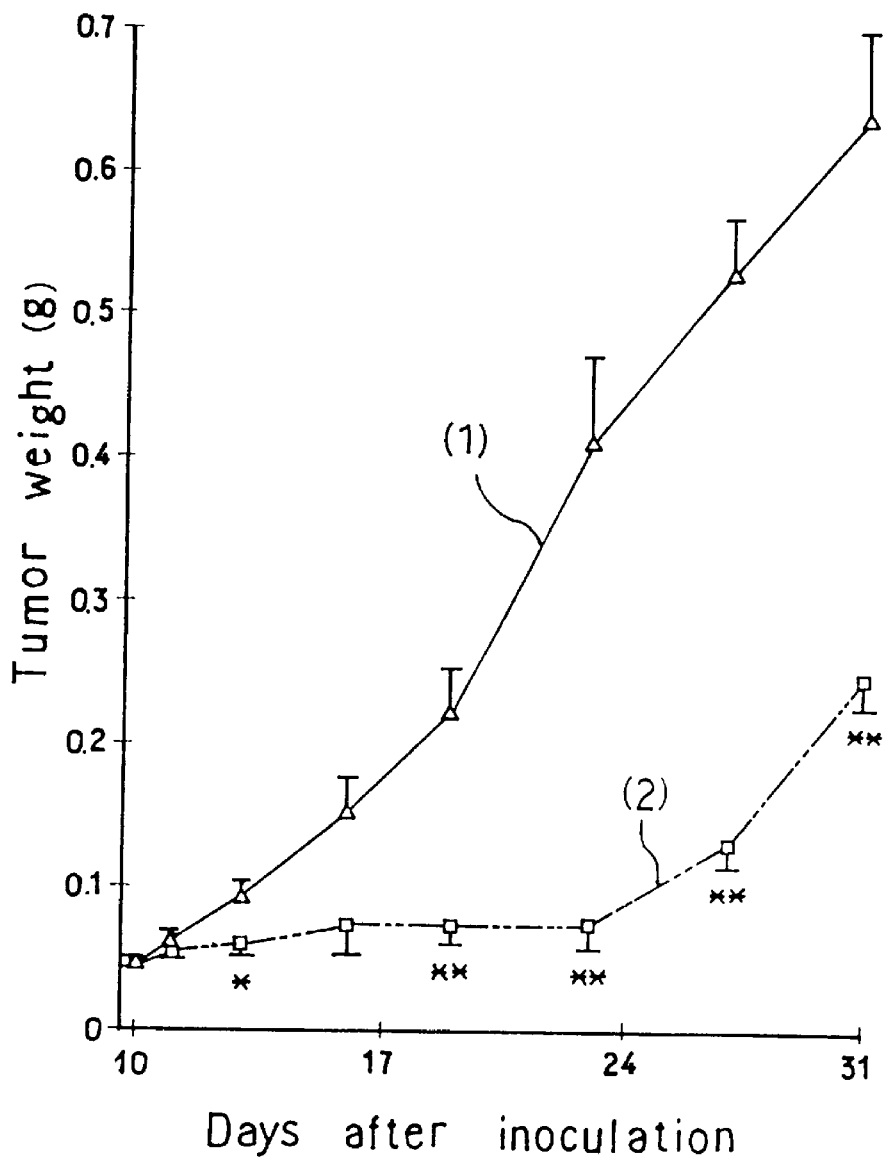
FIG. 19 and 20 are graphs showing the results obtained by testing polypeptide I for anti-tumor activity in vivo.

The results are shown in FIG. 19 in which line (1) represents the control group, and line (2) represents the group given polypeptide I.

Figure 20:
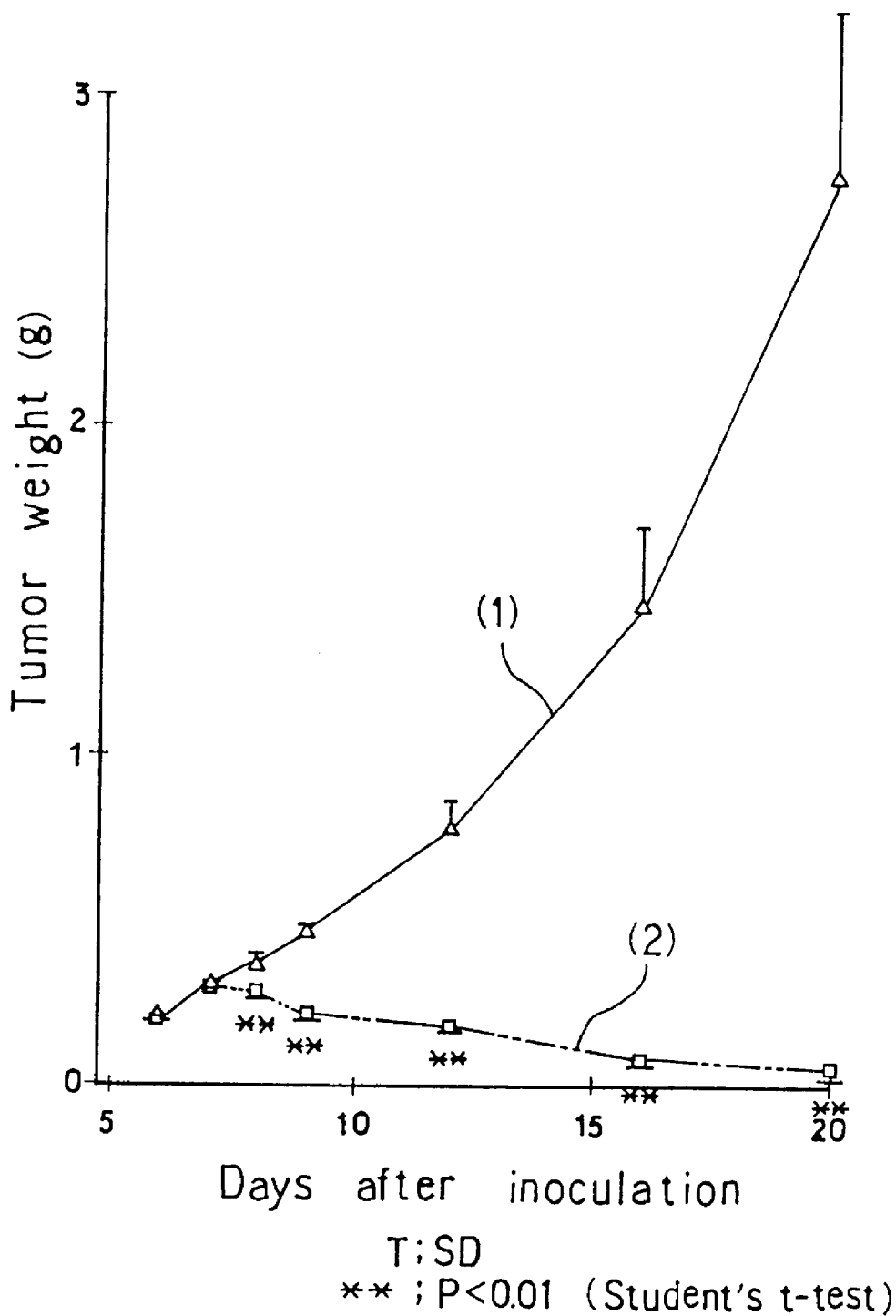

2) A BALB/c mouse was intracutaneously inoculated with 200,000 viable Meth A cells on day 0. Polypeptide I was administered i.t. at a daily dose of 100,000 GIF units/body on days 7 and 8. Seven mice were used for one group. PBS only was similarly given to a control group. FIG. 20 shows the results in which line (1) represents the control group and line (2) represents the group given polypeptide I. Five in the test group exhibited regression of the tumor.

EXAMPLE 3

(1) Preparation of Polypeptide VI ptrpGIF-α obtained by the Ex. 2 was used for preparing Polypeptide VI having the amino acid sequence of polypeptide I wherein the 71st amino acid, Cys, from the N terminal was replaced by Ser, according to the site-specific mutagenesis method (Pro. Nat. Acad. Sci., 81, 5662–5666 (1984); Science, 224, 1431 1984)).

M13 mp 11 phage vector was used as a single-strand DNA template. EcoRI/BamHI DNA fragment was isolated from plasmid ptrpGIF-α and cloned in M13 mp 11 phage at restriction enzyme EcoRI and BamHI sites to obtain single-strand (ss) DNA (M13-GIF-α), which was then used as a mutagenesis template. Synthetic oligonucleotide [5'-CTGTCCTCAGTGTTG-3' (primer)] was phosphorylated with T4 polynucleotide kinase and hybridized with ss M13-GIF-αDNA. The hybrid was annealed, thereafter treated with DNA polymerase I, (Klenow fragment) and T4 DNA ligase in the presence of dNTPs and incubated at 15° C. for 18 hours.

The DNA obtained was introduced into JM105 competent cell for transformation. The resulting phage plaque (50 colonies) was inoculated onto an agar plate and incubated at 37° C. for 18 hours. A filter containing the culture was treated with an alkali in the usual manner for denaturation, dried and then baked at 80° C. for 2 hours. The DNA was prehybridized and then hybridized at room temperature with $^{32}P$ probe prepared by labeling the primer with $^{32}P$-r-ATP. The filter resulting from the hybridization was washed with 6× SSC buffer at room temperature for 10 minutes and further at 37° C. for 10 minutes, dried and thereafter subjected to autoradiography at −70° C. for 18 hours.

M13-GIF-71s was selected as a typical clone from among five mutant clones, infected with JM105 and incubated to prepare ssDNA and RF DNA.

M13 dideoxynucleotide sequencing was performed for ssDNA to confirm mutation of the contemplated gene.

Newly produced restriction enzyme DdeI site was also identified in RF DNA.

EcoRI/BamHI fragment was prepared from RF DNA produced in JM105, introduced into expression plasmid as in above (1) to obtain the desired polypeptide VI expression plasmid ptrpGIF-α-71S.

E. coli HB 101 transformant harboring the foregoing plasmid was deposited under FERM No.BP1296 as "Escherichia coli HB 101/ptrp GIF-α-71S" with Fermentation Research Institute, Agency of Industrial Scienece and Technology (FERM).

A cell extract supernatant was prepared with use of the plasmid in the same manner as in Example 2-(II) (2) and checked for GIF activity. Consequently, the GIF activity was $2.4 \times 10^6$ units/ml culture when E. coli HB101 was used as the host.

The desired polypeptide VI was isolated from the cell extract supernatant and purified in the same manner as in Example 2-(II) (3).

(2) Preparation of polypeptide IV

Polypeptide IV was prepared in the same manner as in the above procedure (1) using plasmid ptrpGIF-α.

M13 mp 11 phage vector was used as a single-strand DNA template. EcoRI/BamHI DNA fragment was isolated from plasmid ptrpGIF-α and cloned in M13 mp 11 phage at restriction enzyme EcoRI and BamHI sites to obtain single-strand (ss) DNA (Ml3-GIF-α), which was then used as a mutagenesis template. Synthetic oligonucleotide [5'-CTGAACTCGACTCTC-3' (primer)] was phosphorylated with T4 polynucleotide kinase and hybridized with ss M13-GIF-αDNA. The hybrid was annealed, thereafter treated with DNA polymerase I, (Klenow fragment) and T4 DNA ligase in the presence of dNTPs and incubated at 15° C. for 18 hours.

The DNA obtained was introduced into JM105 competent cell for transformation. The resulting phage plaque (100 colonies) was inoculated onto an agar plate and incubated at 37° C. for 18 hours. A filter containing the culture was treated with an alkali in the usual manner for denaturation, dried and then baked at 80° C. for 2 hours. The DNA was prehybridized and then hybridized at room temperature with $^{32}$P probe prepared by labeling the primer with $^{32}$P-r-ATP. The filter resulting from the hybridization was washed with 6× SSC buffer at room temperature for 10 minutes and further at 37° C. for 10 minutes, dried and thereafter subjected to autoradiography at −70° C. for 18 hours.

M13-GIF-8s was selected as a typical clone from among four mutant clones, infected with JM105 and incubated to prepare ssDNA and RF DNA.

M13 dideoxynucleotide sequencing was performed for ssDNA to confirm mutation of the contemplated gene.

Newly produced restriction enzyme HinfI site was also identified in RF DNA.

EcoRI/BamHI fragment was prepared from RF DNA produced in JM105, introduced into expression plasmid as in Example 2-(II) (1) to obtain the desired polypeptide IV expression plasmid ptrpGIF-α-8S.

A cell extract supernatant was prepared with use of the plasmid in the same manner as in Example 2-(II) (2) and checked for GIF activity. The activity was $1.2 \times 10^5$ units/ml culture when *E. coli* HB101 was used as the host, or $6.2 \times 10^5$ units/ml culture when *E. coli* W3110 was used.

From the cell extract supernatant, the desired polypeptide VI was isolated, followed by purification, by the same method as in Example 2-(II) (3).

(3) Preparation of polypeptide V

Plasmid ptrpGIF-α-71S and ptrpGIF-α-8S obtained by the foregoing procedures were cleaved with restriction enzymes EcoRI and HindIII to isolate approximately 400-bp DNA fragment from ptrpGIF-α-8S and approximately 4600-bp DNA fragment from ptrpGIF-α-71S. These fragments were ligated to obtain plasmid ptrpGIF-α-8S71S for expressing the desired polypeptide V having the amino acid sequence of IL-1β (polypeptide I) wherein the 8th and 71st amino acids, Cys, from the N terminal were each replaced by Ser.

In the same manner as in Example 2-(II) (2), a cell extract supernatant was prepared using the plasmid. (The GIF activity was $1.4 \times 10^4$ units/ml culture when *E. coli* HB101 was used as the host, or $5 \times 10^5$ units/ml culture when *E. coli* W3110 was used.) The desired polypeptide V was isolated from the cell extract supernatant and purified in the same manner as in Reference Example 2-(3).

(4) Preparation of polypeptide II,

In the same manner as the above procedure (1), polypeptide II expression plasmid ptrpGIF-α-4G was obtained using 5'-GCTCCTGTAGGTTCTCTG-3' as the primer.

*E. coli* EB 101 transformant harboring the foregoing plasmid was deposited under FERM No.BP1297 as "*Escherichia coli* HB 101/ptrp GIF-α-4G" with Fermentation Research Institute, Agency of Industrial Scienece and Technology (FERM).

In the same manner as in Example 2-(II) (2), a cell extract supernatant was prepared using the plasmid. (The GIF activity was $2.8 \times 10^5$ units/ml culture when *E. coli* HB101 was used-as the host.) The desired polypeptide II was isolated from the cell extract supernatant and purified in the same manner as in Example 2-(II) (3).

In this purification procedure, polypeptide XXXXVIII was obtained as purified by rechromatography at the first half of the main peak of CM-HPLC. The polypeptide XXXXVIII was substantially equal to the polypeptide II in the activity to promote the production of CSF and was low in any of GIF activity, LAF activity and activity to promote the production of PGE.

(5) Preparation of polypeptide III

By the same procedure as the foregoing (1), polypeptide III expression plasmid ptrpGIF-α-11Q was obtained using 5'-GCACTCTCCAGGACTCACA-3' as the primer.

In the same manner as in Example 2-(II) (2), a cell extract supernatant was prepared using the plasmid. (The GIF activity was $2.8 \times 10^6$ units/ml culture when *E. coli* HB101 was used as the host.) The desired polypeptide III was isolated from the cell extract supernatant and purified in the same manner as in Example 2-(II) (3).

(6) Preparation of polypeptide VII

By the same procedure as the foregoing (1), polypeptide VII expression plasmid ptrpGIF-α-102CT was obtained using 5'-TCTTCAACTAGATAGAA-3' as the primer.

In the same manner as in Example 2-(II) (2), a cell extract supernatant was prepared using the plasmid. (The GIF activity was $7.4 \times 10^4$ units/ml culture when *E. coli* HB101 was used as the host.) The desired polypeptide VII was isolated from the cell extract supernatant and purified in the same manner as in Example 2-(II) (3).

(7) Preparation of polypeptide VIII

By the same procedure as the foregoing (1), polypeptide VIII expression plasmid ptrpGIF-α-140CT was obtained using 5'AAAGGCGGCTAGGATATAA-3' as the primer.

In the same manner as in Example 2-(II) (2), a cell extract supernatant was prepared using the plasmid. (The GIF activity was $5.8 \times 10^3$ units/ml culture when *E. coli* W3110 was used as the host.) The desired polypeptide VIII was isolated from the cell extract supernatant and purified in the same manner as in Example 2-(II) (3).

Further the plasmid ptrpGIF-α-140CT was introduced into *E. coli* HB101 as the host for expression, giving a cell extract supernatant ($1.3 \times 10^6$ units/ml culture in GIF activity) in the same manner as above. Polypeptide I was isolated from the supernatant and purified similarly.

When *E. coli* HB101 is used as the host in the above case, supE acts as a nonsense suppressor, and UAG stop codon is read through as Gln to express polypeptide I. On the other hand, when *E. coli* W3110 is used as the host, UAG acts as the stop codon since supE gene is not coded for, with the result that polypeptide VIII is expressed which comprises a sequence of 140 amino acids.

(8) Identification of polypeptides II to VIII

IL-1β derivatives (polypeptides II to VIII) of the invention prepared by the foregoing procedures (1) to (7) were subjected to SDS-PAGE (18% polyacrylamide gel, 2ME+) in the same manner as in Example 2-(II) (4).

Consequently, each of polypeptides II to VII migrated as a single band at the position of about 17.5 kd, and polypeptide VIII migrated similarly at the position of about 16 kd.

Further Western blotting (Proc. Natl. Acad. Sci., U.S.A., 76, 1420 (1979)) was conducted for polypeptides I to VIII using neutral antiserum for GIF activity of polypeptide I (prepared by immunizing a rabit with polypeptide I obtained in Example 2-(II) (3) by the usual method), whereby each of these polypeptides was confirmed as a single band at the corresponding position.

EXAMPLE 4

(1) The transformant (*E. coli* HB101/ptrpGIF-α) obtained in Example 2-(II) (1) was incubated overnight at 37° C. in 400 ml of LB medium containing 50 μg/mg of ampicillin and 20 μg/ml of L-tryptophan. M9 minimum medium (20 liters) containing 1% Casamino acid was inoculated with the culture (400 ml), followed by incubation at 37° C. for 8.5 hours.

The resulting culture was centrifuged to collect the cells, which were suspended in 1M $Na_2HPO_4$ and allowed to stand overnight in a cool chamber. The suspension was thereafter dialyzed against 10 mM tris-HCl buffer (pH 8.0) for 2 days.

The dialyzate obtained was centrifuged (10000 r.p.m., 30 minutes) to obtain a supernatant.

The supernatant was collected in an amount corresponding to 300 liters of *E. coli* culture, adjusted to a pH of 5.0 with 100 mM acetic acid and passed through Zeta Prep SP-250 cartridge (product of LKB) at a flow rate of 30 ml/min. The elution was conducted with 10 mM sodium acetate (pH 5.3) for 100 minutes, then with 50 mM sodium acetate (pH 5.5) containing 0.1M NaCl for 220 minutes, and further with 50 mM sodium acetate (pH 5.5) containing 1M NaCl. The fractions were checked by HPLC to collect the fractions containing the desired substance,. i.e. fractions No.8 to No.10 of 50 mM sodium acetate (pH 5.5) containing 0.1M NaCl.

The combined fraction was adjusted to pH 4.5 with 100 mM acetic acid, subjected to HPLC (TSK Gel SP-5PW, 5.5×20 cm, product of Toyo Soda Mfg. Co., Ltd.) and to elution under the following conditions to obtain fractions of 65 to 72 minutes in retention time (r.t.).

Eluent A: 50 mM sodium acetate (pH 5.5)

Eluent B: 50 mM sodium acetate (pH 5.5) containing 0.5M NaCl

Flow rate:30 ml/min

Concentration gradient:

| Time (min) | % B |
|---|---|
| 0 | 0 |
| 30 | 0 |
| 84 | 9 |
| 104 | 100 |
| 124 | 100 |
| 134 | 0 |
| 180 | 0 |

Thus, polypeptide I was obtained as purified.

By ultrafiltration (YM-5 membrane), the product was concentrated to 20 mg/ml in the form of a solution of 20 mM sodium phosphate buffer (pH 7.0) by changing the buffer.

The concentrate was further passed through a filter apparatus equipped with Posidyne filter NFZ (product of Nohon Pall) for sterilization to obtain a pure product which was up to 100 pg/mg protein in pyrogen content.

The purification process afforded about 3 g of polypeptide I from 300 liters of *E. coli* culture.

(2) The fractions (r.t. 64 to 65 min) of the first half of the main peak of the above (1) was subjected to the chromatography again to obtain polypeptide X. $2.7 \times 10^6$ GIF units/ mg protein.

Similarly, the fractions (r.t. 72 to 76 min) of the second half of the main peak gave polypeptide XI. $2.8 \times 10^7$ GIF units/ mg protein.

(3) Polypeptides I, X and XI obtained by the procedures (1) and (2) above were subjected to amino acid analysis in the same manner as in the Example 2-(II) (4).

Table 7 below shows the results.

The amino acid sequence of polypeptides X and XI was analyzed in the same manner as in Example 2-(II) (4) to identify the sequence at the N terminal thereof.

TABLE 7

| Amino acid | Mole rato | | |
|---|---|---|---|
| | Polypeptide I | Polypeptide X | Polypeptide XI |
| Asp and/or Asn | 17.7 | 17.5 | 16.4 |
| Ser | 13.0 | 13.0 | 12.9 |
| Thr | 5.8 | 5.7 | 5.7 |
| Glu and/or Gln | 24.0 | 24.0 | 23.0 |
| Gly | 8.6 | 8.5 | 8.5 |
| Ala | 5.2 | 5.2 | 4.1 |
| Val | 10.3 | 10.2 | 10.1 |
| Met | 5.8 | 6.7 | 5.8 |
| Ile | 4.9 | 4.9 | 4.8 |
| Leu | 15.5 | 15.6 | 15.6 |
| Tyr | 3.6 | 3.7 | 3.8 |
| Phe | (9) | (9) | (9) |
| Lys | 14.98 | 14.7 | 14.3 |
| His | 1.0 | 1.0 | 1.0 |
| Trp | present | present | present |
| Arg | 2.9 | 2.8 | 3.0 |

(4) Polypeptide I has two Cys residues (at the 8-and 71-positions) within the molecule. The state of SH group present on the side chain of these Cys residues was checked by the following method.

a. About 5 nmoles of polypeptide I obtained in Example 2-(II) (3) (in the form of 100 μl of solution of 50 mM sodium acetate (pH 5.5) containing 0.1M NaCl) was placed into each of three test tubes A, B and C. A 300 μl quantity of 6M guanidine hydrochloride solution containing 0.1M tris-HCl (pH 8.45) was further placed into each tube.

Next, 25 μl of 6M guanidine hydrochloride solution was placed into each of the tubes A and B to prepare blanks. Into the test tube C was placed 25 μl of 6M guanidine hydrochloride solution containing 2 μmoles of dithiothreitol serving as a reducing agent. Nitrogen gas was introduced into each test tube for 1 minute, and the tube was thereafter allowed to stand at 50° C. for 2 hours.

Subsequently, 25 μl of 6M guanidine hydrochloride solution was placed into the blank test tube A, and 25 μmoles of 6M guanidine chloride solution containing 4 μmoles of iodoacetamide into each of the test tubes B and C. After introducing nitrogen gas into each test tube for 1 minute, the tube was allowed to stand in the dark at 25° C. for 30 minutes.

With addition of 5 μl of 10% TFA to the mixture in each of the test tubes A, B and C thus prepared, the mixture was subjected to reverse-phase HPLC ($C_3$) to purify the protein.

About 1/10 of the quantity of purified protein was placed into a test tube, dried, hydrolyzed with 4N methanesulfonic acid and checked for amino acid composition.

Consequently, nearly equal quantities of carboxymethyl-cysteine were detected from the test tubes B and C, whereas polypeptide I in the test tube A remained unchanged. This indicates that the polypeptide in the test tubes B and C was converted to S-carboxamidemethylated polypeptide I (since the polypeptide in the test tube B was not exposed to the reducing agent), therefore revealing that no disulfide (S-S) linkage was formed by the Cys residues in polypeptide I.

Further the product remaining in each of the test tubes A, B and C was dried and then dissolved in 600μl of 1% ammonium bicarbonate solution. The solution was adjusted to a concentration of 1 μg/5 μl. A trypsin solution (7.5 μl) was added to the solution to digest the protein with the enzyme at 37° C. for 20 hours.

The enzymatic reaction was terminated by addition of 10 μl of 10% TFA to the mixture, and peptide fragments were separated off by reverse-phase HPLC ($C_{18}$).

As a result, the test tubes B and C exhibited nearly the same pattern, while the test tube A showed a pattern different therefrom.

The peptides thus isolated were checked for amino acid composition in the same manner as above. The peptide fragment in the test tube A revealed the presence of peptide which would not occur in the absence of Cys.

These results demonstrated that no disulfide linkage was formed intramolecularly or intermolecularly by the Cys residue of polypeptide.

b. The SH groups in polypeptide I were quantitatively determined by the Ellman method (Arch. Biochem. Biophys., 82, 70 (1959)) in the following manner.

A 200 µg quantity (11.5 µmoles) of polypeptide I obtained in Example 2-(II) (3) was dissolved in 1 ml of 0.1M tris-HCl buffer (pH 8.0) containing 6M guanidine hydrochloride and 1 mM EDTA. On the other hand, fresh 0.05M phosphate buffer (pH 7.0) was prepared which contained 0.01M DTNB (5,5'-dithiobis(2-nitrobenzoic acid). (The buffer will hereinafter be referred to as the "Ellman buffer.")

One ml of 0.1M tris-HCl buffer (pH 8.0) containing 6N guanidine hydrochloride and 10 mM EDTA was placed into a control cell, and 1 ml of the above solution containing polypeptide I into a specimen cell. A 40 µl quantity of the Ellman reagent was admixed with the contents of each cell, whereupon the absorbance of the mixture was measured at 412 nm. After a maximum absorbance was achieved, the reduction in the absorbance due to the decomposition of DTNB was corrected to "0" in determining the concentration of SH groups.

The absorbance actually obtained at 412 nm was 0.328.

On the other hand, $\epsilon_{412}$ of 3-carboxylate-4-nitrothiophenolate ion in an aqueous solution containing 6M guanidine hydrochloride was $13880 M^{-1} \cdot cm^{-1}$ (Eur. J. Biochem., 30, 32 (1972)). This revealed that the SH groups in the polypeptide I solution were 0.0000245 in M/e and that 11.5 µmoles of polypeptide I contained 24.5 µmoles of SH groups.

The above result demonstrated that the Cys residues contained in polypeptide I had a free SH group.

Further little or no change was found in GIF activity and in the quantity of SH groups determined by the Ellman method when a solution of polypeptide I in water or in PBS (−) was repeatedly lyophilized 3 to 4 times.

(5) When a hetero protein is expressed in a large amount in $E.$ $coli$ or the like by a gene recombination technique, the protein is not infrequently accumulated as an inclusion body in $E.$ $coli$ cells. In such a case, collection of the protein from the cells requires a treatment under severe conditions which, for example, involve use of a denaturing agent such as 7M guanidine hydrochloride, 8M urea, 0.1% SDS, or the like. Such a treatment, however, is very likely to irreversibly cause damage to the desired protein including a higher structure thereof. Accordingly, it is a matter of great interest in gene recombination techniques to isolate the desired protein under mild conditions without using the denaturing agent to the greatest possible extent. In this respect, the method (1) described above is very favorable since the desired protein can be extracted and isolated under a very mild condition, i.e. by osmotic shock. The method is desirable also because the desired protein obtained has a higher structure resembling that of natural product.

(6) Using plasmid ptrpGIF-α, the polypeptide (IL-1β derivatives of the invention) listed in Table 8 below were prepared by site-specific mutanenesis in the same manner as in Example 3-(1). The polypeptides were expressed and purified and GIF activity thereof was measured by the above procedure (1), and SDS-PAGE was conducted in the same manner as in Example 2-(II) (4). In the examples to follow, like methods were used unless otherwise stated.

TABLE 8

| Polypeptide | Primer | Constructed plasmid | Host ($E.$ $coli$) | M.W. (kd) | GIF Acitvity (units/ml culture) |
|---|---|---|---|---|---|
| XII | 5'-GAAAAGCTTTTTGTC-3' | ptrpGIF-α-98L | W3110 | 17.5 | $2.0 \times 10^3$ |
| XVII | 5'-TGGCTCCTGTATCTCTGAA-3' | ptrpGIF-α-4R-d | HB101 | 17.4 | $7.3 \times 10^4$ |
| XVIII | 5'-ACTGCACTCTCGACTCACA-3' | ptrpGIF-α-11R-d | HB110 | 17.4 | $4.6 \times 10^2$ |
| XIX | 5'-AGATGGAAAAGTTTGTCTT-3' | ptrpGIF-α-98R-d | W3110 | 17.4 | $2.3 \times 10^3$ |
| XX | 5'-CTCTGAACGCCACTCTCC-3' | ptrpGIF-α-8A | HB101 | 17.5 | $2.4 \times 10^6$ |
| XXI | 5'-GTTCTCTGAACACTCTCCG-3' | ptrpGIF-α-8C-d | HB101 | 17.4 | $1.6 \times 10^6$ |
| XXII | 5'-ACCTGTCCGCCGTGTTGA-3' | ptrpGIF-α-71A | HB101 | 17.5 | $1.6 \times 10^6$ |
| XXIII | 5'-ACCTGTCCGTCGTGTTGA-3' | ptrpGIF-α-71V | HB101 | 17.5 | $1.2 \times 10^6$ |
| XXIV | 5'-TGTACCTGTCCGTGTTGAA-3' | ptrpGIF-α-71C-d | HB101 | 17.4 | $3.5 \times 10^2$ |
| XXV | 5'-CCAAAGCTGAAGATG-3' | ptrpGIF-α-93L | HB101 | 17.5 | $5.5 \times 10^5$ |
| XXVI | 5'-ATATAACTTAATTCACCA-3' | ptrpGIF-α-144CT | HB101 | 16.5 | $2.6 \times 10^2$ |
| XXVII | 5'-TCACCATGTAATTTGTGT-3' | ptrpGIF-α-148CT | HB101 | 16.9 | $2.4 \times 10^2$ |
| XXVIII | 5'-TTCCCCAACCGGTACATC-3' | ptrpGIF-α-120R | HB101 | 17.5 | $8.5 \times 10^5$ |
| XXIX | 5'-AAAGCTCTCTACCTCCAG-3' | ptrpGIF-α-30Y | HB101 | 17.5 | $3.2 \times 10^5$ |
| IX | 5'-CCCAAGTGGTAGATCAGCA-3' | ptrpGIF-α-121Q | HB110 | 17.5 | $3.2 \times 10^4$ |
| XXXV | 5'-CCCAAGTGGTAGATCAGCA-3' | ptrpGIF-α-121Q | W3110 | 13.7 | $3.9 \times 10^2$ |
| XXXIX | 5'-ATCGATAATGCGTTCTCT-3' | ptrpGIF-α-NT3AA-d | HB101 | 17.4 | $1.2 \times 10^5$ |
| XXXX | 5'-ATCGATAATGAACTGCAC-3' | ptrpGIF-α-NT6AA-d | HB101 | 16.8 | $9.4 \times 10^2$ |
| XXXXI | 5'-ATCGATAATGCTCCGGGA-3' | ptrpGIF-α-NT9AA-d | HB110 | 16.5 | $2.4 \times 10^2$ |
| XXXXII | 5'-ATGGCTCCTCGTTCTCTG-3' | ptrpGIF-α-3V-d | HB101 | 17.4 | $2.9 \times 10^5$ |
| XXXXIII | 5'-CCTGTACGTCTGAACTGC-3' | ptrpGIF-α-5S-d | HB101 | 17.4 | $8.4 \times 10^2$ |
| XXXXIV | 5'-AAGATGGAACGATTTGTC-3' | ptrpGIF-α-97K-d | HB101 | 17.4 | $8.9 \times 10^2$ |
| XXXXV | 5'-GAAAAGCGAGTCTTCAAC-3' | ptrpGIF-α-99F-d | HB101 | 17.4 | $2.7 \times 10^2$ |
| XXXXVI | 5'-ATGCAATTTTAATCTTCCTA-3' | ptrpGIF-α-150CT | HB101 | 17.2 | $2.7 \times 10^5$ |
| XXXXVII | 5'-TTGTGTCTTAATAAAGAG-3' | ptrpGIF-α-152CT | HB101 | 17.4 | $8.0 \times 10^5$ |

(7) Using plasmid ptrpGIF-α-102CT obtained in Example 1-(6) and $E.$ $coli$ W3110 as the host, polypeptide XXX, an IL-1β derivative of the invention, was prepared by similar expression and purification procedures. About 11.4 kd (by SDS-PAGE).

(8) Using plasmid ptrpGIF-α-4G and 5'-GCACTCTCCAGGACTCACA-3' as the primer, polypeptide XIV expression plasmid ptrpGIF-α-4G11Q was prepared in the same manner as the procedure (6).

Using the plasmid and *E. coli* HB101 as the host, polypeptide XIV, an IL-1β derivative of the invention, was obtained by similar expression and purification procedures. About 17.5 kd (by SDS-PAGE). $2.7 \times 10^5$ GIF units/ml culture.

(9) In the same manner as in Example 1-(3), polypeptide XV expression plasmid ptrpGIF-α-4G98L was prepared using plasmid ptrpGIF-α-4G and plasmid ptrpGIF-α-98L.

More specifically, the two plasmids were cleaved with restriction enzymes EcoRI and HindIII. Subsequently, an approximately 400-bp DNA fragment was cut out from ptrpGIF-α-4G, and an approximately 4.6-kbp DNA fragment from ptrpGIF-α-98L, and the two fragments were ligated.

Using plasmid ptrpGIF-α-4G98L and *E. coli* W3110 as the host, polypeptide XV, an IL-1β derivative of the invention, was obtained through similar expression and purification procedures. About 17.5 kd (by SDS-PAGE).

(10) Plasmid ptrpGIF-α-11Q 98L for expressing polypeptide XVI was prepared in the same manner as the procedure (9) except that plasmid ptrpGIF-α-4G was replaced by plasmid ptrpGIF-α-11Q (using approximately 400-bp DNA fragment thereof).

Polypeptide XVI, an IL-1β derivative of the invention, was obtained similarly using the plasmid. About 17.5 kd (by SDS-PAGE).

(11) Plasmid ptrpGIF-α-4G11Q was used in place of plasmid ptrpGIF-α-4G in the procedure (9) to obtain about 400-bp DNA fragment from the plasmid. Plasmid ptrpGIF-α-4G11Q98L for expressing polypeptide XIII was obtained similarly using the fragment.

Polypeptide XIII, an IL-1β derivative of the invention, was obtained similarly using this plasmid. About 17.5 kd (by SDS-PAGE).

(12) Plasmid ptrpGIF-α-8A71S for expressing polypeptide XXXVI was prepared iE the same manner as in Example 1-(3) using plasmid ptrpGIF-α-8A and plasmid ptrpGIF-α-71S.

More specifically, the two plasmids were cleaved with restriction enzymes EcoRI and HindIII. Subsequently, an approximately 400-bp DNA fragment was cut out from ptrpGIF-α-8A, and an approximately 4.6-kbp DNA fragment from ptrpGIF-α-71S, and the two fragments were ligated.

Using plasmid ptrpGIF-α-8A71S and *E. coli* as the host, polypeptide XXXVI, an IL-1β derivative of the invention, was obtained by similar expression and purification procedures. About 17.5 kd (by SDS-PAGE). $8.7 \times 10^5$ GIF/units/ml culture.

(13) Plasmid ptrpGIF-α-8A71A was prepared in the same manner as the procedure (12) except that plasmid ptrpGIF-α-71A was used in place of plasmid ptrpGIF-α-71S (to use approximately 4.6-kbp DNA fragment thereof). *E. coli* HB 101 transformant harboring the foregoing plasmid was deposited under FERM No.BP1298 as "*Escherichia coli* HB 101/ptrp GIF-α-8A71A" with Fermentation Research Institute, Agency of Industrial Scienece and Technology (FERM).

Polypeptide XXXVII, an IL-1β derivative of the invention, was similarly obtained using the plasmid. About 17.5 kd (by SDS-PAGE). $1.6 \times 10^6$ GIF units/ml culture.

(14) Plasmid ptrpGIF-α-71V was used in place of plasmid ptrpGIF-α-71S in the procedure (12) to obtain about 4.6-kbp DNA fragment from the plasmid. Plasmid ptrpGIF-α-8A71V for expressing polypeptide XXXVIII was obtained similarly using the fragment.

Polypeptide XXXVIII, an IL-1β derivative of the invention, was similarly obtained using this plasmid. About 17.5 kd (by SDS-PAGE). $2.1 \times 10^6$ GIF units/ml culture.

(15) Polypeptides II to VIII and XXXI to XXXIV, IL-1β derivatives of the invention, were prepared using the transformants of Example 5-(1) to (7) and Example 3-(6) to (9) to be given below, respectively, by the procedure (1).

These products were migrated as a single band by SDS-PAGE. Polypeptides II to VIII migrated at the same position as above, while polypeptides XXXI to XXXXIV achieved the following results.

| Polypeptide XXXI | about 22 kd |
| Polypeptide XXXII | about 23 kd |
| Polypeptide XXXIII | about 27 kd |
| Polypeptide XXXIV | about 31 kd |

EXAMPLE 5

(1) Incubation of U937 cells

Human histiocytic lymphoma U937 cells (Ascenso, J. L. at al., Blood, Vol. 57, p170 (1981)), $1.4 \times 10^9$ in number, were placed into RPMI-1640 culture medium containing 25 ng/ml of 12-o-tetradecanoylphorbol-13-acetate (TPA, product of Pharmacia), 10 μg/ml of concanavalin A (ConA, product of Sigma) and 10% FCS to prepare a cell suspension having a concentration of $4 \times 10^5$ cells/ml.

Ten-ml portions of the cell suspension were separately placed into dishes (Falcon 3003), 9 cm in diameter, and incubated in 5% carbon dioxide gas at 37° C. for 3 days. After removing the culture supernatant by an aspirator, 10 ml of RPMI-1640 medium containing 10 μg/ml of bacterial lipopolysaccharide (LPS, product of Difco), 1 μg/ml of muramyldipeptide (MDP, product of Wako Junyaku Co., Ltd.) and 1 ng/ml of TPA was placed into each dish. The cells were incubated in this medium in 5% carbon dioxide gas at 37° C. for 18 hours. The U937 cells adhering to the bottom of the dish were used for preparing mRNA.

(2) Preparation of mRNA

RNA was extracted by the combination of the guanidinium/hot phenol method (Feramisco, J. R. et al., J. Bio. Chem., Vol. 257, 11024 (1982)) and the guanidinium/cesium chloride method (Glisin, V, et al., Biochemistry, Vol. 13, 2633 (1974)).

To wash the U937 cells incubated by the procedure (1), the dishes were rinsed with 5 ml of PBS(−) solution after removing the supernatant. The cells were then dissolved with 1 ml of 4M guanidine isothiocyanate solution (4M guanidine isothiocyanate (product of Fluka), 50 mM tris-HCl (pH 7.6), 10 mM EDTA and 2% sodium lauroyl sarkosinate placed into each dish. The solution was collected with rubber polisher and Pasteur pipette to obtain 420 ml of cell solution, which was maintained at 60° C. and passed through 18 G injection needle to shear the chromosome DNA. Subsequently, phenol heated to 60° C. was added to the solution in an amount equal to that of the solution, and the mixture was stirred with 18 G injection needle for further shearing. To the mixture were then added 210 ml of 0.1M sodium acetate-10 mM tris-HCl (pH 7.4)-1 mM EDTA solution and 420 ml of chloroform-isoamyl alcohol mixture (24:1 in volume ratio). The resulting mixture was vigorously agitated at 60° C. for 15 minutes, then ice-cooled and centrifuged at 3000 r.p.m. at 4° C. for 20 minutes. To the aqueous layer collected was added ethanol in two times the amount of the aqueous layer. The mixture was allowed to stand overnight at −70° C. to obtain crude RNA precipitate. The crude RNA was dissolved in 48 ml of 6M guanidine isothiocyanate-5 mM sodium citrate (pH 7.0)-0.1M β-mercaptoethanol-0.5% sodium lauroyl sarkosinate solution. Cesium chloride (19.2 g) was then dissolved in the solution. Seven-ml portions of the resulting solution was then superposed on 4 ml of 5.7M cesium chloride-0.1M EDTA (pH 7.5). The mixture was centrifuged at 31500 r.p.m. at 25° C. for 20 hours by Beckman SW40Ti rotor to collect RNA.

Thus, 9.7 mg of RNA was obtained.

To obtain mRNA from the RNA, the RNA was subjected to column chromatography using oligo(dT)-cellulose (product of Collaborative Research Inc.). For adsorption, 10 mM tris-HCl (pH 7.5)-0.5M NaCl-1 mM EDTA was used. For elution, 10 mM tris-HCl (pH 7.5)-1 mM EDTA was used.

Consequently, 400 μg of MRNA was obtained.

(3) Preparation of cDNA library cDNA library was prepared by the Okayama-Berg method by which cDNA can be expressed in animal cells. Thus, dT tail-attached vector primer for use in cDNA cloning was prepared from pcDV1, and dG tail-attached linker DNA from plasmid pL1, each by the method of Okayama et al. (Okayama, H. and P. Berg, Molecular and Cellular Biology, Vol. 3, p. 280 (1983)).

mRNA (15 μg) obtained by the procedure (2) was dissolved in 20 μl of 5 mM tris-HCl (pH 7.5)-0.5 mM EDTA (pH 7.5) aqueous solution and incubated at 65° C. for 5 minutes and then at 37° C. for 5 minutes. The reaction mixture was adjusted to a total quantity of 40 μl containing 50 mM tris-HCl (pH 8.3), 8 mM $MgCl_2$, 30 mM KCl, 0.3 mM dithiothreitol, 2 mM of each of dATP, dGTP, dCTP and dTTP, 2.8 μg of vector primer DNA, 60 units of RNase inhibitor (product of Promega Biotech) and 40 units of reverse transferase (product of Bio-Lad), followed by incubation at 37° C. for 1 hour. The reaction was terminated by addition of 2 μl of 0.5M EDTA (pH 7.5) and 2 μl of 10% SDS. Subsequently, the mixture was subjected to phenol-chloroform extraction and chloroform extraction, and the extract was precipitated from ethanol to collect vector primer cDNA:mRNA.

The collected vector primer cDNA:mRNA was incubated at 37° C. for 5 minutes in 30 μl of a reaction mixture composed of 140 mM sodium cacodylate, 30 mM tris-HCl (pH 6.8), 1 mM $CaCl_2$, 0.1 mM dithiothreitol, 0.3 μg of poly A, 66 μM dCTP and 38 units of terminal deoxynucleotidyl transferase (product of Pharmacia), whereupon 1.5 μl of 0.5M EDTA (pH 7.5) and 1.5 μl of 10% SDS were added to the mixture to terminate the reaction. The mixture was subjected to phenol-chloroform extraction and chloroform extraction, and the extract was precipitated from ethanol to collect oligo dC tail-attached cDNA:mRNA-vector primer.

The collected nucleic acid was incubated at 37° C. for 90 minutes in 20 μl of a reaction mixture comprising 7 mM tris-HCl (pH 7.5), 7 mM $MgCl_2$, 60 mM NaCl, 100 μg/ml of bovine serum albumin and 12 units of restriction enzyme HindIII (product of Nippon Gene Co., Ltd.) Subsequently, 1 μl of 0.5M EDTA (pH 7.5) and 1 μl of 10% SDS were added to the mixture to terminate the reaction, followed by extraction with phenol-chloroform and then with chloroform and by precipitation from ethanol to collect HindIII-decomposed oligo dC tail-attached cDNA:mRNA-vector primer. The product was dissolved in 10 μl of 10 mM tris-HCl (pH 7.5)-1 mM EDTA (pH 7.5) (TE (pH 7.5)). One μl portion of the solution was incubated in 10 μl of a reaction mixture comprising the above TE (pH 7.5), 0.1M NaCl and oligo dC tail-attached linker DNA (14 ng), first at 65° C. for 2 minutes and then at 42° C. for 30 minutes. The mixture was thereafter cooled to 0° C.

The reaction mixture was adjusted to 100 μl containing 20 mM tris-HCl (pH 7.5), 4 mM $MgCl_2$, 10 mM $(NH_4)_2SO_4$, 0.1M KCl, 50 μg/ml bovine serum albumin, 0.1 mM β-NAD (nicotinamide-adenine-dinucleotide, product of Pharmacia) and 0.6 μg of E. coli DNA ligase (product of Pharmacia) and incubated at 12° C. overnight. To the reaction mixture were added 40 μM of each of dATP, dGTP, dCTP and dTTP and 0.15 mM of β-NAD. Further with addition of 0.4 μg of E. coli DNA ligase, 4.6 units of E. coli DNA polymerase I (product of Boehringer Mannheim) and 1 unit of E. coli RNase H (product of Pharmacia), the mixture was incubated at 12° C. for 1 hour and then at 25° C. for 1 hour.

E. coli HB101 was transformed using the reaction mixture thus obtained. The competent cells of this strain used were a product of Bethesda Research Laboratories (BRL). The cells were transformed according to BRL's manual.

Consequently, cDNA library was obtained which contained about 21000 clones.

(4) Transfection of monkey COS-1 cells

The cDNA library obtained by the above procedure (3) was divided into groups each including about 70 clones on the average. Plasmid DNA was prepared from each group.

The plasmid DNA was prepared by the alkaline lysis method (Molecular Cloning-A Laboratory Manual, Cold Spring Harbor Laboratory, 1982, p. 368).

Incubated monkey cells, COS-1 cells (Gluzman, Y., Cell, Vol. 23, p. 175 (1981)), were infected with the plasmid DNA thus prepared from each group for transfection. The transfection was conducted by the DEAE-dextran method (Yokota, T. et al., Proc. Natl. Acad. Sci. U.S.A., Vol. 81, p. 1070 (1984)). More specifically, the COS-1 cells treated with trypsin were suspended in RPMI-1640 medium containing 10% FCS and adjusted to a concentration of $1 \times 10^6$ cells/ml. Subsequently, 500 μl portions of the suspension were placed into 6 wells of a well plate each containing 2 ml of RPMI-1640 medium containing 10% FCS. After incubating the cells at 37° C. overnight, the supernatant was removed, the cells were washed with a medium free from serum, and 1 ml of RPMI-1640 medium containing 10 μg/ml of plasmid DNA, 0.4 mg/ml of DEAE-dextran (product of Pharmacia), 50 mM tris-HCl (pH 7.4) and 10% FCS was placed into each well, followed by incubation at 37° C. for 4.5 hours. The supernatant was thereafter removed, the cells were washed with a medium free from serum and 2 ml of RPMI-1640 medium containing 150 μM chloroquine (product of Sigma Chemical Co.) and 10% FCS was placed into each well, further followed by incubation at 37° C. for 3 hours. The supernatant was removed, and the cells were washed with a medium free from serum and thereafter incubated at 37° C. for 72 hours with addition of 3 ml of RPMI-1640 medium containing 10% FCS to the cells in each well. After collecting the supernatant, 2 ml of RPMI-1640 medium containing 10% FCS was placed into each well, followed by two freeze-thaw cycles. The cell extract was then collected. The culture supernatant and the-cell extract were checked for GIF activity.

The group exhibiting GIF activity was divided into 24 groups of 10 clones each, and the same procedure as above was repeated using these groups for the determination of GIF activity. The same procedure as above was repeated for the clones within the group exhibiting GIF activity to identify the clone exhibiting GIF activity.

Consequently, two kinds of clones, i.e. pcD-GIF-16 and pcD-GIF-207, were obtained.

Table 9 shows the GIF activity (GIF units/ml) of these clones.

TABLE 9

| Clone | Culture supernatant | Cell extract |
|---|---|---|
| pcD-GIF-16 | 48.3 | 120.7 |
| pcD-GIF-207 | 62.6 | 196.9 |
| pcDV1 (control) | 0 | 0 |

(5) Analysis of clones

To check whether the GIF-active substances derived from the two clones were identical, serially diluted antiserum for neutralizing the GIF activity of polypeptide I was added to each of the culture supernatant and cell extract of pcD-GIF-16 or pcD-GIF-207 which exhibited definite GIF activity, whereby the influence of the antiserum on the supernatant and the cell extract was determined.

The results are shown in FIG. 21-a (pcD-GIF-16 culture supernatant), FIG. 21-b (pcD-GIF-16 cell extract), FIG. 21-c (pcD-GIF-207 culture supernatant) and FIG. 21-d (pcD-GIF-207 cell extract). In each of these diagrams, the serum dilution ratio (folds) is plotted as abscissa vs. the GIF activity (%) as ordinate, and (1) represents anti-polypeptide I serum and (2) represents normal serum.

As shown in FIGS. 21-a and 21-b, the GIF activity derived from pcD-GIF-16 was completely neutralized by the addition of anti-polypeptide I serum concentration-dependently, whereas FIGS. 21-c and 21-d reveal that GIF activity derived from pcD-GIF-207 was totally unaffected by the anti-polypeptide I serum. This indicates that the GIF-active substance from pcD-GIF-207 immunologically differs from polypeptide I and the GIF-active substance derived from pcD-GIF-16.

Figure 22:
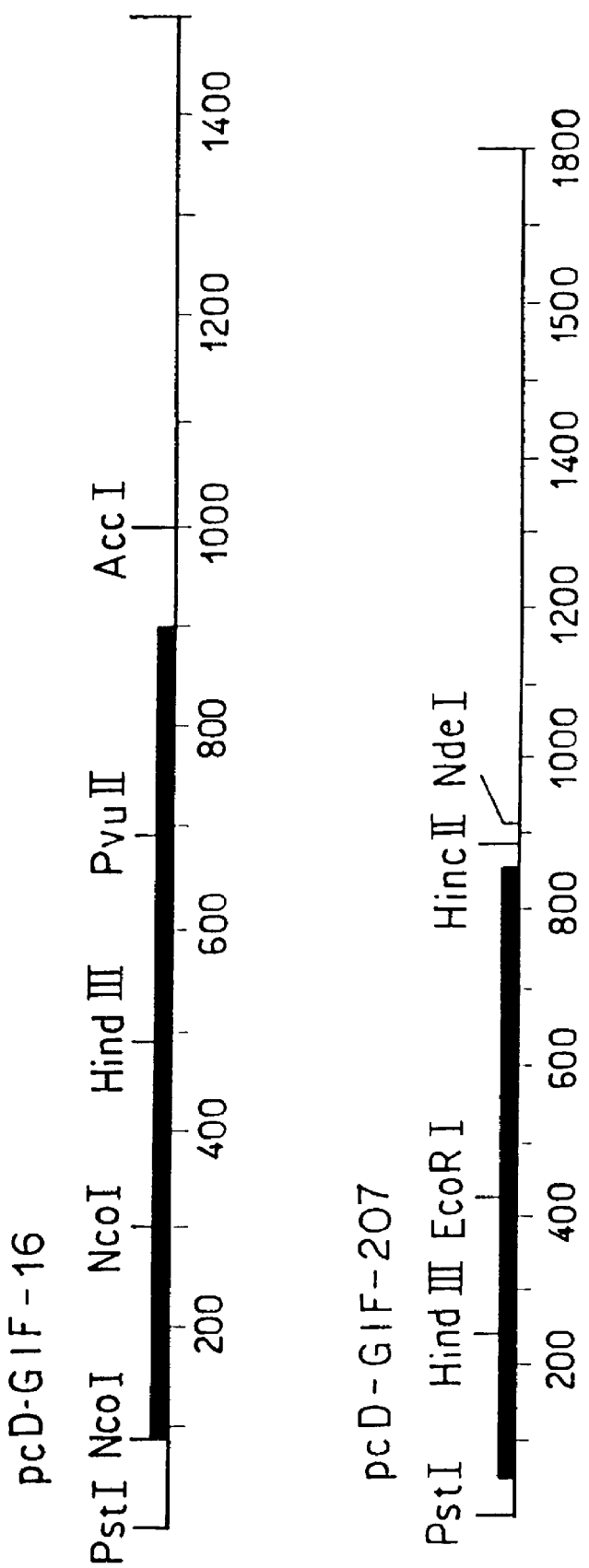
FIG. 22 is a restriction enzyme map of cDNA of plasmid pcD-GIF-16 and of plasmid pcD-GIF-207.

FIG. 22 shows a cDNA restriction enzyme map of plasmid pcD-GIF-16 and that of plasmid pcD-GIF-207. The cDNA base sequence of these plasmids were determined by the base-specific chemical modification method (Methods in Enzymology, Vol, 65, p. 499 (1980)) and by dideoxy chain termination (Proc. Natl. Acad. Sci., U.S.A., Vol. 74, p. 5463 (1977)) using phage M13 vector (Gene, Vol, 19, p. 269 (1982)).

The results established that the cDNA possessed by pcD-GIF-16 was identical with the cDNA sequence in the coding region of IL-1β as determined by March et al. and that cDNA of pcD-GIF-207 was identical with the cDNA sequence in the coding region of IL-1α (Carl J. March et al., Nature, Vol, 315, p. 641 (1985)).

(6) Preparation of polypeptide XXXIV

The cDNA clone pcD-GIF-16 of IL-1β also most of full length and obtained by the procedure (5) was cleaved with restriction enzyme PvuII, further partially cleaved with restriction enzyme NcoI and electrophoresed on agarose gel to isolate and purify 380-bp NcoI-PvuII DNA fragment.

Mung bean nuclease was caused to act on the DNA fragment, whereby the cohesive end produced by cleavage with restriction enzyme NcoI was smoothened.

Next, the 5' terminals of synthetic oligonucleotides (5'-GATAATG-3' and 5'-CATTAT-3') were phosporylated with T4 polynucleotide kinase and ligated with the DNA fragment with T4DNA ligase. The ligated block was cleaved with restriction enzymes ClaI and HindIII and then electrophoresed on agarose gel, giving about 400-bp ClaI-HindIII DNA fragment A as isolated and purified.

On the other hand, expression plasmid ptrpGIF-α previously prepared was cleaved with restriction enzymes ClaI and HindIII. DNA fragment B, which was the larger, was isolated and purified by agarose gel electrophoresis.

The fragments A and B were ligated with T4DNA ligase, and the ligated block was transformed into E. coli HB101.

The plasmid DNA of the resulting transformants was extracted, and the cleavage mapping with restriction enzymes was analyzed to select the desired transformant.

The desired transformant thus isolated (E. coli HB101/ptrpGIF-α-V) was incubated overnight with shaking at 37° C. in 10 ml of LB medium containing 50 μg/ml of L-tryptophan. M9 minimum medium (50 ml) containing 50 μg/ml of ampicillin and 1% Casamino acid was inoculated with 1 ml of the culture, followed by incubation at 37° C. with shaking. When the absorbance of the culture reached about 1.0 at 550 nm, the cells were collected and suspended in 5 ml of 15% sucrose-50 mM tris-HCl-50 mM EDTA (pH 8.0). To the suspension were added 500 μl of solution of 10 mg/ml of lysozyme (as dissolved in 10 mM tris-HCl (pH 8.0)) and 5 ml of 0.3% Triton ×100-187.5 mM EDTA (pH 7.0)–150 mM tris-HCl (pH 8.0) solution. The mixture was allowed to stand at room temperature for 15 minutes, then sonicated and centrifuged to obtain a supernatant of cell extract.

The GIF activity of the supernatant was found to be 112 units/ml culture.

(7) Preparation of polypeptide XXXII

Plasmid pGIF-α obtained previously was cleaved with restriction enzymes NcoI and AccI and electrophoresed on agarose gel to isolate and purify about 0.7-kb NcoI-AccI DNA fragment, which was treated with DNA polymerase I (Klenow fragment) to smoothen its opposite ends.

On the other hand, plasmid pTM1 was cleaved with restriction enzyme HindIII and treated with DNA polymerase I (Klenow fragment) to smoothen the cut end.

The two DNA fragments were ligated with T4DNA ligase, and the ligated block was transformed into E. coli HB101. Plasmid DNA was extracted from the transformants by the boiling method. The desired transformant was selected with reference to the restriction enzyme map of the extract.

The transformant (E. coli HB101/ptrpGIF-α-III) thus isolated was incubated in the same manner as E. coli HB101/ptrpGIF-α-V in the foregoing procedure (6) to obtain a cell extract supernatant. The GIF activity of this supernatant was 190 units/ml culture.

(8) Preparation of polypeptide XXXIII

The plasmid for expressing this polypeptide was prepared by removing unnecessary portions of base sequence by site-specific mutagenesis as will be described in detail below.

pGIF-α was cleaved with restriction enzymes PstI and AccI and then electrophoresed on agarose gel to isolate and purify about 0.9-kb PstI-AccI DNA fragment, which was treated with T4 DNA polymerase to smoothen its opposite ends.

Using T4DNA ligse, this fragment was ligated to a DNA fragment separately prepared from plasmid pTM1 by cleavage with restriction enzyme HindIII and treatment with DNA polymerase (Klenow fragment) to provide a smooth cut end. The ligated block was transformed into E. coli HB101. The desired transformant was selected with reference to the restrction enzyme map of plasmid DNA extracted by the boiling method. The DNA base sequence of the plasmid obtained was also identified. This plasmid will hereinafter be referred to as "pTM1-I-2".

Next, plasmid pTM1-I-2 was cleaved with restriction enzymes EcoRI and HindIII and electrophoresed on agarose gel to isolate and purify about 740-bp EcoRI-HindIII DNA fragment, which was then ligated to EcoRI and HindIII restriction enzyme sites of M13mp11 phase (RF) using T4DNA ligase. Single-stranded DNA (mp11-trp-I-2(E/M)) was obtained from the product for use as a template for mutagenesis.

Synthetic oligonucleotide (5'-CACGTAAAAAGGGTATCGATAATGAAGTGCTCCT-3' (primer)) was phosphorylated with T4 polynucleotide kinase and hybridized with ss mpll-trp-I-2(E/M). The hybrid was annealed, treated with DNA polymerase I (Klenow fragment) and with T4DNA ligase in the presence of dNTPs, and incubated at 15° C. for 2 days.

The DNA obtained was transformed into JM105 competent cells and an agar plate was inoculated with 200 of the resulting colonies, followed by incubation at 37° C. for 18 hours. A filter containing the grown colonies was treated with an alkali in the usual manner for denaturation, dried and then baked at 80° C. for 2 hours. The filter was hybridized and further hybridized at room temperature with $^{32}$P-probe prepared by labeling the primer with $^{32}$P-$\gamma$-ATP at its 5' end. The resulting filter was washed with 6×SSC buffer at room temperature for 10 minutes and then with 0.25×SSC buffer at 60° C. for 5 minutes, dried and thereafter autoradiographed at −70° C. for 18 hours.

mp11-trp GIF-α-IV(E/M) was selected from among the mutant clones as a typical example, infected with JM105 and incubated to prepared ss DNA and RF DNA.

M13 dideoxy chain termination sequencing of the resulting ss DNA showed that the desired gene had been deleted.

Further about 630-bp EcoRI-HindIII DNA fragment was isolated from the resulting RF DNA and purified by agarose gel electrophoresis.

On the other hand, about 4.2-kb EcoRI-HindIII DNA fragment was similarly isolated from plasmid pTM1-I-2 and purified, and was ligated with the above fragment, i.e. approximately 630-bp EcoRI-HindIII DNA fragment, using T4DNA ligase. The ligated block was transformed into *E. coli* HB101.

The desired transformant was selected with reference to the restriction enzyme map of plasmids extracted by the boiling method from the transformants obtained.

The transformant (*E. coli* HB101/ptrpGIF-α-IV) thus isolated was incubated in the same manner as *E. coli* HB101/ptrpGIF-α-V in the procedure (6) to obtain a cell extract supernatant, which was found to have GIF activity of 336 units/ml culture.

(9) Preparation of polypeptide XXXXI

In the same manner as the procedure (8), a transformant harboring plasmid ptrpGIF-α-II for expressing the desired polypeptide was prepared.

The template used was the same as ss DNAmp11-trp-I-2(E/M) used above. The primer used was synthetic oligonucleotide (5'-CACGTAAAAAGGGTATCGATAATGCTGGTTCCCT-3').

The plasmid-harboring transformant (*E. coli* HB101/ptrpGIF-α-II) was similarly incubated to obtain a cell extract supernatant, which was found to have GIF activity of 112 units/ml culture.

While the GIF activity of IL-1β (polypeptide I) of the invention and the derivatives thereof according to the invention has been described, the following tests were conducted.

Table 10 shows the LAF activity (U) per mg of polypeptides, calculated as protein of polypeptide I, as determined by the RIA method using the aforementioned antiserum against polypeptide I.

TABLE 10

| Polypeptide | LAF activity (U/mg) |
| --- | --- |
| Polypeptide I | $4.5 \times 10^6$ |
| Polypeptide II | $1.6 \times 10^5$ |
| Polypeptide III | $6.2 \times 10^6$ |
| Polypeptide IV | $2.6 \times 10^5$ |
| Polypeptide V | $2.1 \times 10^5$ |
| Polypeptide VI | $1.3 \times 10^7$ |
| Polypeptide VII | $8.0 \times 10^3$ |

Pharmacological Test Example 1

Testing polypeptide I for effect to induce CSF production
(1) Test of inducing effect on CSF production by human lung cells The following test was conducted using human embryonic lung fibroblasts (HFL-1, ATCC registered cell strain No.CCL-153) which produce CSF.

HFL-1 cells were suspended in Ham's F-12K culture (Ham, R.G., Proc. Natl. Acad. Sci., 53, 288 (1965) containing 10% FCS to a concentration of $2\times10^5$ cells/mi.

Polypeptide I obtained in the foregoing example was added to portions of the cell suspension in varying concentrations. Each of the mixtures was incubated in a carbon dioxide gas incubator at 37° C. for 24, 48 or 72 hours. The culture supernatant was collected, and the amount of CSF produced and accumulated in the supernatant was measured using mouse bone marrow cells (Lewis, I.C. et al, J. Immunol., 128, 168 (1982)).

Figure 23:
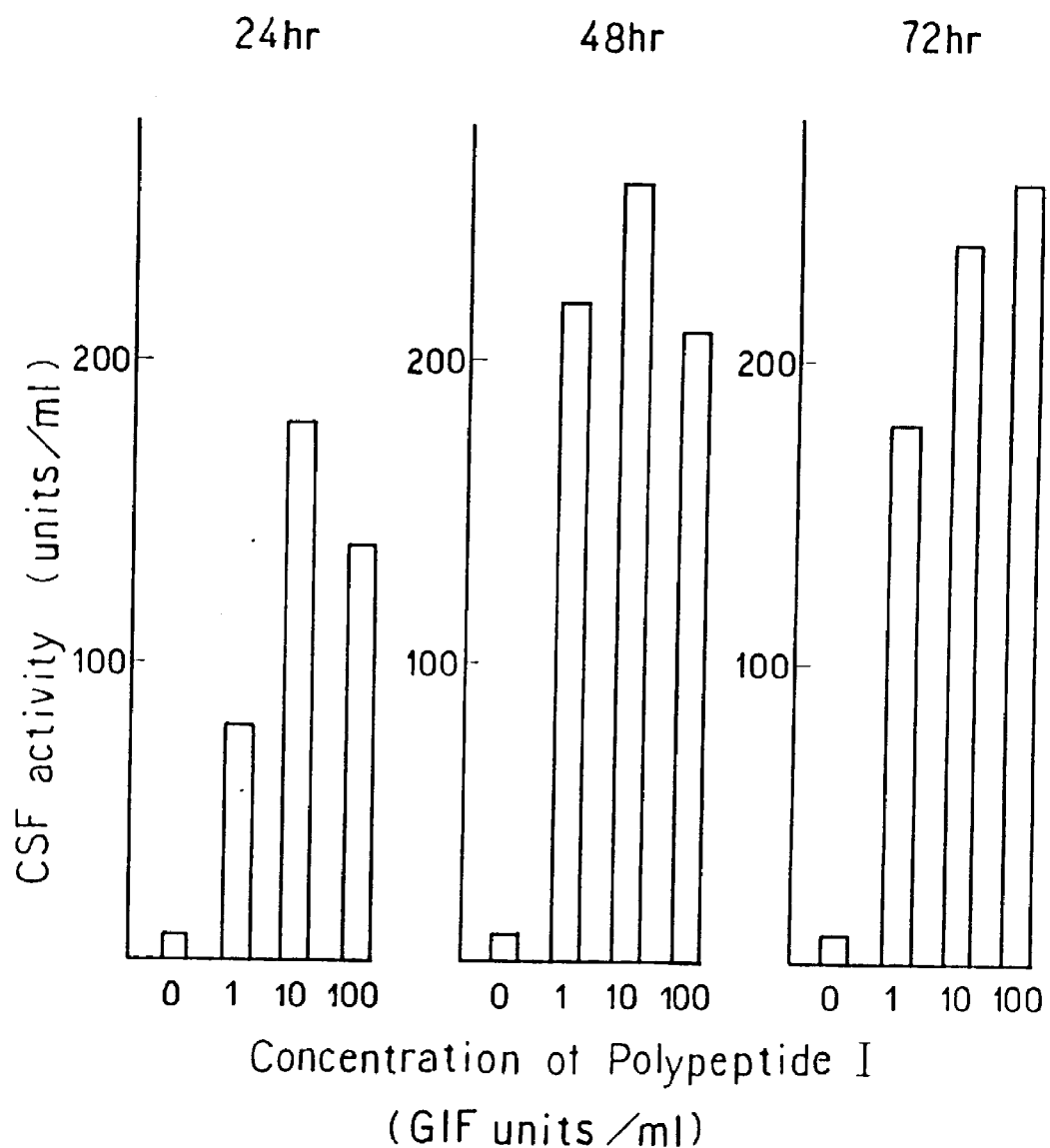
FIGS. 23 to 25 are graphs showing the results obtained by testing polypeptide I for its effect to promote production of CSF.

FIG. 23 shows the results achieved by polypeptide I during different periods of incubation. In the diagram, the concentration (GIF units/ml) of polypeptide I is plotted as abscissa vs. the CSF activity (units/ml) as ordinate.

The results achieved reveal that the addition of polypeptide I increases the amount of CSF produced by HFL-1 cell strain to as many as hundreds of times the amount produced in the absence of the polypeptide.
(2) Test of inducing effect of polypeptide I on CSF production by cells derived from human skin The following test was conducted using normal human skin-derived cell strain, CRT-1445 (ATCC No.)

Cells of the above strain were suspended in Dulbeco MEM culture medium (Dulbeco, R. and Freeman, G., Virology, 8, 396 (1959)) containing 10% FCS to a concentration of $2\times10^5$ cells/ml.

Polypeptide I obtained in the foregoing example was added to portions of the cell suspension in varying concentrations. Each of the mixtures was incubated in a carbon dioxide gas incubator at 37° C. for 24, 48 or 72 hours. The culture supernatant was collected, and the amount of CSF produced and accumulated in the supernatant was measured using mouse bone marrow cells as in the test (1).

Figure 24:
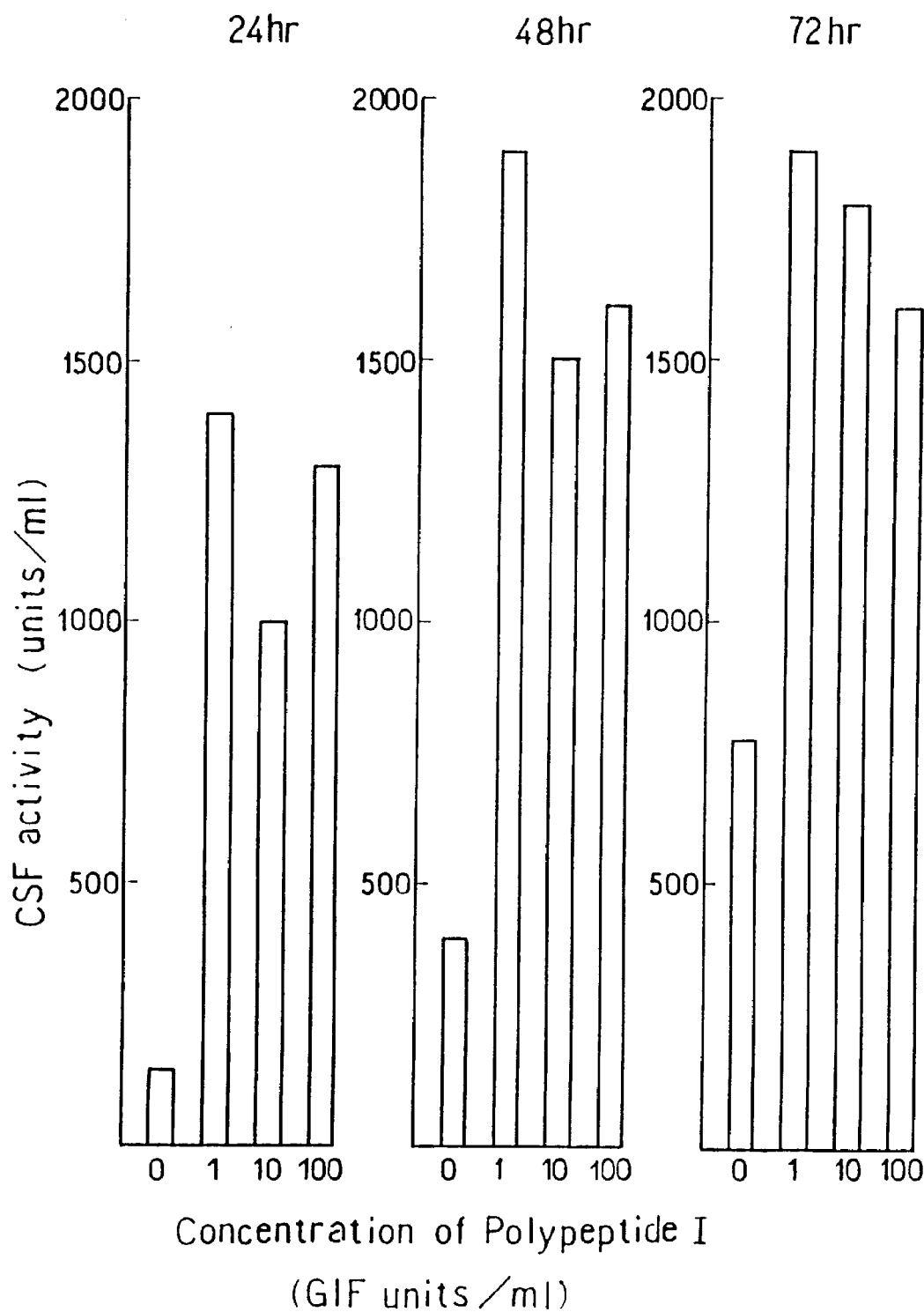

FIG. 24, like FIG. 23, shows the results achieved.

FIG. 24 shows that the addition of polypeptide in an amount of at least one unit/ml calculated as GIF activity to fibroblasts derived from the normal human skin gives the cells remarkably enhanced ability to produce CSF.
(3) Test of inducing effect on CSF production in vivo The following animal experiment was conducted to substantiate that polypeptide I, when administered to the animal, acts to induce the production of CSF in vivo.

To normal mice (BALB/C strain, purchased from Experimental Animal Cooperative Association of Shizuoka Prefecture, Japan) was intravenously given polypeptide I obtained in Example 2 in varying amounts ($10^3$ to $10^5$ units/animal calculated as GIF activity). Blood was collected from the animal 2, 4, 8, 12 and 24 hours after the administration and checked for the concentration of CSF in the serum using mouse bone marrow cells.

Figure 25:
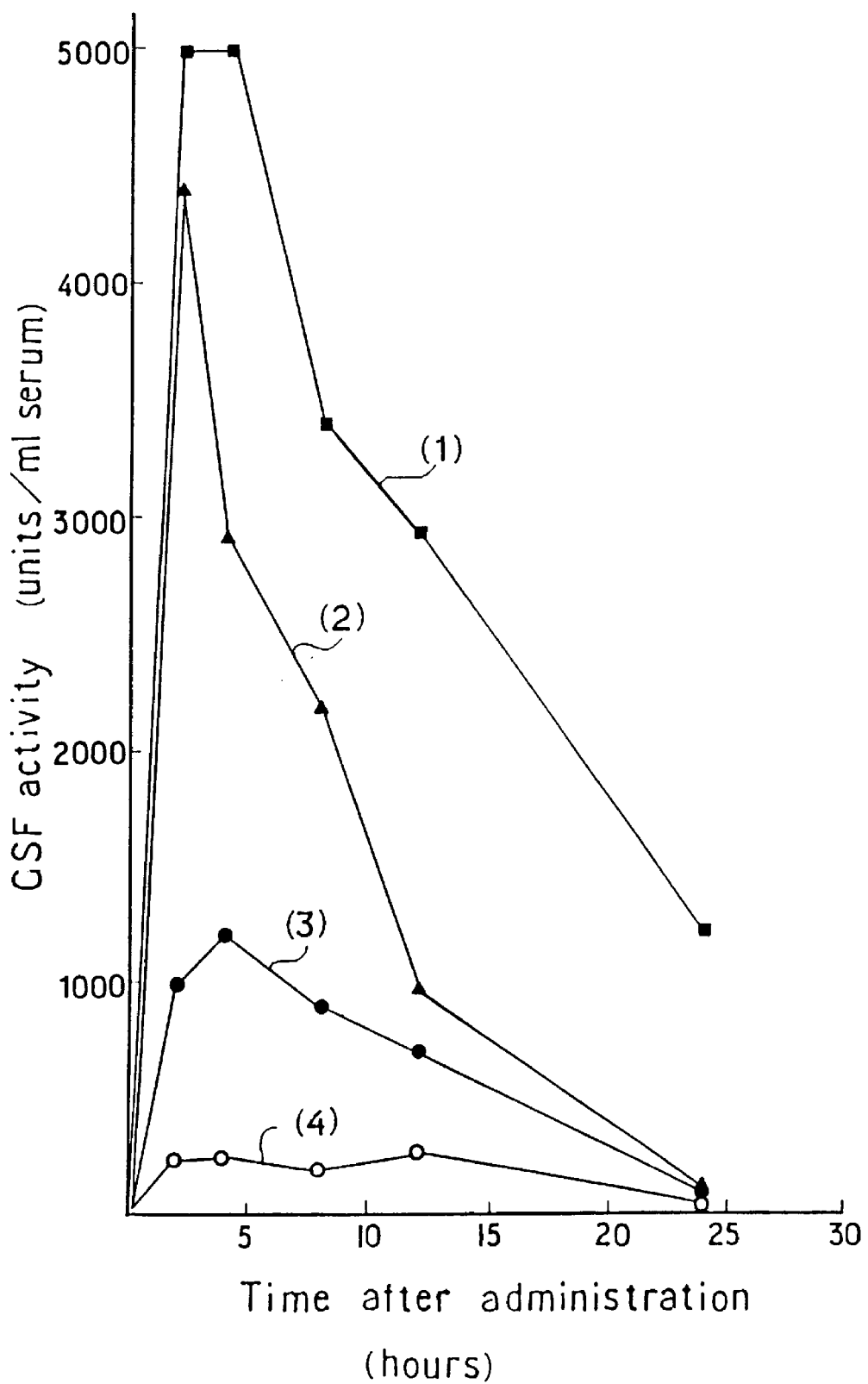

The results are given in FIG. 25, in which the time (hours) elapsed after the administration is plotted as abscissa vs. the CSF activity (units/ml serum) as ordinate. In the diagram, (1) represents a group to which polypeptide I was given at a dose of 100,000 GIF units/animal, (2) represents a group with a dose of 10,000 GIF units/animal, (3) represents a group with a dose of 1,000 GIF units/animal, and (4) represents a control group to which HSA was given at a dose of 10 $\mu$g/animal.

FIG. 25 reveals that polypeptide I, when given to animals, remarkably increases the CSF concentration of the serum of the animal. It is seen that polypeptide I greatly promotes the production of CSF in vivo in proportion to the dose.

Pharmacological Test Example 2

Rats with adjuvant arthritis were prepared by the method of Pearson (Pearson, C. M., Proc. Soc. Exp. Biol. Med., 91, 95 (1956)), Ward and Jones (Ward, J. R. and Jones, R. S., Arthritis Rheumatism, 5, 557 (1962)). More specifically, 0.05 ml of an adjuvant prepared by suspending dead cells of *Mycobacterium butyricum* in fluid paraffin was intracuteneously injected into the base portion of the tail of each of male rats of S.D. strain. On the 14th day, the animals were grouped (n=6) according to the degree of swelling of the foot. During the period of the following 5 days, polypeptide I obtained in the example or the solvent therefor (saline for the control group) was intracutaneously given to the animals. The volume of the foot was measured from day to day to evaluate the influence of the polypeptide on arthritis.

Figure 26:
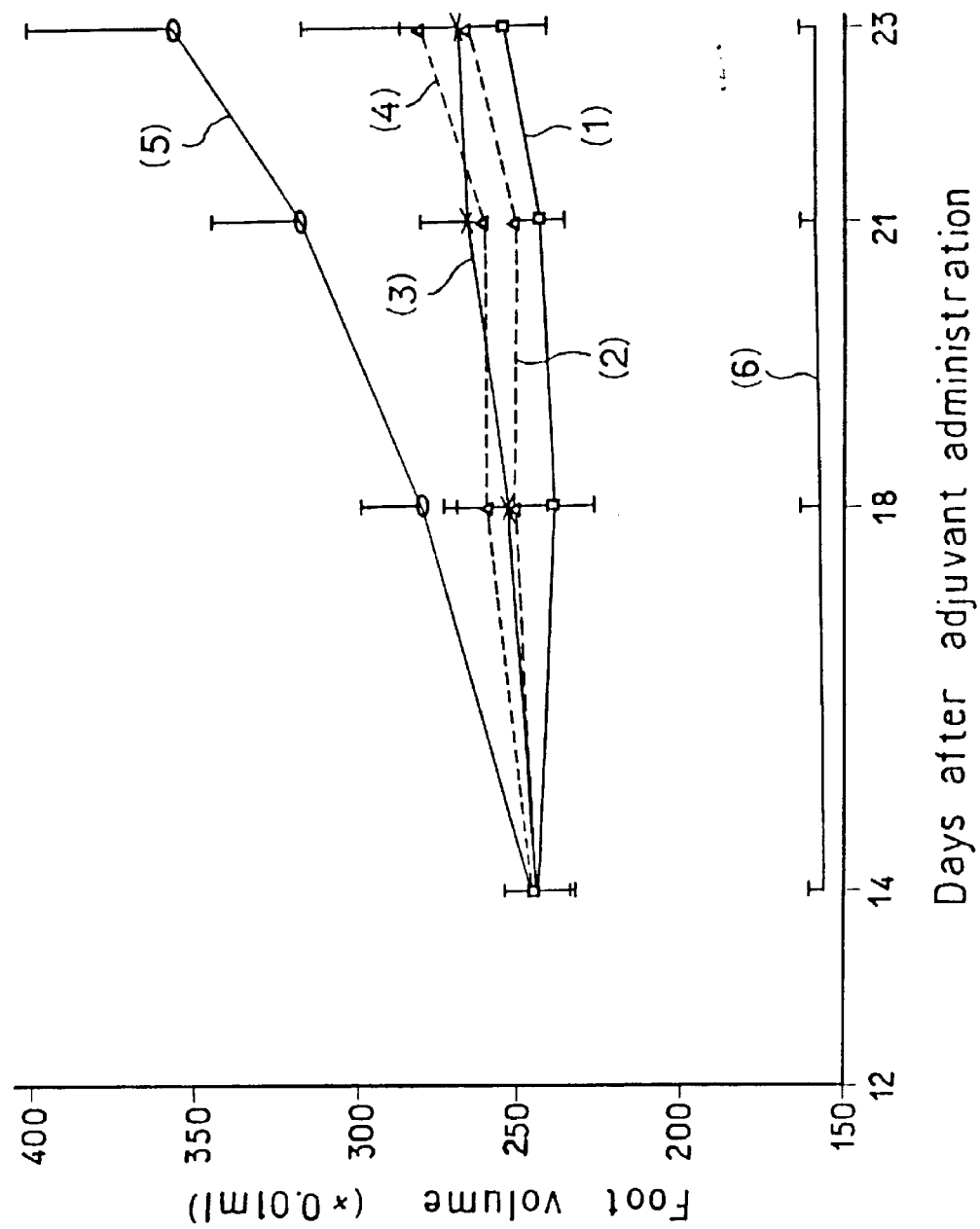
FIG. 26 is a graph showing the results obtained by testing polypeptide I for anti-arthritis effect.

The results are shown in FIG. 26, in which the number of days after the administration of the adjuvant is plotted as abscissa vs. the foot volume (×0.01 ml) as ordinate. In the diagram, a group to which polypeptide I was given at a dose of 100,000 GIF units/animal is represented by (1), a group with a dose of 10,000 GIF units/animal by (2), a group with a dose of 1,000 GIF units/animal by (3), a group with a dose of 100 GIF units/animal by (4), the control group with saline by (5), and a group of normal rats by (6).

FIG. 26 shows that the foot swelling became aggravated until the 23rd days in the control group (5) but that polypeptide I was found to exhibit swelling inhibiting activity on the groups (1) to (4) to which the polypeptide was given, on the 4th days (after the administration, i.e. 18th day after the administration of the adjuvant) and during the following period. Even 4 days after the administration of the final dose (i.e. on the 23rd day after the administration of the adjuvant), the polypeptide was found still effective for preventing progress of arthritis.

Pharmacological Test Example 3

Testing derivatives of the invention for effect to induce CSF production

The following test was conducted using cell strain U-373MG (ATCC HTB17, glioblastoma, astrocytoma, human).

Cells of the above strain were suspended in Eagle's MEM medium (product of Nissui Pharmaceutical Co.) containing 10% FCS (product of GIBCO), MEM non-essential amino acids (product of Flow) and MEM sodium pyruvate (product of Flow), to a concentration of $2 \times 10^5$ cells/ml. The substance to be tested was added in varying concentrations to portions of the suspension. Each of the mixtures was incubated in a carbon dioxide incubator at 37° C. for 24 hours.

The culture supernatant was collected, and the amount of CSF produced and accumulated in the supernatant was measured using mouse bone marrow cells (Lewis, I. C. et al., J. Immunol, 128, 168 (1982)).

Figure 27:
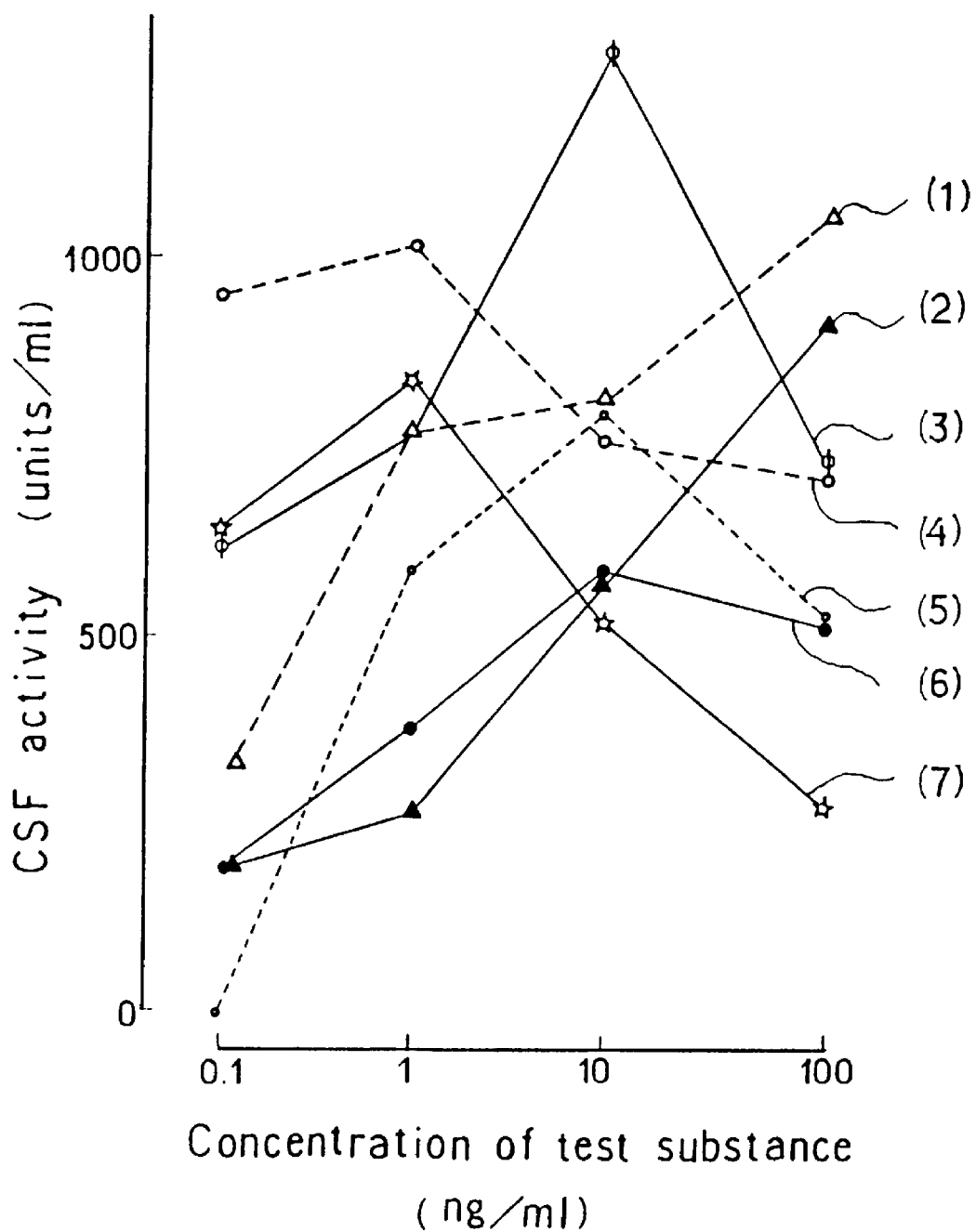
FIG. 27 is a graph showing the results obtained by testing IL-1β derivatives of the invention for CSF production promoting effect.

The results are given in FIG. 27, in which the concentration (ng/ml) of the test substance is plotted as abscissa vs. the CSF activity (U/ml) as ordinate. Curves (1) to (7) in the diagram represent the results achieved by the following polypeptides as test substances.

| Curves (1): | polypeptide VI |
| Curves (2): | polypeptide II |
| Curves (3): | polypeptide VIII |
| Curves (4): | polypeptide V |
| Curves (5): | polypeptide IV |
| Curves (6): | polypeptide III |
| Curves (7): | polypeptide XXX |

Pharmacological Test Example 4

Testing derivative of the invention for anti-inflammatory effect

The following test was conducted according to the method of Winter et al. (Proc. Soc. Exptl. Biol. Med., 111, 544–547 (1962)).

Six- to eight-week-old male rates (Spraque Dawley strain, Nippong Charles River Co., Ltd.) were used as divided into groups of 6 to 8 rats each according to the body weight one day before the experiment. A suspension of 1% Carrageenan (product of Marine Colloid) in saline, serving as an agent for causing inflammation, was subcutaneously injected in an amount of 0.1 ml into the sole of the right rear leg of the rat to cause swelling of the foot. To evaluate the swelling, the volume of the sole was measured a predetermined period before and after the injection using a plethysmometer (product of Ugo-Vasile). The ratio of the increased volume due to the injection relative to the value before the injection was calculated as swelling %.

The substance to be tested was dissolved in Dulbeco's phosphate buffered saline, and 0.1 ml of the solution was subcutaneously injected into the back of the rat 1 hour before the injection of the inflammation causing agent. The solvent was given to a control group.

Figure 28:
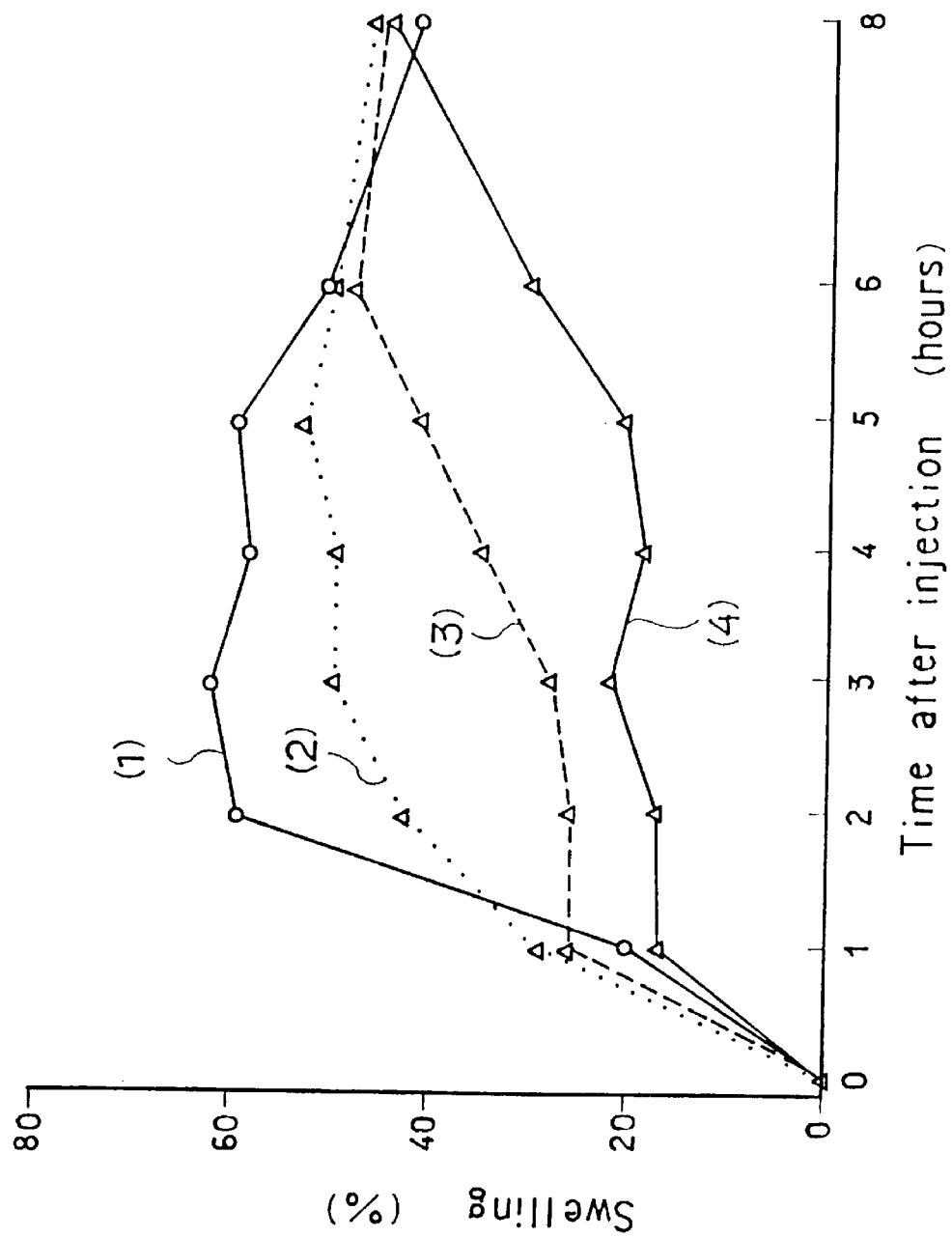
FIG. 28 is a graph showing the results obtained by testing IL-1β derivatives of the invention for anti-inflammatory effect.

The results are shown in FIG. 28, in which the time (hours) elapsed after the injection of the inflammation causing agent is plotted as abscissa vs. the swelling % as ordinate. In the diagram, the control group is represented by curve (1), a group to which 0.1 $\mu$g of polypeptide VI was given by curve (2), a group with 1 $\mu$g of polypeptide VI by curve (3), and a group with 10 $\mu$g of polypeptide VI by curve (4).

Pharmacological Test Example 5

Testing derivative of the invention for effect to prevent radiation injury

One $\mu$g or 0.3 1 $\mu$g of polypeptide VI was intraperitoneally given to each of 9-week-old mice of BALB/c strain 20 hours before the mice were exposed to a lethal dosage of X-rays.

The mice were systemically exposed to X-rays at a dose of 850 roentgens by an X-ray irradiator (MBR-1505R, product of Hitachi Medico Co., Ltd.) and thereafter checked for survival daily. PBS was given to a control group.

Figure 29:
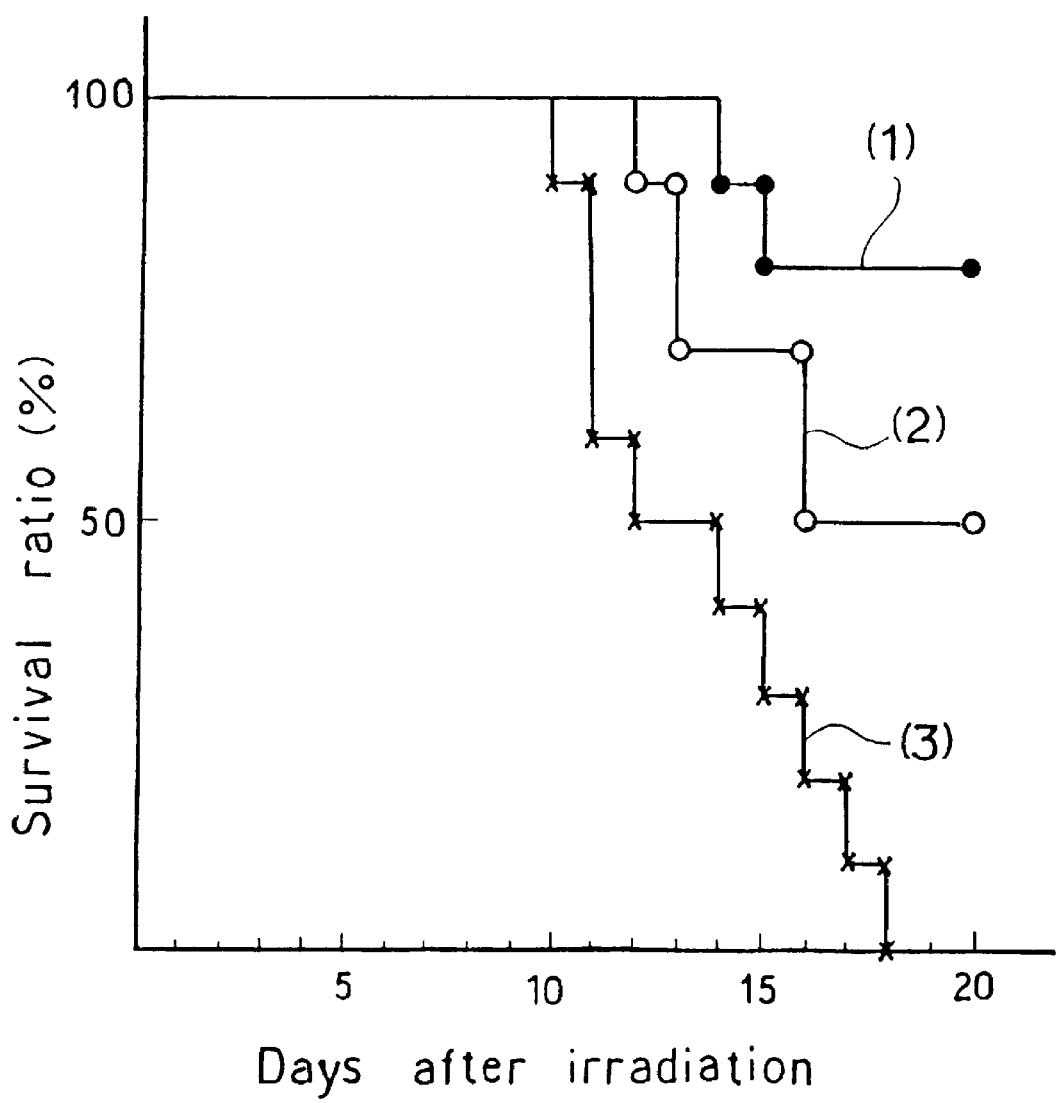
FIG. 29 is a graph showing the results obtained by testing IL-1β derivatives of the invention for activity to prevent radiation sickness.

The results are shown in FIG. 29, in which the number of days after the irradiation is plotted as abscissa vs. the survival ratio (%) as ordinate. The group to which 1 $\mu$g of polypeptide VI was given is represented by curve (1), the group with 0.3 $\mu$g of polypeptide VI by curve (2), and the control group by curve (3).

FIG. 29 shows that all the mice of the control group died on the 18th day after the X-ray irradiation, whereas polypeptide VI was found effective for preventing radiation injury depending on the dosage. It was found that about 80% of the group with the dose of 1 $\mu$g were saved from death due to radiation injury and survived.

Parmacological Test Example 6
Testing derivative of the invention for effect to prevent opportunistic infection The following test was conducted using model mouse.

On the first day, 100 mg/kg of 5-fluorouracil (5-Fu, product of Kyowa Hakko Co., Ltd.) was intravenously given to 6-week-old male mice of ICR strain (7 mice in each group). On the 2nd, 4th and 6th days, polypeptide VI of the invention was subcutaneously administered to the mice at a dose of 1 µg/mouse. On the 7th day, a specified quantity of *Pseudomonas aeruginosa* E-2 was intra-peritoneally given to the mice for infection. On the 10th day, the number of animals survived was counted to determine the survival ratio (%).

Figure 30:
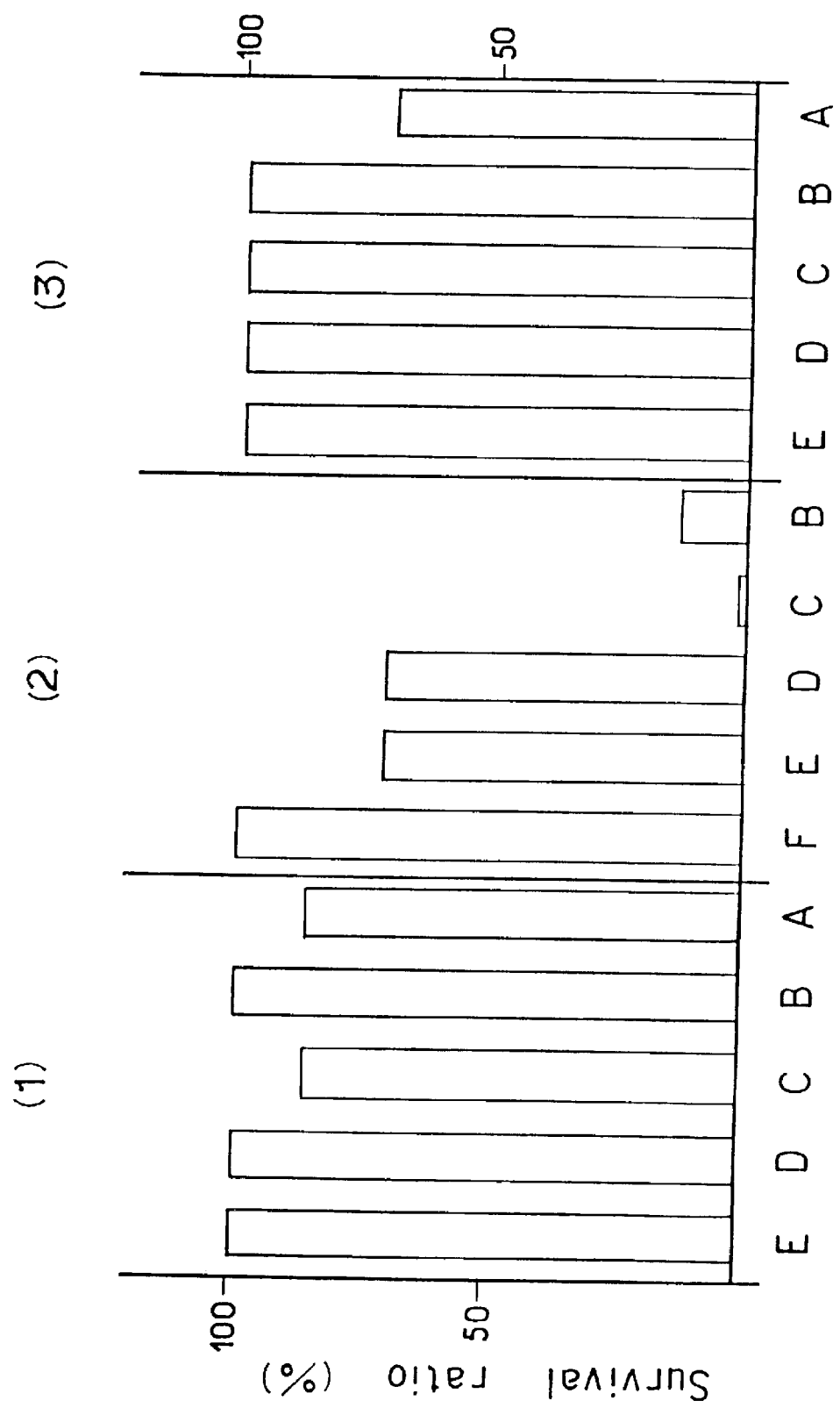
FIG. 30 is a graph showing the results obtained by testing IL1β derivatives of the invention for activity to prevent opportunistic infection.

The results are given in FIG. 30, (1) to (3). FIG. 30 (1) shows the result achieved by the group thus treated. FIG. 30 (2) shows the result achieved by a control group to which polypeptide VI was not given (but 5-Fu only was given). FIG. 30 (3) shows the result achieved by another control group to which neither 5-Fu nor polypeptide VI was given.

In FIG. 30, the survival ratio (%) is plotted as ordinate vs. groups A to E which were each given the following amount of the pseudomonas.

| Group | Number of cells/mouse |
|---|---|
| A | 19,000 |
| B | 3,800 |
| C | 750 |
| D | 150 |
| E | 30 |
| F | 6 |

Preparation Example 1

To a solution of 1×10$^7$ units/ml, calculated as GIF activity, of polypeptide VI in saline was added human serum albumin (HSA) to a concentration of 0.5%. The mixture was filtered (0.22 µm membrane filter), placed into vials, 1 ml in each, in sterile state, and lyophilized to obtain a preparation for injection.

The preparation is used as dissolved in 1 ml of distilled water for injection.

<Method of preparing cytokines from animal cells>
(1) HSB-2C5B2 cells (J. Immunol., 131, 1682–1689 (1985)), in an amount of 2×10$^5$ cells/well, were incubated for 24 hours in the presence of varying concentrations of polypeptide XXXVII and 0.01% PHA-P. The IL-2 activity of the supernatant collected was measured by the method of K. A. Smith et al. using IL-2 dependent mouse T cells (CTLL 2) (J. Immunol., 120, 2027 (1978)). Table 11 below shows the results.

TABLE 11

| Concentration of polypeptide XXXVII (mg/ml) | IL-2 activity (cpm × 10$^{-3}$) mean (n = 5) |
|---|---|
| 0 | 0.2 |
| 0.0005 | 0.3 |
| 0.005 | 1.3 |
| 0.05 | 3.9 |
| 0.5 | 3.1 |
| 5 | 4.1 |
| 50 | 4.2 |
| 500 | 4.9 |

(2) The human astroglyoma cell line U373MG was cutured to confluent in RPMI-1640 medium supplemental with 10% fetal calf serum and then was further incubated in fresh RPMI-1640 medium supplemental with 10% fetal calf serum and 20 ng/ml of the polypeptide XXXVII. After 18 hours, the medium was discarded, and total RNA was extracted by using the guanidinium-CsCl method, and poly (A)$^+$ RNA was selected by oligo-dT-cellulose chromatography. Ten µg of poly (A)$^+$ RNA was fractionated through 1.2% agarose gel in accordance with Northern blotting method and then was transferred to nitrocellulose filter. The blot was baked at 80° C. under reduced pressure and treated in 20 mM Tris-HCl (pH 8.0) at 100° C. for 5 min., following prehybridization at 42° C. in 50% formamide –5×SSC–50 mM sodium phosphate (pH 6.5) –4·× Denhardt's solution-200 µg/ml denatured solmon sperm DNA. After 5 hours, it was hybridized at 42° C. for 20 hours with PstI-NcoI DNA fragment of cDNA insert of GM-CSF (Science, 228, 810 (1985)) or KpnI-BamHI DNA fragment of cDNA insert of BSF-2 (Nature, 324, 73 (1986)), which fragment had been radio labelled by nick translation. The filter was washed in 2×SSC-0.1% SDS at room temperature for 15 min and then washed in 0.1×SSC-0.1% SDS at 50° C. for 1 hour. Autoradiography was achieved at –70° C. overnight in the presence of the intensify screen.

Figure 31:
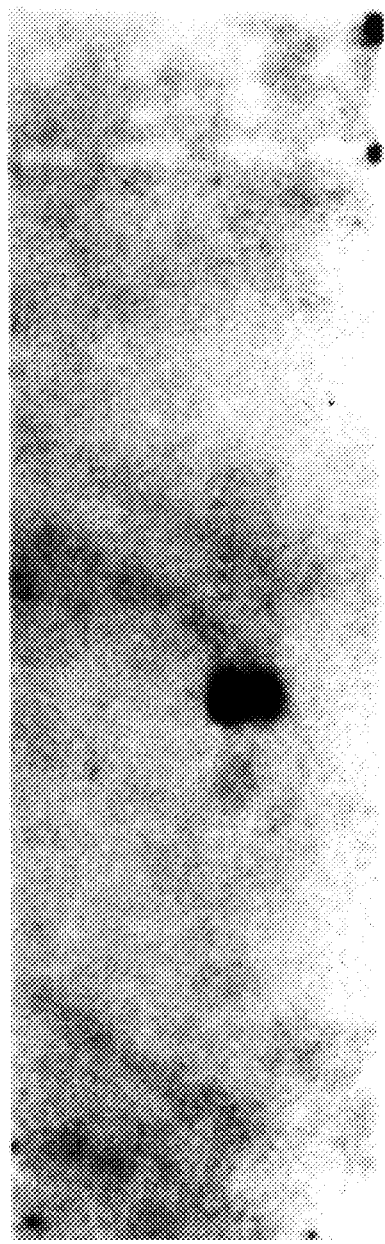
FIG. 31 is a photograph showing the results obtained by testing the IL-1β derivative of the invention for activity to induce and produce GM-CSF.
Figure 32:
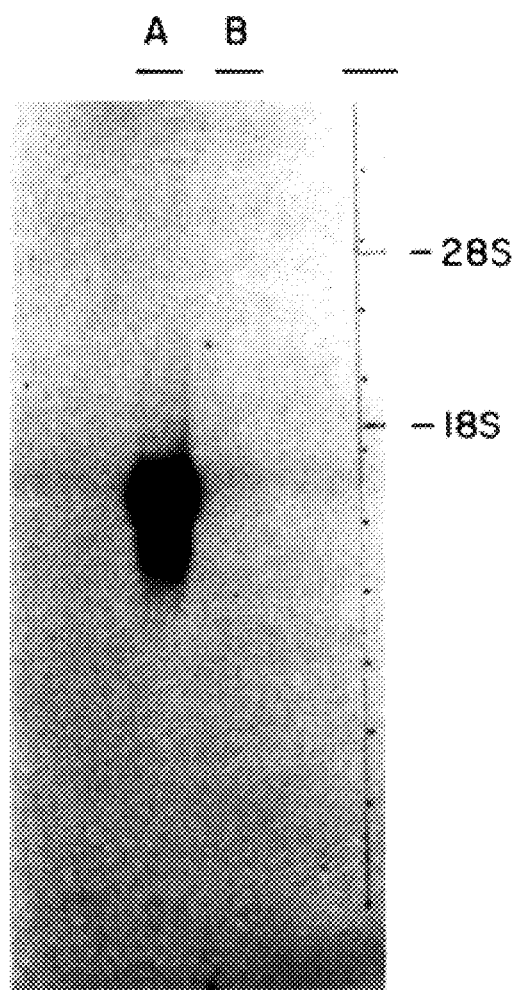
FIG. 32 is a photograph showing the results obtained by testing the IL-1β derivative of the invention for activity to induce and produce BSF-2.

FIG. 31 shows the results achieved when the DNA fragment of GM-CSF was used. Lane A represents the result attained by the use of the present polypeptide, and lane B the result of control without using the present polypeptide. Like FIG. 31, FIG. 32 shows the results achieved when the DNA fragment of BSF-2 was used.

These results indicate that the use of the polypeptide of the invention permits animal cells to produce natural-type cytokines efficiently.

The amount of the present polypeptide to be used for the above method can be very small, usually about 10 ng/ml, whereby satisfactory results are achievable, while the use of the polypeptide facilitates purification of the cytokine derived.

(3) When cytokines are to be produced from animal cells, it is essential that the polylpeptide of the invention used for inducing the production be stable in structure under the prevailing condition and be bound to the IL-1 receptor on the surface of the cells. More specifically, it is required that the present polypeptide bind to the IL-1 receptor and transmit to the cell a singal necessary for the production of the cytokine.

Accordingly, the following test was conducted in connection with the binding of the present polypeptide to the IL-1 receptor on fibroblasts.

Balb/3T3 cells (clone A31: ATCC, CCL-163, 1×10$^6$ cells/well) almost uniformly grown over a 6-well plate were reacted at 4° C. for 2 hours with 50000 cpm/well of $^{125}$I-labelled polypeptide I (IL-1β) and 20 ng/ml of polypeptide I preincubated at 37° C. in D-MEM supplemented with 10% FCS. The liquid reaction mixture was discarded with a Pasteur pipette, the cells were gently washed with 1 ml of D-MEM supplemented with 10% FCS, and the supernatant was discarded. After repeating the washing procedure twice, the cells were solubilized with 1 ml of a mixture of 1% SDS and 0.2N NaOH. The radioactivity (bound radioactivity) of the solubilized cell solution and the liquid used for washing the wells was measured by a gamma-counter.

The $^{125}$I-labeled polypeptide I used was prepared and purified by the method of Bolton and Hunter (Biochem. J., 133, 529 (1973)). Specific activity: at least 250 uCi/µg protein. Table 12 below shows the results.

TABLE 12

| Preincubation time (hr) | Inhibition activity (%) |
|---|---|
| 0 | 100 |
| 5 | About 40 |
| 30 | About 4 |

Inhibition Activity (%) = $\frac{A - B}{A - C}$ × 100 wherein

A: Bound radioactivity in absence of unlabelled polypeptide I

B: Experimental value of bound radioactivity

C: Radioactivity unspecifically absorbed on the plate

The foregoing index expresses the binding activity of the coexisting polypeptide I against IL-1 receptor.

Table 12 reveals that under the cytokine induction condition, the ability of polypeptide I, i.e. IL-1β itself, to bind to the IL-1 receptor diminishes with time. Accordingly, the same testing procedure as above was repeated using polypeptide I, VI or XXXVII which was preincubated for 24 hours. Table 13 below shows the results.

TABLE 13

| Polypeptide | Inhibition activity (%) |
|---|---|
| I | About 4 |
| VI | About 44 |
| XXXVII | About 87 |

The results given above reveal that it is more preferable to use polypeptides of the invention than IL-1β itself for preparing cytokines from animal cells.

We claim:

1. An isolated or purified DNA molecule encoding an interleukin-1β mutant, wherein said mutant contains a mutation in the amino acid sequences of interleukin-1β represented by Formula (A), and wherein said mutation is selected from the group consisting of (a), (b), and (c) as defined below, Formula (A)

```
                    5                        10
Ala—Pro—Val—Arg—Ser—Leu—Asn—Cys—Thr—Leu—
                    15                       20
Arg—Asp—Ser—Gln—Gln—Lys—Ser—Leu—Val—Met—
                    25                       30
Ser—Gly—Pro—Tyr—Glu—Leu—Lys—Ala—Leu—His—
                    35                       40
Leu—Gln—Gly—Gln—Asp—Met—Glu—Gln—Gln—Val—
                    45                       50
Val—Phe—Ser—Met—Ser—Phe—Val—Gln—Gly—Glu—
                    55                       60
Glu—Ser—Asn—Asp—Lys—Ile—Pro—Val—Ala—Leu—
                    65                       70
Gly—Leu—Lys—Glu—Lys—Asn—Leu—Tyr—Leu—Ser—
                    75                       80
Cys—Val—Leu—Lys—Asp—Asp—Lys—Pro—Thr—Leu—
                    85                       90
Gln—Leu—Glu—Ser—Val—Asp—Pro—Lys—Asn—Tyr—
                    95                       100
Pro—Lys—Lys—Lys—Met—Glu—Lys—Arg—Phe—Val—
                    105                      110
Phe—Asn—Lys—Ile—Glu—Ile—Asn—Asn—Lys—Leu—
                    115                      120
Glu—Phe—Glu—Ser—Ala—Gln—Phe—Pro—Asn—Trp—
                    125                      130
Tyr—Ile—Ser—Thr—Ser—Gln—Ala—Glu—Asn—Met—
                    135                      140
Pro—Val—Phe—Leu—Gly—Gly—Thr—Lys—Gly—Gly—
                    145                      150
Gln—Asp—Ile—Thr—Asp—Phe—Thr—Met—Gln—Phe—
Val—Ser—Ser
```

(a) Cys at the 8-position is replaced by Ala;
(b) Cys at the 71-position is replaced by Ser or Ala; and
(c) Cys at the 71-position is replaced by Ser or Ala, and Cys at the 8-position is replaced by Ala.

2. A vector containing a DNA molecule as defined in claim 1.

3. A microorganism containing a vector as defined in claim 2.

4. An isolated or purified DNA molecule having a nucleotide sequence encoding (Ser$^{71}$)IL-1β.

5. An isolated or purified DNA molecule having a nucleotide sequence encoding (Ala$^8$, Ala$^{71}$)-IL-1β.

* * * * *

UNITED STATES PATENT AND TRADEMARK OFFICE
CERTIFICATE OF CORRECTION

PATENT : 5,847,098

DATED : December 8, 1998

INVENTOR(S) : Nakai et al.

It is certified that error appears in the above-identified patent and that said Letters Patent is hereby corrected as shown below:

On the title page, under section [30]   Foreign   Application Priority Data" in Column 1, "Dec, 21, <u>1994</u> [JP]   Japan .............. 59-271207" should be -- Dec. 21, 1984 [JP]   Japan .. ............ 59-271207 --.

Signed and Sealed this

Twenty-sixth Day of October, 1999

Attest:

Attesting Officer

Q. TODD DICKINSON

Acting Commissioner of Patents and Trademarks